(12) United States Patent
Epenetos

(10) Patent No.: US 11,357,863 B2
(45) Date of Patent: Jun. 14, 2022

(54) PEPTIDE CONJUGATES

(71) Applicant: ANASTASIS BIOTEC LIMITED, London (GB)

(72) Inventor: Agamemnon Epenetos, London (GB)

(73) Assignee: Anastasis Biotec Limited, London (DK)

( * ) Notice: Subject to any disclaimer, the term of this patent is extended or adjusted under 35 U.S.C. 154(b) by 64 days.

(21) Appl. No.: 16/640,861

(22) PCT Filed: Aug. 24, 2018

(86) PCT No.: PCT/GB2018/052413
§ 371 (c)(1),
(2) Date: Feb. 21, 2020

(87) PCT Pub. No.: WO2019/038562
PCT Pub. Date: Feb. 28, 2019

(65) Prior Publication Data
US 2021/0154310 A1 May 27, 2021

(30) Foreign Application Priority Data
Aug. 25, 2017 (GB) .................................. 1713700

(51) Int. Cl.
*A61K 47/64* (2017.01)
*A61K 45/06* (2006.01)
*C07K 14/47* (2006.01)

(52) U.S. Cl.
CPC .............. *A61K 47/64* (2017.08); *A61K 45/06* (2013.01); *C07K 14/47* (2013.01)

(58) Field of Classification Search
None
See application file for complete search history.

(56) References Cited

U.S. PATENT DOCUMENTS

2009/0137470 A1  5/2009  Stylianou

FOREIGN PATENT DOCUMENTS

WO  WO 02/096952 A2  12/2002
WO  WO 2009/044173 A2  4/2009

OTHER PUBLICATIONS

Amblard et al., "Methods and Protocols of Modern Solid Phase Peptide Synthesis," Mol Biotechnol., 33(3):239-254, (2006).
"Amino Acid Secondary Structure Preferences," Biological Magnetic Resonance Data Bank, The Board of Regents of the University of Wisconsin System, (2017). [Retrieved from the Internet May 19, 2020: <URL: http://www.bmrb.wisc.edu/referenc/choufas.shtml>].
Chen et al., "Fusion protein linkers: property, design and functionality," Adv Drug Deliv Rev., 65(10):1357-1369, (2013).
Coin et al., "Solid-phase peptide synthesis: from standard procedures to the synthesis of difficult sequences," Nat Protoc., 2(12):3247-3256, (2007).
Fujiwara et al., "Dependence of α-helical and βsheet amino acid propensities on the overall protein fold type," BMC Struct Biol., 12:18, 15 pages, (2012).
Guidotti et al., "Cell-Penetrating Peptides: From Basic Research to Clinics," Trends Pharmacol Sci., 38(4):406-424, (2017).
Jeffery et al., "The preparation and characterization of poly(lactide-co-glycolide) microparticles. II. The entrapment of a model protein using a (water-in-oil)-in-water emulsion solvent evaporation technique," Pharm. Res., 10:362-368, (1993).
Moellering et al., "Direct inhibition of the Notch transcription factor complex," Nature, 462(7270):182-188, (2009).
Opacak-Bernardi et al., "Effects of cell penetrating Notch inhibitory peptide conjugated to elastin-like polypeptide on glioblastoma cells," Journal of Drug Targeting, 25(6):523-531, (2017).
Qian et al., "The des(1-6)antennapedia homeodomain: comparison of the NMR solution structure and the DNA-binding affinity with the intact Antennapedia homeodomain," Proc Natl Acad Sci USA, 91(9):4091-4095, (1994).
Qian et al., "1SAN: The des(1-6)antennapedia homeodomain: comparison of the NMR solution structure and the DNA-binding affinity with the intact Antennapedia homeodomain," Protein Data Bank, Jan. 7, 1994. [Retrieved from the Internet May 19, 2020 <URL: https://www.rcsb.org/structure/1SAN>].
Thompson et al., "CLUSTAL W: improving the sensitivity of progressive multiple sequence alignment through sequence weighting, position-specific gap penalties and weight matrix choice," Nucleic Acids Research, 22(22):4673-4680, (1994).
Verlander et al., "Industrial Applications of Solid-Phase Peptide Synthesis—A Status Report," International Journal of Peptide Research and Therapeutics, 13(1-2):75-82, (2007).
Wang et al., "Synthesis and biological activity of conjugates between paclitaxel and the cell delivery vector penetratin," Bioorganic & Medicinal Chemistry Letters, 16: 2628-2631, (2006).
Wilson and Kovall, "Crystal structure of the CSL-Notch-Mastermind ternary complex bound to DNA," Cell, 124(5):985-96, (2006).
Wu and Gehring, "Cellular uptake of the Antennapedia homeodomain polypeptide by macropinocytosis," Biochemical and Biophysical Research Communications, 443:1136-1140, (2014).
WIPO Application No. PCT/GB2018/052413, PCT International Search Report and Written Opinion of the International Searching Authority dated Dec. 21, 2018.

*Primary Examiner* — Christina Bradley
(74) *Attorney, Agent, or Firm* — Alston & Bird LLP

(57) ABSTRACT

The present invention provides peptide conjugates capable of translocating across the cytoplasmic membrane of a mammalian cell and inhibiting the Notch signalling pathway. Peptide conjugates, compositions and methods of the invention are useful for targeting chemo-resistant cancer stem cells.

19 Claims, 24 Drawing Sheets
Specification includes a Sequence Listing.

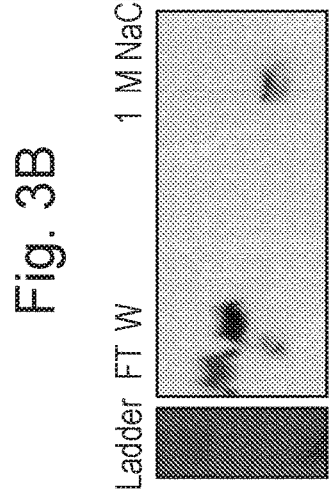
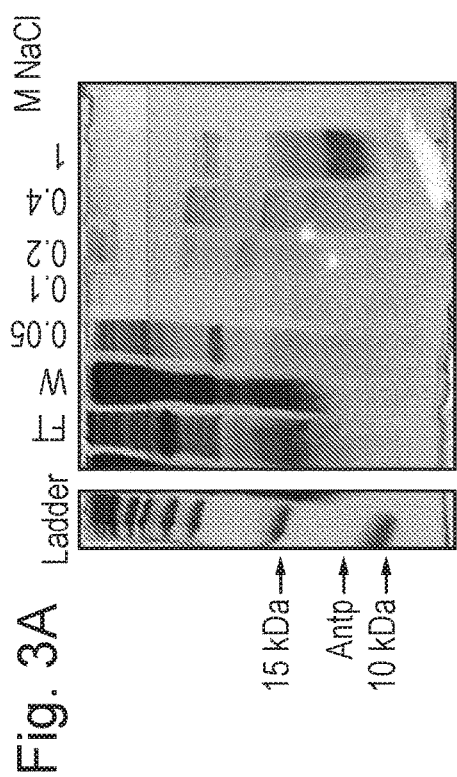
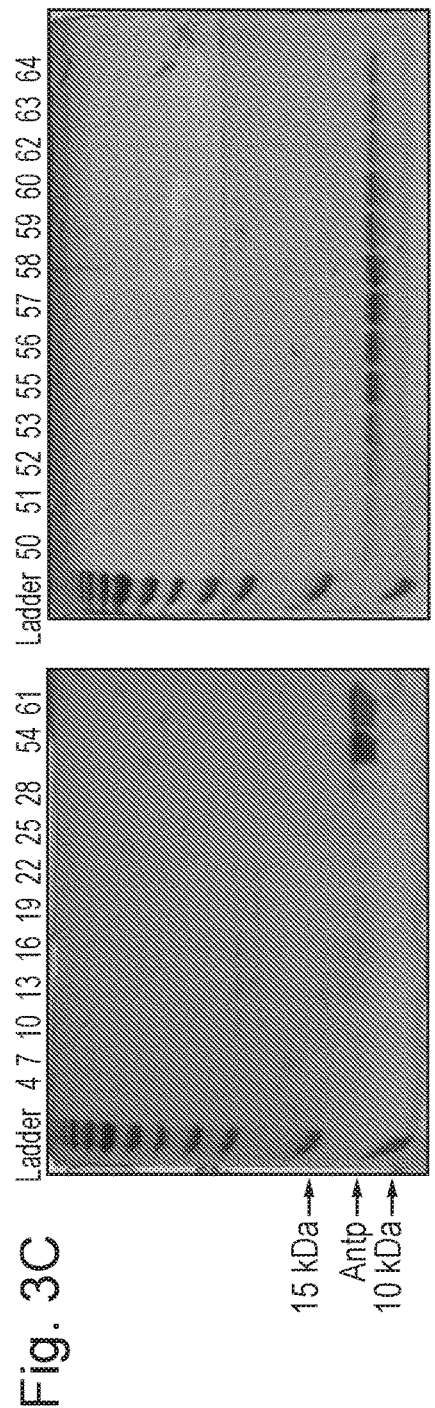

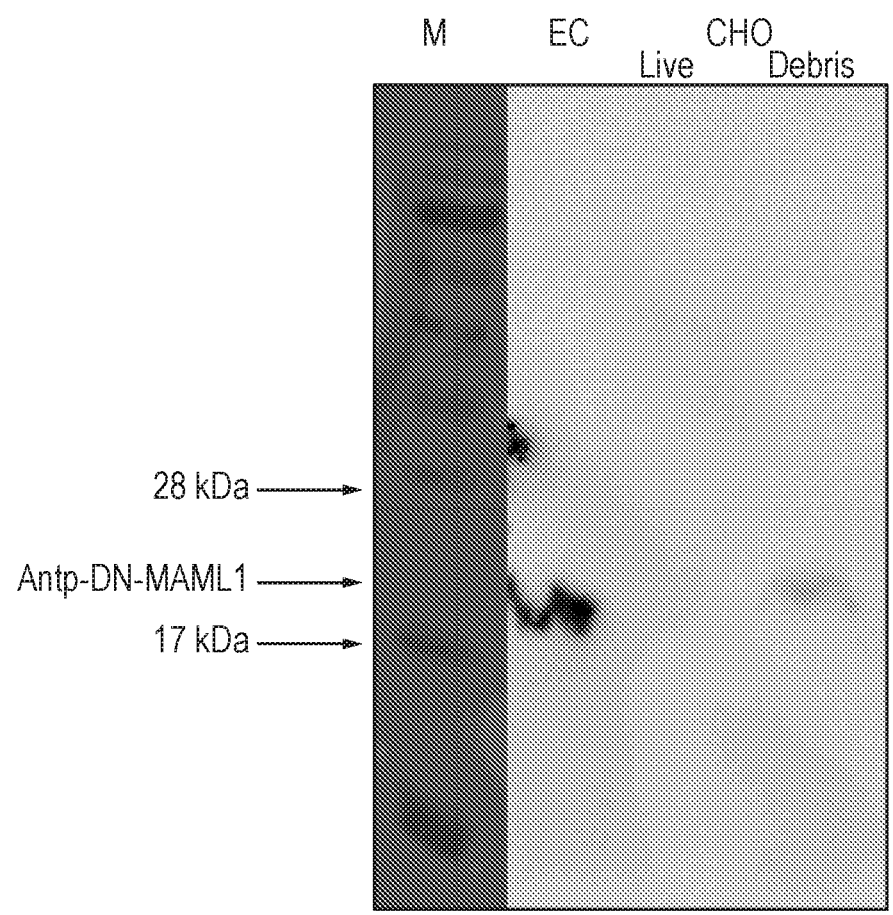

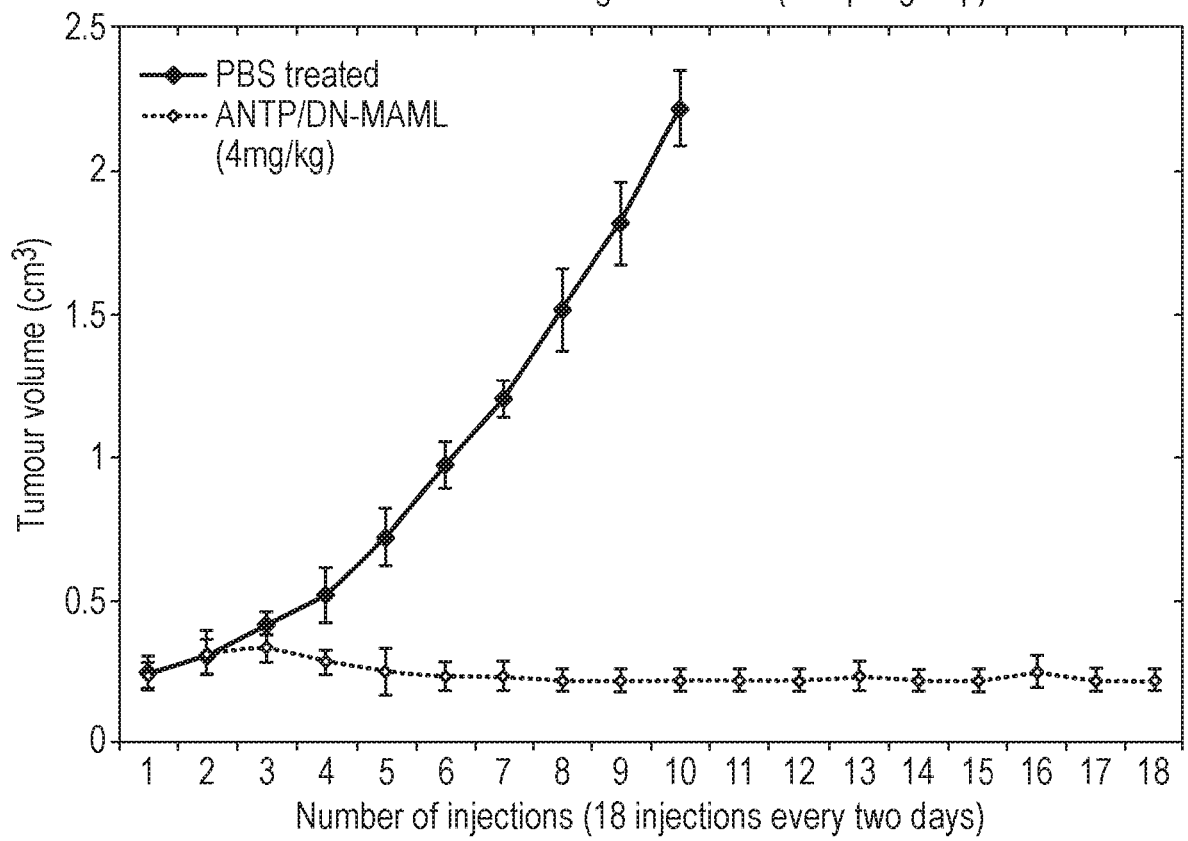

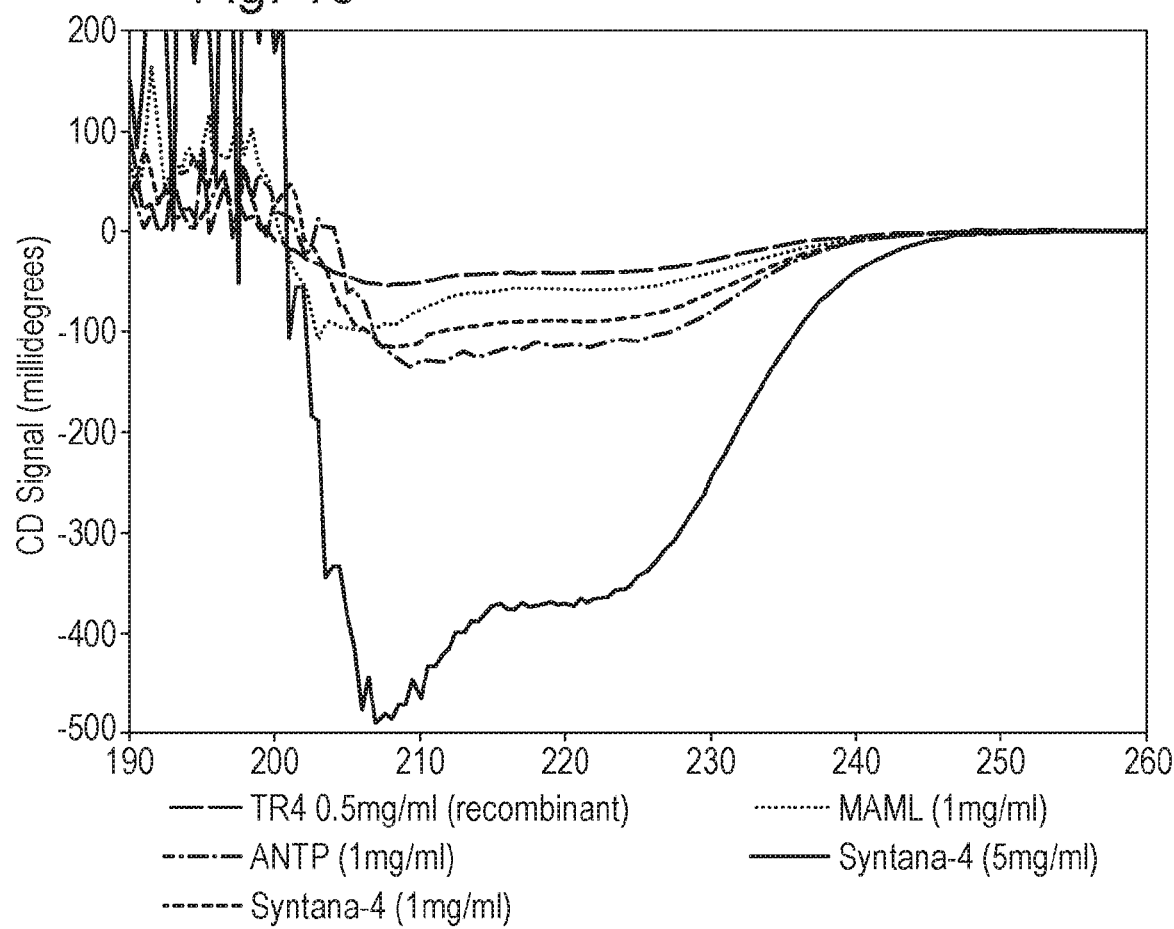

Fig. 16
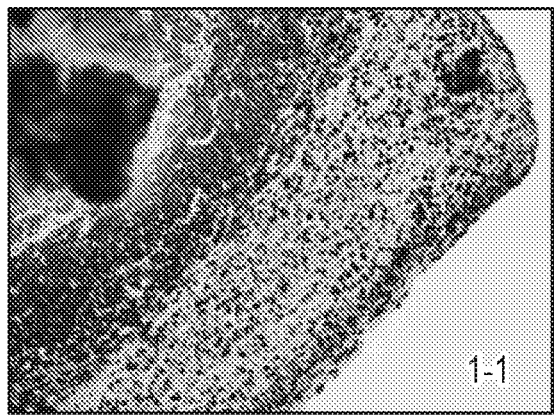
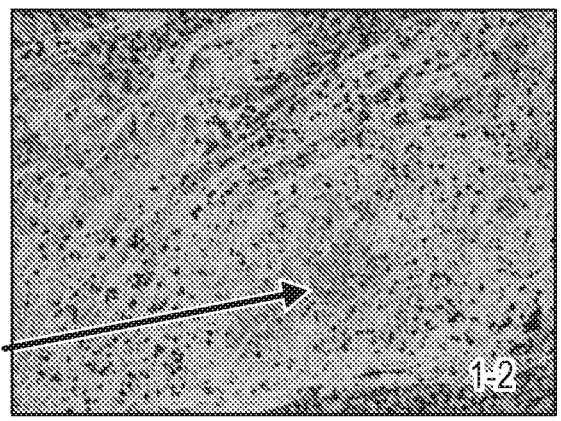
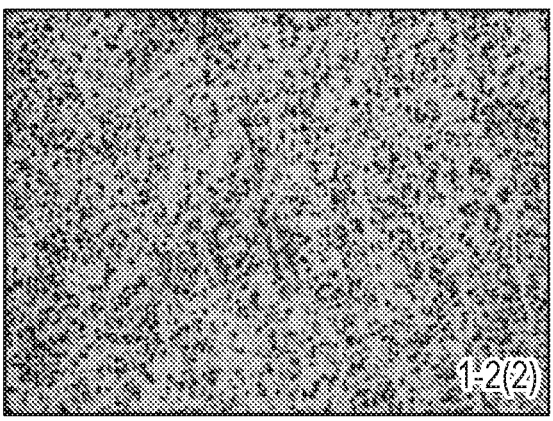
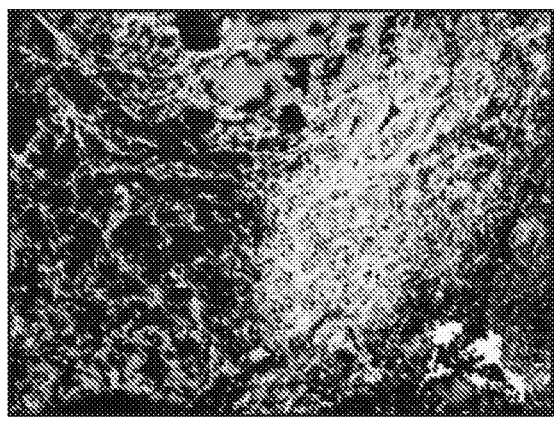

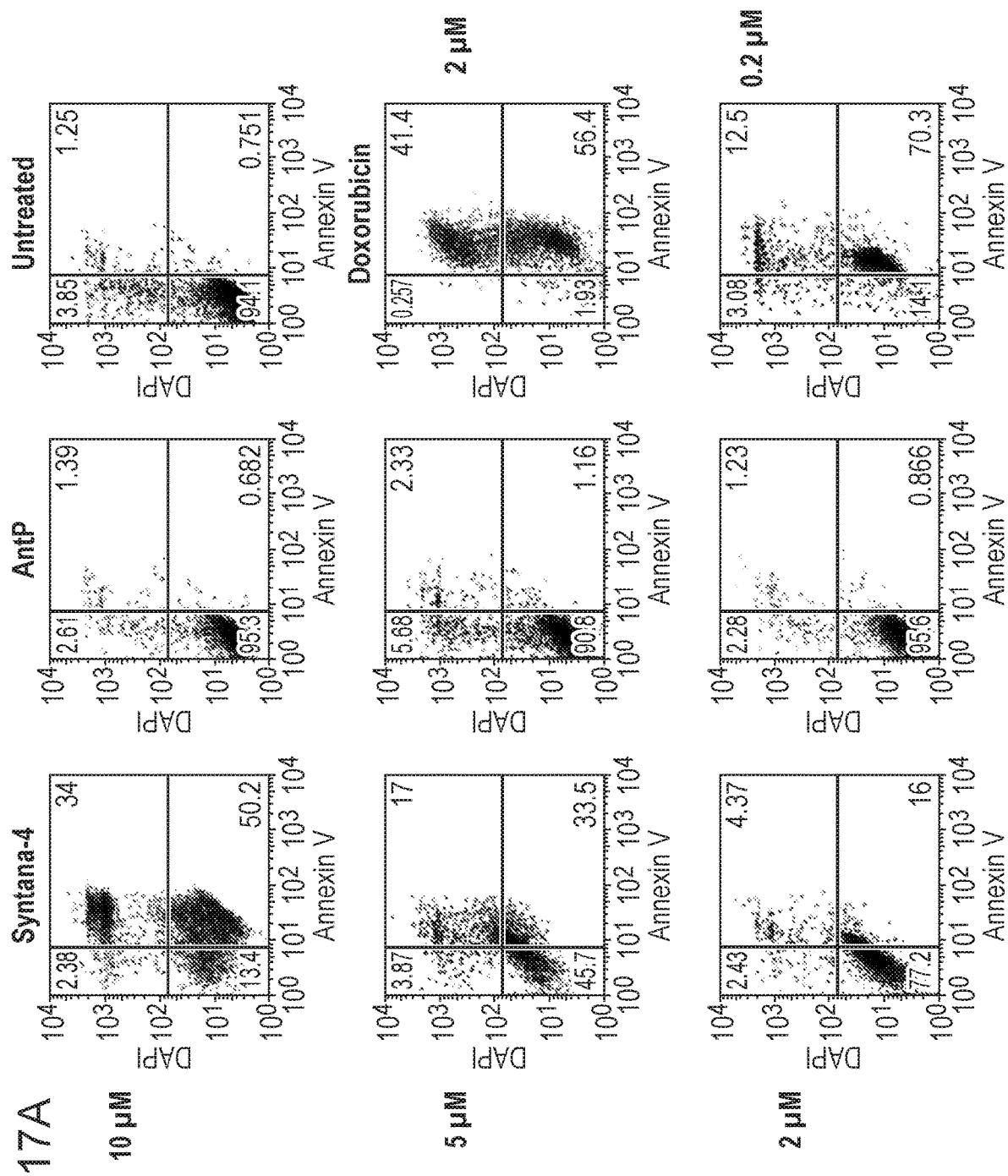

SEQUENCE LISTING

```
<160> NUMBER OF SEQ ID NOS: 28

<210> SEQ ID NO 1
<211> LENGTH: 60
<212> TYPE: PRT
<213> ORGANISM: Artificial Sequence
<220> FEATURE:
<223> OTHER INFORMATION: Homeodomain consensus sequence

<400> SEQUENCE: 1

Arg Arg Arg Lys Arg Thr Ala Tyr Thr Arg Tyr Gln Leu Leu Glu Leu
1               5                   10                  15

Glu Lys Glu Phe Leu Phe Asn Arg Tyr Leu Thr Arg Arg Arg Arg Ile
            20                  25                  30

Glu Leu Ala His Ser Leu Asn Leu Thr Glu Arg His Ile Lys Ile Trp
        35                  40                  45

Phe Gln Asn Arg Arg Met Lys Trp Lys Lys Glu Asn
    50                  55                  60

<210> SEQ ID NO 2
<211> LENGTH: 60
<212> TYPE: PRT
<213> ORGANISM: Artificial Sequence
<220> FEATURE:
<223> OTHER INFORMATION: Amino acid sequence of the Antennapedia
      homeodomain

<400> SEQUENCE: 2

Arg Lys Arg Gly Arg Gln Thr Tyr Thr Arg Tyr Gln Thr Leu Glu Leu
1               5                   10                  15

Glu Lys Glu Phe His Phe Asn Arg Tyr Leu Thr Arg Arg Arg Arg Ile
            20                  25                  30
```

Glu Ile Ala His Ala Leu Cys Leu Thr Glu Arg Gln Ile Lys Ile Trp
            35                  40                  45

Phe Gln Asn Arg Arg Met Lys Trp Lys Lys Glu Asn
        50                  55                  60

<210> SEQ ID NO 3
<211> LENGTH: 60
<212> TYPE: PRT
<213> ORGANISM: Artificial Sequence
<220> FEATURE:
<223> OTHER INFORMATION: Amino acid sequence of the Antennapedia
      homeodomain with conservative substitutions
<220> FEATURE:
<221> NAME/KEY: MISC_FEATURE
<222> LOCATION: (1)..(38)
<223> OTHER INFORMATION: Wherein X is K or R
<220> FEATURE:
<221> NAME/KEY: MISC_FEATURE
<222> LOCATION: (39)..(39)
<223> OTHER INFORMATION: Wherein X is A, C, G or S
<220> FEATURE:
<221> NAME/KEY: MISC_FEATURE
<222> LOCATION: (40)..(60)
<223> OTHER INFORMATION: Wherein X is R or K

<400> SEQUENCE: 3

Xaa Xaa Xaa Gly Xaa Gln Thr Tyr Thr Xaa Tyr Gln Thr Leu Glu Leu
1               5                   10                  15

Glu Xaa Glu Phe His Phe Asn Xaa Tyr Leu Thr Xaa Xaa Xaa Xaa Ile
            20                  25                  30

Glu Ile Ala His Ala Leu Xaa Leu Thr Glu Xaa Gln Ile Xaa Ile Trp
            35                  40                  45

Phe Gln Asn Xaa Xaa Met Xaa Trp Xaa Xaa Glu Asn
        50                  55                  60

<210> SEQ ID NO 4
<211> LENGTH: 16
<212> TYPE: PRT
<213> ORGANISM: Artificial Sequence
<220> FEATURE:
<223> OTHER INFORMATION: Penetratin

<400> SEQUENCE: 4

Arg Gln Ile Lys Ile Trp Phe Gln Asn Arg Arg Met Lys Trp Lys Lys
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: penetratin variant
<220> FEATURE:
<221> NAME/KEY: MISC_FEATURE
<222> LOCATION: (1)..(16)
<223> OTHER INFORMATION: Wherein X is R or K

<400> SEQUENCE: 5

Xaa Gln Ile Xaa Ile Trp Phe Gln Asn Xaa Xaa Met Xaa Trp Xaa Xaa
1               5                   10                  15

<210> SEQ ID NO 6
<211> LENGTH: 1016
<212> TYPE: PRT
<213> ORGANISM: Homo sapiens

<400> SEQUENCE: 6

```
Met Val Leu Pro Thr Cys Pro Met Ala Glu Phe Ala Leu Pro Arg His
1               5                   10                  15

Ser Ala Val Met Glu Arg Leu Arg Arg Ile Glu Leu Cys Arg Arg
            20                  25                  30

His His Ser Thr Cys Glu Ala Arg Tyr Glu Ala Val Ser Pro Glu Arg
        35                  40                  45

Leu Glu Leu Glu Arg Gln His Thr Phe Ala Leu His Gln Arg Cys Ile
    50                  55                  60

Gln Ala Lys Ala Lys Arg Ala Gly Lys His Arg Gln Pro Pro Ala Ala
65                  70                  75                  80

Thr Ala Pro Ala Pro Ala Ala Pro Ala Pro Arg Leu Asp Ala Ala Asp
                85                  90                  95

Gly Pro Glu His Gly Arg Pro Ala Thr His Leu His Asp Thr Val Lys
            100                 105                 110

Arg Asn Leu Asp Ser Ala Thr Ser Pro Gln Asn Gly Asp Gln Gln Asn
        115                 120                 125

Gly Tyr Gly Asp Leu Phe Pro Gly His Lys Lys Thr Arg Arg Glu Ala
    130                 135                 140

Pro Leu Gly Val Ala Ile Ser Ser Asn Gly Leu Pro Pro Ala Ser Pro
145                 150                 155                 160

Leu Gly Gln Ser Asp Lys Pro Ser Gly Ala Asp Ala Leu Gln Ser Ser
                165                 170                 175

Gly Lys His Ser Leu Gly Leu Asp Ser Leu Asn Lys Lys Arg Leu Ala
            180                 185                 190

Asp Ser Ser Leu His Leu Asn Gly Gly Ser Asn Pro Ser Glu Ser Phe
        195                 200                 205

Pro Leu Ser Leu Asn Lys Glu Leu Lys Gln Glu Pro Val Glu Asp Leu
    210                 215                 220

Pro Cys Met Ile Thr Gly Thr Val Gly Ser Ile Ser Gln Ser Asn Leu
225                 230                 235                 240

Met Pro Asp Leu Asn Leu Asn Glu Gln Glu Trp Lys Glu Leu Ile Glu
                245                 250                 255

Glu Leu Asn Arg Ser Val Pro Asp Glu Asp Met Lys Asp Leu Phe Asn
            260                 265                 270

Glu Asp Phe Glu Glu Lys Lys Asp Pro Glu Ser Ser Gly Ser Ala Thr
        275                 280                 285

Gln Thr Pro Leu Ala Gln Asp Ile Asn Ile Lys Thr Glu Phe Ser Pro
    290                 295                 300

Ala Ala Phe Glu Gln Glu Gln Leu Gly Ser Pro Gln Val Arg Ala Gly
305                 310                 315                 320

Ser Ala Gly Gln Thr Phe Leu Gly Pro Ser Ser Ala Pro Val Ser Thr
                325                 330                 335

Asp Ser Pro Ser Leu Gly Gly Ser Gln Thr Leu Phe His Thr Ser Gly
            340                 345                 350

Gln Pro Arg Ala Asp Asn Pro Ser Pro Asn Leu Met Pro Ala Ser Ala
        355                 360                 365

Gln Ala Gln Asn Ala Gln Arg Ala Leu Ala Gly Val Val Leu Pro Ser
    370                 375                 380

Gln Gly Pro Gly Gly Ala Ser Glu Leu Ser Ala His Gln Leu Gln
385                 390                 395                 400

Gln Ile Ala Ala Lys Gln Lys Arg Glu Gln Met Leu Gln Asn Pro Gln
                405                 410                 415

Gln Ala Thr Pro Ala Pro Ala Pro Gly Gln Met Ser Thr Trp Gln Gln
```

-continued

```
            420                 425                 430
Thr Gly Pro Ser His Ser Ser Leu Asp Val Pro Tyr Pro Met Glu Lys
                435                 440                 445

Pro Ala Ser Pro Ser Ser Tyr Lys Gln Asp Phe Thr Asn Ser Lys Leu
450                 455                 460

Leu Met Met Pro Ser Val Asn Lys Ser Ser Pro Arg Pro Gly Gly Pro
465                 470                 475                 480

Tyr Leu Gln Pro Ser His Val Asn Leu Leu Ser His Gln Pro Pro Ser
                485                 490                 495

Asn Leu Asn Gln Asn Ser Ala Asn Asn Gln Gly Ser Val Leu Asp Tyr
                500                 505                 510

Gly Asn Thr Lys Pro Leu Ser His Tyr Lys Ala Asp Cys Gly Gln Gly
                515                 520                 525

Ser Pro Gly Ser Gly Gln Ser Lys Pro Ala Leu Met Ala Tyr Leu Pro
                530                 535                 540

Gln Gln Leu Ser His Ile Ser His Glu Gln Asn Ser Leu Phe Leu Met
545                 550                 555                 560

Lys Pro Lys Pro Gly Asn Met Pro Phe Arg Ser Leu Val Pro Pro Gly
                565                 570                 575

Gln Glu Gln Asn Pro Ser Ser Val Pro Val Gln Ala Gln Ala Thr Ser
                580                 585                 590

Val Gly Thr Gln Pro Pro Ala Val Ser Val Ala Ser Ser His Asn Ser
                595                 600                 605

Ser Pro Tyr Leu Ser Ser Gln Gln Ala Ala Val Met Lys Gln His
                610                 615                 620

Gln Leu Leu Leu Asp Gln Gln Lys Gln Arg Glu Gln Gln Lys His
625                 630                 635                 640

Leu Gln Gln Gln Gln Phe Leu Gln Arg Gln His Leu Leu Ala Glu
                645                 650                 655

Gln Glu Lys Gln Gln Phe Gln Arg His Leu Thr Arg Pro Pro Pro Gln
                660                 665                 670

Tyr Gln Asp Pro Thr Gln Gly Ser Phe Pro Gln Gln Val Gly Gln Phe
                675                 680                 685

Thr Gly Ser Ser Ala Ala Val Pro Gly Met Asn Thr Leu Gly Pro Ser
                690                 695                 700

Asn Ser Ser Cys Pro Arg Val Phe Pro Gln Ala Gly Asn Leu Met Pro
705                 710                 715                 720

Met Gly Pro Gly His Ala Ser Val Ser Ser Leu Pro Thr Asn Ser Gly
                725                 730                 735

Gln Gln Asp Arg Gly Val Ala Gln Phe Pro Gly Ser Gln Asn Met Pro
                740                 745                 750

Gln Ser Ser Leu Tyr Gly Met Ala Ser Gly Ile Thr Gln Ile Val Ala
                755                 760                 765

Gln Pro Pro Pro Gln Ala Thr Asn Gly His Ala His Ile Pro Arg Gln
                770                 775                 780

Thr Asn Val Gly Gln Asn Thr Ser Val Ser Ala Ala Tyr Gly Gln Asn
785                 790                 795                 800

Ser Leu Gly Ser Ser Gly Leu Ser Gln Gln His Asn Lys Gly Thr Leu
                805                 810                 815

Asn Pro Gly Leu Thr Lys Pro Pro Val Pro Arg Val Ser Pro Ala Met
                820                 825                 830

Gly Gly Gln Asn Ser Ser Trp Gln His Gln Gly Met Pro Asn Leu Ser
                835                 840                 845
```

```
Gly Gln Thr Pro Gly Asn Ser Asn Val Ser Pro Phe Thr Ala Ala Ser
    850                 855                 860

Ser Phe His Met Gln Gln Gln Ala His Leu Lys Met Ser Ser Pro Gln
865                 870                 875                 880

Phe Ser Gln Ala Val Pro Asn Arg Pro Met Ala Pro Met Ser Ser Ala
                885                 890                 895

Ala Ala Val Gly Ser Leu Leu Pro Pro Val Ser Ala Gln Gln Arg Thr
            900                 905                 910

Ser Ala Pro Ala Pro Ala Pro Pro Thr Ala Pro Gln Gln Gly Leu
        915                 920                 925

Pro Gly Leu Ser Pro Ala Gly Pro Glu Leu Gly Ala Phe Ser Gln Ser
    930                 935                 940

Pro Ala Ser Gln Met Gly Gly Arg Ala Gly Leu His Cys Thr Gln Ala
945                 950                 955                 960

Tyr Pro Val Arg Thr Ala Gly Gln Glu Leu Pro Phe Ala Tyr Ser Gly
                965                 970                 975

Gln Pro Gly Gly Ser Gly Leu Ser Ser Val Ala Gly His Thr Asp Leu
            980                 985                 990

Ile Asp Ser Leu Leu Lys Asn Arg Thr Ser Glu Glu Trp Met Ser Asp
        995                 1000                1005

Leu Asp Asp Leu Leu Gly Ser Gln
    1010                1015

<210> SEQ ID NO 7
<211> LENGTH: 1096
<212> TYPE: PRT
<213> ORGANISM: Homo sapiens

<400> SEQUENCE: 7

Gly Arg Ala Glu Ser Ser Asp Arg Glu Arg Glu Ser Thr Leu Gln Leu
1               5                   10                  15

Leu Ser Leu Val Gln His Gly Gln Gly Ala Arg Lys Ala Gly Lys His
                20                  25                  30

Thr Lys Ala Thr Ala Thr Ala Ala Thr Thr Ala Pro Pro Pro
            35                  40                  45

Pro Ala Ala Pro Pro Ala Ala Ser Gln Ala Ala Ala Thr Ala Ala Pro
50                  55                  60

Pro Pro Pro Asp Tyr His His His Gln Gln His Leu Leu Asn
65              70                  75                  80

Ser Ser Asn Asn Gly Gly Ser Gly Gly Ile Asn Gly Glu Gln Gln Pro
                85                  90                  95

Pro Ala Ser Thr Pro Gly Asp Gln Arg Asn Ser Ala Leu Ile Ala Leu
            100                 105                 110

Gln Gly Ser Leu Lys Arg Lys Gln Val Val Asn Leu Ser Pro Ala Asn
        115                 120                 125

Ser Lys Arg Pro Asn Gly Phe Val Asp Asn Ser Phe Leu Asp Ile Lys
    130                 135                 140

Arg Ile Arg Val Gly Glu Asn Leu Ser Ala Gly Gln Gly Gly Leu Gln
145                 150                 155                 160

Ile Asn Asn Gly Gln Ser Gln Ile Met Ser Gly Thr Leu Pro Met Ser
                165                 170                 175

Gln Ala Pro Leu Arg Lys Thr Asn Thr Leu Pro Ser His Thr His Ser
            180                 185                 190

Pro Gly Asn Gly Leu Phe Asn Met Gly Leu Lys Glu Val Lys Lys Glu
```

-continued

```
            195                 200                 205
Pro Gly Glu Thr Leu Ser Cys Ser Lys His Met Asp Gly Gln Met Thr
210                 215                 220

Gln Glu Asn Ile Phe Pro Asn Arg Tyr Gly Asp Asp Pro Gly Glu Gln
225                 230                 235                 240

Leu Met Asp Pro Glu Leu Gln Glu Leu Phe Asn Glu Leu Thr Asn Ile
                245                 250                 255

Ser Val Pro Pro Met Ser Asp Leu Glu Leu Glu Asn Met Ile Asn Ala
                260                 265                 270

Thr Ile Lys Gln Asp Asp Pro Phe Asn Ile Asp Leu Gly Gln Gln Ser
            275                 280                 285

Gln Arg Ser Thr Pro Arg Pro Ser Leu Pro Met Glu Lys Ile Val Ile
        290                 295                 300

Lys Ser Glu Tyr Ser Pro Gly Leu Thr Gln Gly Pro Ser Gly Ser Pro
305                 310                 315                 320

Gln Leu Arg Pro Pro Ser Ala Gly Pro Ala Phe Ser Met Ala Asn Ser
                325                 330                 335

Ala Leu Ser Thr Ser Ser Pro Ile Pro Ser Val Pro Gln Ser Gln Ala
                340                 345                 350

Gln Pro Gln Thr Gly Ser Gly Ala Ser Arg Ala Leu Pro Ser Trp Gln
            355                 360                 365

Glu Val Ser His Ala Gln Gln Leu Lys Gln Ile Ala Ala Asn Arg Gln
        370                 375                 380

Gln His Ala Arg Met Gln Gln His Gln Gln His Gln Pro Thr Asn
385                 390                 395                 400

Trp Ser Ala Leu Pro Ser Ser Ala Gly Pro Ser Pro Gly Pro Phe Gly
                405                 410                 415

Gln Glu Lys Ile Pro Ser Pro Ser Phe Gly Gln Thr Phe Ser Pro
                420                 425                 430

Gln Ser Ser Pro Met Pro Gly Val Ala Gly Gly Ser Gly Gln Ser Lys
            435                 440                 445

Val Met Ala Asn Tyr Met Tyr Lys Ala Gly Pro Ser Ala Gln Gly Gly
        450                 455                 460

His Leu Asp Val Leu Met Gln Gln Lys Pro Gln Asp Leu Ser Arg Ser
465                 470                 475                 480

Phe Ile Asn Asn Pro His Pro Ala Met Glu Pro Arg Gln Gly Asn Thr
                485                 490                 495

Lys Pro Leu Phe His Phe Asn Ser Asp Gln Ala Asn Gln Gln Met Pro
                500                 505                 510

Ser Val Leu Pro Ser Gln Asn Lys Pro Ser Leu Leu His Tyr Thr Gln
            515                 520                 525

Gln Gln Gln Gln Gln Gln Gln Gln Gln Gln Gln Gln Gln Gln Gln
        530                 535                 540

Gln Gln Gln Gln Gln Gln Gln Gln Gln Gln Gln Gln Gln Gln Gln Gln
545                 550                 555                 560

Gln Ser Ser Ile Ser Ala Gln Gln Gln Gln Gln Ser Ser Ile
                565                 570                 575

Ser Ala Gln Gln Gln Gln Gln Gln Gln Gln Gln Gln Gln Gln
                580                 585                 590

Gln Gln Gln Gln Gln Gln Gln Gln Gln Gln Gln Pro Ser Ser
            595                 600                 605

Gln Pro Ala Gln Ser Leu Pro Ser Gln Pro Leu Leu Arg Ser Pro Leu
            610                 615                 620
```

-continued

Pro Leu Gln Gln Lys Leu Leu Gln Gln Met Gln Asn Gln Pro Ile
625                 630                 635                 640

Ala Gly Met Gly Tyr Gln Val Ser Gln Gln Arg Gln Asp Gln His
            645                 650                 655

Ser Val Val Gly Gln Asn Thr Gly Pro Ser Pro Ser Pro Asn Pro Cys
                660                 665                 670

Ser Asn Pro Asn Thr Gly Ser Gly Tyr Met Asn Ser Gln Gln Ser Leu
        675                 680                 685

Leu Asn Gln Gln Leu Met Gly Lys Lys Gln Thr Leu Gln Arg Gln Ile
    690                 695                 700

Met Glu Gln Lys Gln Leu Leu Leu Gln Gln Met Leu Ala Asp
705                 710                 715                 720

Ala Glu Lys Ile Ala Pro Gln Asp Gln Ile Asn Arg His Leu Ser Arg
                725                 730                 735

Pro Pro Pro Asp Tyr Lys Asp Gln Arg Arg Asn Val Gly Asn Met Gln
            740                 745                 750

Pro Thr Ala Gln Tyr Ser Gly Gly Ser Ser Thr Ile Ser Leu Asn Ser
            755                 760                 765

Asn Gln Ala Leu Ala Asn Pro Val Ser Thr His Thr Ile Leu Thr Pro
770                 775                 780

Asn Ser Ser Leu Leu Ser Thr Ser His Gly Thr Arg Met Pro Ser Leu
785                 790                 795                 800

Ser Thr Ala Val Gln Asn Met Gly Met Tyr Gly Asn Leu Pro Cys Asn
            805                 810                 815

Gln Pro Asn Thr Tyr Ser Val Thr Ser Gly Met Asn Gln Leu Thr Gln
            820                 825                 830

Gln Arg Asn Pro Lys Gln Leu Leu Ala Asn Gln Asn Pro Met Met
        835                 840                 845

Pro Arg Pro Pro Thr Leu Gly Pro Ser Asn Asn Asn Asn Val Ala Thr
    850                 855                 860

Phe Gly Ala Gly Ser Val Gly Asn Ser Gln Gln Leu Arg Pro Asn Leu
865                 870                 875                 880

Thr His Ser Met Ala Ser Met Pro Pro Gln Arg Thr Ser Asn Val Met
            885                 890                 895

Ile Thr Ser Asn Thr Thr Ala Pro Asn Trp Ala Ser Gln Glu Gly Thr
            900                 905                 910

Ser Lys Gln Gln Glu Ala Leu Thr Ser Ala Gly Val Arg Phe Pro Thr
    915                 920                 925

Gly Thr Pro Ala Ala Tyr Thr Pro Asn Gln Ser Leu Gln Gln Ala Val
    930                 935                 940

Gly Ser Gln Gln Phe Ser Gln Arg Ala Val Ala Pro Pro Asn Gln Leu
945                 950                 955                 960

Thr Pro Ala Val Gln Met Arg Pro Met Asn Gln Met Ser Gln Thr Leu
            965                 970                 975

Asn Gly Gln Thr Met Gly Pro Leu Arg Gly Leu Asn Leu Arg Pro Asn
            980                 985                 990

Gln Leu Ser Thr Gln Ile Leu Pro Asn Leu Asn Gln Ser Gly Thr Gly
    995                 1000                1005

Leu Asn Gln Ser Arg Thr Gly Ile Asn Gln Pro Pro Ser Leu Thr
    1010                1015                1020

Pro Ser Asn Phe Pro Ser Pro Asn Gln Ser Ser Arg Ala Phe Gln
    1025                1030                1035

```
Gly Thr Asp His Ser Ser Asp Leu Ala Phe Asp Phe Leu Ser Gln
    1040                1045                1050

Gln Asn Asp Asn Met Gly Pro Ala Leu Asn Ser Asp Ala Asp Phe
    1055                1060                1065

Ile Asp Ser Leu Leu Lys Thr Glu Pro Gly Asn Asp Asp Trp Met
    1070                1075                1080

Lys Asp Ile Asn Leu Asp Glu Ile Leu Gly Asn Asn Ser
    1085                1090                1095

<210> SEQ ID NO 8
<211> LENGTH: 1133
<212> TYPE: PRT
<213> ORGANISM: Homo sapiens

<400> SEQUENCE: 8

Met Gly Asp Phe Ala Ala Pro Ala Ala Ala Asn Gly Ser Ser Ile
1               5                   10                  15

Cys Ile Asn Ser Ser Leu Asn Ser Ser Leu Gly Gly Ala Gly Ile Gly
            20                  25                  30

Val Asn Asn Thr Pro Asn Ser Thr Pro Ala Ala Pro Ser Ser Asn His
                35                  40                  45

Pro Ala Ala Gly Gly Cys Gly Gly Ser Gly Gly Pro Gly Gly Gly Ser
    50                  55                  60

Ala Ala Val Pro Lys His Ser Thr Val Val Glu Arg Leu Arg Gln Arg
65                  70                  75                  80

Ile Glu Gly Cys Arg Arg His His Val Asn Cys Glu Asn Arg Tyr Gln
                85                  90                  95

Gln Ala Gln Val Glu Gln Leu Glu Leu Glu Arg Arg Asp Thr Val Ser
            100                 105                 110

Leu Tyr Gln Arg Thr Leu Glu Gln Arg Ala Lys Lys Ser Gly Ala Gly
            115                 120                 125

Thr Gly Lys Gln Gln His Pro Ser Lys Pro Gln Gln Asp Ala Glu Ala
    130                 135                 140

Ala Ser Ala Glu Gln Arg Asn His Thr Leu Ile Met Leu Gln Glu Thr
145                 150                 155                 160

Val Lys Arg Lys Leu Glu Gly Ala Arg Ser Pro Leu Asn Gly Asp Gln
                165                 170                 175

Gln Asn Gly Ala Cys Asp Gly Asn Phe Ser Pro Thr Ser Lys Arg Ile
            180                 185                 190

Arg Lys Asp Ile Ser Ala Gly Met Glu Ala Ile Asn Asn Leu Pro Ser
        195                 200                 205

Asn Met Pro Leu Pro Ser Ala Ser Pro Leu His Gln Leu Asp Leu Lys
    210                 215                 220

Pro Ser Leu Pro Leu Gln Asn Ser Gly Thr His Thr Pro Gly Leu Leu
225                 230                 235                 240

Glu Asp Leu Ser Lys Asn Gly Arg Leu Pro Glu Ile Lys Leu Pro Val
                245                 250                 255

Asn Gly Cys Ser Asp Leu Glu Asp Ser Phe Thr Ile Leu Gln Ser Lys
            260                 265                 270

Asp Leu Lys Gln Glu Pro Leu Asp Asp Pro Thr Cys Ile Asp Thr Ser
        275                 280                 285

Glu Thr Ser Leu Ser Asn Gln Asn Lys Leu Phe Ser Asp Ile Asn Leu
    290                 295                 300

Asn Asp Gln Glu Trp Gln Glu Leu Ile Asp Glu Leu Ala Asn Thr Val
305                 310                 315                 320
```

```
Pro Glu Asp Asp Ile Gln Asp Leu Phe Asn Glu Asp Phe Glu Glu Lys
                    325                 330                 335
Lys Glu Pro Glu Phe Ser Gln Pro Ala Thr Glu Thr Pro Leu Ser Gln
                340                 345                 350
Glu Ser Ala Ser Val Lys Ser Asp Pro Ser His Ser Pro Phe Ala His
            355                 360                 365
Val Ser Met Gly Ser Pro Gln Ala Arg Pro Ser Ser Gly Pro Pro
        370                 375                 380
Phe Ser Thr Val Ser Thr Ala Thr Ser Leu Pro Ser Val Ala Ser Thr
385                 390                 395                 400
Pro Ala Ala Pro Asn Pro Ala Ser Ser Pro Ala Asn Cys Ala Val Gln
                405                 410                 415
Ser Pro Gln Thr Pro Asn Gln Ala His Thr Pro Gly Gln Ala Pro Pro
                420                 425                 430
Arg Pro Gly Asn Gly Tyr Leu Leu Asn Pro Ala Ala Val Thr Val Ala
                435                 440                 445
Gly Ser Ala Ser Gly Pro Val Ala Val Pro Ser Ser Asp Met Ser Pro
            450                 455                 460
Ala Glu Gln Leu Lys Gln Met Ala Ala Gln Gln Gln Arg Ala Lys
465                 470                 475                 480
Leu Met Gln Gln Lys Gln Gln Gln Gln Gln Gln Gln Gln Gln Gln Gln
                485                 490                 495
Gln Gln Gln Gln Gln Gln Gln Gln Gln His Ser Asn Gln Thr Ser
            500                 505                 510
Asn Trp Ser Pro Leu Gly Pro Pro Ser Ser Pro Tyr Gly Ala Ala Phe
    515                 520                 525
Thr Ala Glu Lys Pro Asn Ser Pro Met Met Tyr Pro Gln Ala Phe Asn
    530                 535                 540
Asn Gln Asn Pro Ile Val Pro Pro Met Ala Asn Asn Leu Gln Lys Thr
545                 550                 555                 560
Thr Met Asn Asn Tyr Leu Pro Gln Asn His Met Asn Met Ile Asn Gln
                565                 570                 575
Gln Pro Asn Asn Leu Gly Thr Asn Ser Leu Asn Lys Gln His Asn Ile
                580                 585                 590
Leu Thr Tyr Gly Asn Thr Lys Pro Leu Thr His Phe Asn Ala Asp Leu
            595                 600                 605
Ser Gln Arg Met Thr Pro Pro Val Ala Asn Pro Asn Lys Asn Pro Leu
    610                 615                 620
Met Pro Tyr Ile Gln Gln Gln Gln Gln Gln Gln Gln Gln Gln Gln Gln
625                 630                 635                 640
Gln Gln Gln Gln Gln Gln Pro Pro Pro Gln Leu Gln Ala Pro Arg
                645                 650                 655
Ala His Leu Ser Glu Asp Gln Lys Arg Leu Leu Leu Met Lys Gln Lys
                660                 665                 670
Gly Val Met Asn Gln Pro Met Ala Tyr Ala Ala Leu Pro Ser His Gly
            675                 680                 685
Gln Glu Gln His Pro Val Gly Leu Pro Arg Thr Thr Gly Pro Met Gln
    690                 695                 700
Ser Ser Val Pro Pro Gly Ser Gly Gly Met Val Ser Gly Ala Ser Pro
705                 710                 715                 720
Ala Gly Pro Gly Phe Leu Gly Ser Gln Pro Gln Ala Ala Ile Met Lys
                725                 730                 735
```

```
Gln Met Leu Ile Asp Gln Arg Ala Gln Leu Ile Glu Gln Gln Lys Gln
             740                 745                 750

Gln Phe Leu Arg Glu Gln Arg Gln Gln Gln Gln Gln Gln Gln Gln Ile
             755                 760                 765

Leu Ala Glu Gln Gln Leu Gln Gln Ser His Leu Pro Arg Gln His Leu
             770                 775                 780

Gln Pro Gln Arg Asn Pro Tyr Pro Val Gln Gln Val Asn Phe Gln
785              790                 795                 800

Gly Ser Pro Gln Asp Ile Ala Ala Val Arg Ser Gln Ala Ala Leu Gln
             805                 810                 815

Ser Met Arg Thr Ser Arg Leu Met Ala Gln Asn Ala Gly Met Met Gly
             820                 825                 830

Ile Gly Pro Ser Gln Asn Pro Gly Thr Met Ala Thr Ala Ala Gln
             835                 840                 845

Ser Glu Met Gly Leu Ala Pro Tyr Ser Thr Thr Pro Thr Ser Gln Pro
             850                 855                 860

Gly Met Tyr Asn Met Ser Thr Gly Met Thr Gln Met Leu Gln His Pro
865              870                 875                 880

Asn Gln Ser Gly Met Ser Ile Thr His Asn Gln Ala Gln Gly Pro Arg
             885                 890                 895

Gln Pro Ala Ser Gly Gln Gly Val Gly Met Val Ser Gly Phe Gly Gln
             900                 905                 910

Ser Met Leu Val Asn Ser Ala Ile Thr Gln His Pro Gln Met Lys
             915                 920                 925

Gly Pro Val Gly Gln Ala Leu Pro Arg Pro Gln Ala Pro Pro Arg Leu
             930                 935                 940

Gln Ser Leu Met Gly Thr Val Gln Gln Gly Ala Gln Ser Trp Gln Gln
945              950                 955                 960

Arg Ser Leu Gln Gly Met Pro Gly Arg Thr Ser Gly Glu Leu Gly Pro
             965                 970                 975

Phe Asn Asn Gly Ala Ser Tyr Pro Leu Gln Ala Gly Pro Arg Leu
             980                 985                 990

Thr Lys Gln His Phe Pro Gln Gly Leu Ser Gln Ser Val Val Asp Ala
             995                1000                1005

Asn Thr Gly Thr Val Arg Thr Leu Asn Pro Ala Ala Met Gly Arg
             1010                1015                1020

Gln Met Met Pro Ser Leu Pro Gly Gln Gln Gly Thr Ser Gln Ala
             1025                1030                1035

Arg Pro Met Val Met Ser Gly Leu Ser Gln Gly Val Pro Gly Met
             1040                1045                1050

Pro Ala Phe Ser Gln Pro Ala Gln Gln Gln Ile Pro Ser Gly
             1055                1060                1065

Ser Phe Ala Pro Ser Ser Gln Ser Gln Ala Tyr Glu Arg Asn Ala
             1070                1075                1080

Pro Gln Asp Val Ser Tyr Asn Tyr Ser Gly Asp Gly Ala Gly Gly
             1085                1090                1095

Ser Phe Pro Gly Leu Pro Asp Gly Ala Asp Leu Val Asp Ser Ile
             1100                1105                1110

Ile Lys Gly Gly Pro Gly Asp Glu Trp Met Gln Glu Leu Asp Glu
             1115                1120                1125

Leu Phe Gly Asn Pro
             1130
```

<210> SEQ ID NO 9
<211> LENGTH: 62
<212> TYPE: PRT
<213> ORGANISM: Artificial Sequence
<220> FEATURE:
<223> OTHER INFORMATION: dnMAML(13-74)

<400> SEQUENCE: 9

Leu Pro Arg His Ser Ala Val Met Glu Arg Leu Arg Arg Arg Ile Glu
1               5                   10                  15

Leu Cys Arg Arg His His Ser Thr Cys Glu Ala Arg Tyr Glu Ala Val
                20                  25                  30

Ser Pro Glu Arg Leu Glu Leu Glu Arg Gln His Thr Phe Ala Leu His
            35                  40                  45

Gln Arg Cys Ile Gln Ala Lys Ala Lys Arg Ala Gly Lys His
        50                  55                  60

<210> SEQ ID NO 10
<211> LENGTH: 127
<212> TYPE: PRT
<213> ORGANISM: Artificial Sequence
<220> FEATURE:
<223> OTHER INFORMATION: ANTP-dnMAML conjugate

<400> SEQUENCE: 10

Arg Lys Arg Gly Arg Gln Thr Tyr Thr Arg Tyr Gln Thr Leu Glu Leu
1               5                   10                  15

Glu Lys Glu Phe His Phe Asn Arg Tyr Leu Thr Arg Arg Arg Arg Ile
                20                  25                  30

Glu Ile Ala His Ala Leu Cys Leu Thr Glu Arg Gln Ile Lys Ile Trp
            35                  40                  45

Phe Gln Asn Arg Arg Met Lys Trp Lys Lys Glu Asn Gly Glu Phe Met
        50                  55                  60

Ala Leu Pro Arg His Ser Ala Val Met Glu Arg Leu Arg Arg Arg Ile
65                  70                  75                  80

Glu Leu Cys Arg Arg His His Ser Thr Cys Glu Ala Arg Tyr Glu Ala
                85                  90                  95

Val Ser Pro Glu Arg Leu Glu Leu Glu Arg Gln His Thr Phe Ala Leu
            100                 105                 110

His Gln Arg Cys Ile Gln Ala Lys Ala Lys Arg Ala Gly Lys His
        115                 120                 125

<210> SEQ ID NO 11
<211> LENGTH: 85
<212> TYPE: PRT
<213> ORGANISM: Artificial Sequence
<220> FEATURE:
<223> OTHER INFORMATION: penetratin-dnMAML conjugate

<400> SEQUENCE: 11

Arg Gln Ile Lys Ile Trp Phe Gln Asn Arg Arg Met Lys Trp Lys Lys
1               5                   10                  15

Glu Asn Gly Glu Phe Met Ala Leu Pro Arg His Ser Ala Val Met Glu
                20                  25                  30

Arg Leu Arg Arg Arg Ile Glu Leu Cys Arg Arg His His Ser Thr Cys
            35                  40                  45

Glu Ala Arg Tyr Glu Ala Val Ser Pro Glu Arg Leu Glu Leu Glu Arg
        50                  55                  60

Gln His Thr Phe Ala Leu His Gln Arg Cys Ile Gln Ala Lys Ala Lys
65                  70                  75                  80

Arg Ala Gly Lys His
                85

<210> SEQ ID NO 12
<211> LENGTH: 136
<212> TYPE: PRT
<213> ORGANISM: Artificial Sequence
<220> FEATURE:
<223> OTHER INFORMATION: His-ANTP-dnMAML conjugate (Syntana-4)

<400> SEQUENCE: 12

Met His His His His His Gly Ser Arg Lys Arg Gly Arg Gln Thr
1               5                   10                  15

Tyr Thr Arg Tyr Gln Thr Leu Glu Leu Glu Lys Glu Phe His Phe Asn
                20                  25                  30

Arg Tyr Leu Thr Arg Arg Arg Ile Glu Ile Ala His Ala Leu Cys
        35                  40                  45

Leu Thr Glu Arg Gln Ile Lys Ile Trp Phe Gln Asn Arg Arg Met Lys
    50                  55                  60

Trp Lys Lys Glu Asn Gly Glu Phe Met Ala Leu Pro Arg His Ser Ala
65                  70                  75                  80

Val Met Glu Arg Leu Arg Arg Arg Ile Glu Leu Cys Arg Arg His His
                85                  90                  95

Ser Thr Cys Glu Ala Arg Tyr Glu Ala Val Ser Pro Glu Arg Leu Glu
                100                 105                 110

Leu Glu Arg Gln His Thr Phe Ala Leu His Gln Arg Cys Ile Gln Ala
            115                 120                 125

Lys Ala Lys Arg Ala Gly Lys His
        130                 135

<210> SEQ ID NO 13
<211> LENGTH: 12
<212> TYPE: PRT
<213> ORGANISM: Artificial Sequence
<220> FEATURE:
<223> OTHER INFORMATION: HIV-TAT

<400> SEQUENCE: 13

Gly Arg Lys Lys Arg Arg Gln Arg Arg Arg Pro Gln
1               5                   10

<210> SEQ ID NO 14
<211> LENGTH: 27
<212> TYPE: PRT
<213> ORGANISM: Artificial Sequence
<220> FEATURE:
<223> OTHER INFORMATION: MPG

<400> SEQUENCE: 14

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 15
<211> LENGTH: 21
<212> TYPE: PRT
<213> ORGANISM: Artificial Sequence
<220> FEATURE:
<223> OTHER INFORMATION: PEP-1

<400> SEQUENCE: 15

```
Lys Glu Thr Trp Trp Glu Thr Trp Trp Thr Glu Trp Ser Gln Pro Lys
1               5                   10                  15

Lys Lys Arg Lys Cys
            20
```

<210> SEQ ID NO 16
<211> LENGTH: 23
<212> TYPE: PRT
<213> ORGANISM: Artificial Sequence
<220> FEATURE:
<223> OTHER INFORMATION: EB1

<400> SEQUENCE: 16

```
Leu Ile Lys Leu Trp Ser His Leu Ile His Ile Trp Phe Gln Asn Arg
1               5                   10                  15

Arg Leu Lys Trp Lys Lys Lys
            20
```

<210> SEQ ID NO 17
<211> LENGTH: 26
<212> TYPE: PRT
<213> ORGANISM: Artificial Sequence
<220> FEATURE:
<223> OTHER INFORMATION: Transportan

<400> SEQUENCE: 17

```
Trp Thr Leu Asn Ser Ala Gly Tyr Leu Leu Gly Lys Ile Asn Leu Lys
1               5                   10                  15

Ala Leu Ala Ala Leu Ala Lys Lys Ile Leu
            20                  25
```

<210> SEQ ID NO 18
<211> LENGTH: 15
<212> TYPE: PRT
<213> ORGANISM: Artificial Sequence
<220> FEATURE:
<223> OTHER INFORMATION: hCT(18-32)

<400> SEQUENCE: 18

```
Lys Phe His Thr Phe Pro Gln Thr Ala Ile Gly Val Gly Ala Pro
1               5                   10                  15
```

<210> SEQ ID NO 19
<211> LENGTH: 18
<212> TYPE: PRT
<213> ORGANISM: Artificial Sequence
<220> FEATURE:
<223> OTHER INFORMATION: KLA

<400> SEQUENCE: 19

```
Lys Leu Ala Leu Lys Leu Ala Leu Lys Ala Leu Lys Ala Ala Leu Lys
1               5                   10                  15

Leu Ala
```

<210> SEQ ID NO 20
<211> LENGTH: 9
<212> TYPE: PRT
<213> ORGANISM: Artificial Sequence
<220> FEATURE:
<223> OTHER INFORMATION: AGR

<400> SEQUENCE: 20

```
Cys Ala Gly Arg Arg Ser Ala Tyr Cys
1               5
```

```
<210> SEQ ID NO 21
<211> LENGTH: 9
<212> TYPE: PRT
<213> ORGANISM: Artificial Sequence
<220> FEATURE:
<223> OTHER INFORMATION: LyP-2

<400> SEQUENCE: 21

Cys Asn Arg Arg Thr Lys Ala Gly Cys
1               5

<210> SEQ ID NO 22
<211> LENGTH: 9
<212> TYPE: PRT
<213> ORGANISM: Artificial Sequence
<220> FEATURE:
<223> OTHER INFORMATION: REA

<400> SEQUENCE: 22

Cys Arg Glu Ala Gly Arg Lys Ala Cys
1               5

<210> SEQ ID NO 23
<211> LENGTH: 9
<212> TYPE: PRT
<213> ORGANISM: Artificial Sequence
<220> FEATURE:
<223> OTHER INFORMATION: LSD

<400> SEQUENCE: 23

Cys Leu Ser Asp Gly Lys Arg Lys Cys
1               5

<210> SEQ ID NO 24
<211> LENGTH: 12
<212> TYPE: PRT
<213> ORGANISM: Artificial Sequence
<220> FEATURE:
<223> OTHER INFORMATION: HN-1

<400> SEQUENCE: 24

Thr Ser Pro Leu Asn Ile His Asn Gly Gln Lys Leu
1               5                   10

<210> SEQ ID NO 25
<211> LENGTH: 12
<212> TYPE: PRT
<213> ORGANISM: Artificial Sequence
<220> FEATURE:
<223> OTHER INFORMATION: CTP

<400> SEQUENCE: 25

Ala Pro Trp His Leu Ser Ser Gln Tyr Ser Arg Thr
1               5                   10

<210> SEQ ID NO 26
<211> LENGTH: 12
<212> TYPE: PRT
<213> ORGANISM: Artificial Sequence
<220> FEATURE:
<223> OTHER INFORMATION: HAP-1

<400> SEQUENCE: 26

Ser Phe His Gln Phe Ala Arg Ala Thr Leu Ala Ser
1               5                   10
```

```
<210> SEQ ID NO 27
<211> LENGTH: 12
<212> TYPE: PRT
<213> ORGANISM: Artificial Sequence
<220> FEATURE:
<223> OTHER INFORMATION: 239P-1

<400> SEQUENCE: 27

Ser Asn Asn Asn Val Arg Pro Ile His Ile Trp Pro
1               5                   10

<210> SEQ ID NO 28
<211> LENGTH: 5
<212> TYPE: PRT
<213> ORGANISM: Artificial Sequence
<220> FEATURE:
<223> OTHER INFORMATION: connecting peptide

<400> SEQUENCE: 28

Gly Glu Phe Met Ala
1               5
```

PEPTIDE CONJUGATES

CROSS-REFERENCE TO RELATED APPLICATION

This application is the US national stage of PCT/GB2018/052413 filed Aug. 24, 2018, which claims priority to GB 1713700.1 filed Aug. 25, 2017.

REFERENCE TO A SEQUENCE LISTING

This application includes an electronic sequence listing in a file named 544281SEQLST.TXT, created on Feb. 21, 2020, and containing 38,570 bytes, which is hereby incorporated by reference in its entirety for all purposes.

FIELD OF THE INVENTION

The present invention relates to peptide conjugates capable of translocating across the cytoplasmic membrane of a mammalian cell and inhibiting the Notch signalling pathway. In particular, the invention relates to peptide conjugates that comprise a first region derived from Antennapedia (ANTP) homeodomain and a second region derived from the Mastermind-like (MAML) protein. The invention also relates to the use of such peptide conjugates to treat cancer. In particular, the invention relates to the use of the peptide conjugates to target chemo-resistant cancer cells and cancer stem cells (CSCs).

BACKGROUND OF THE INVENTION

Populations of tumour cells display variability in their phenotypic and genotypic traits. For example, many tumour cells are immune cells (e.g. macrophages), endothelial cells, or other terminally differentiated cell types. Only a small proportion of tumour cells are capable of initiating tumorigenesis. In many different types of malignancy, these "tumour-initiating" cells have been shown to display the stem-like properties of somatic stem cells, including the ability to undergo self-renewal, differentiation and possess relative resistance, similar to normal stem cells, against noxious stimuli such as chemotherapy. Tumour-initiating cells, otherwise collectively known as cancer stem cells (CSCs), are believed to drive tumour growth, disease progression, and metastasis. Although CSCs were initially discovered in leukemia, there is now extensive evidence that CSCs also exist in the majority of solid tumours, including tumours from the breast, pancreas, prostate, colon, stomach and brain.

Current models indicate that CSCs are organised into tree-like hierarchies. At the top of the hierarchy resides an "apex" CSC. These cells can enter a highly proliferative state, resulting in the production of a population of lower potency progenitor CSCs. Progenitor CSCs then undergo extensive asymmetric cell divisions to produce mature, differentiated cell types that form the bulk of the tumour. The apex CSC meanwhile enters a quiescent state.

Current radiotherapy, chemotherapy, hormonal therapy, and immunotherapy could eliminate the bulk of cancer cells, but often fail to eliminate all cancer cells including the critical CSCs (FIG. 1), which are protected by endogenous and specific resistance mechanisms related to stemness mechanisms such as the Notch pathway. Surviving CSCs give rise to new and more aggressive tumours and metastases, causing relapse of the disease and demise of the patient. The recurrent tumours tend to be more 'stem cell-like', aggressive, metastasizing, and resistant to conventional therapies. These characteristics lead to worse prognosis and outlook for the patient. Thus, the survival and emergence of CSCs could explain the failure of current cancer therapies. This could highlight a new direction for novel and improved cancer therapy which targets both cancer cells and CSCs.

The Notch signalling pathway is primarily thought to regulate stem cell self-renewal and differentiation during embryonic development. However, overwhelming evidence now indicates that Notch signalling also plays a role in carcinogenesis and tumour progression. For example, constitutive activation of the Notch signalling pathway has been reported in 60% of T-cell acute lymphoblastic leukemia (T-ALL). Increased Notch signalling also plays an important role in the etiology of breast cancer, and inhibition of Notch signalling reverts the transformed phenotype of breast cancer cell lines and prevents growth of primary tumor cells. Thus, manipulation of Notch signalling is considered a viable approach to target CSCs and inhibit tumour progression in Notch mutated tumours (FIG. 2).

Canonical Notch signalling is initiated by the binding of a membrane-bound ligand to a Notch receptor embedded in the membrane of an adjacent cell. Known mammalian Notch ligands include Jagged 1, Jagged 2, Delta-like 1, Delta-like 3, and Delta-like 4. The mammalian Notch family of receptors meanwhile comprises four members (Notch1, Notch2, Notch3, and Notch4). Notch ligands and receptors are highly conserved; Notch1, Notch2, Notch3, and Notch4 share approximately 60% sequence identity to each other and their *Drosophila* orthologue (FIG. 2).

Notch receptors are single pass transmembrane proteins. They therefore comprise an extracellular domain (NECD), a transmembrane domain (NTMD), and an intracellular domain (NICD). Prior to ligand presentation, Notch receptors are held in an autoinhibitory state and are marked for ubiquitin-mediated degradation. Upon interaction between cognate receptors on adjacent cells, Notch receptors undergo two consecutive proteolytic cleavages. The first cleavage, catalysed by metalloproteases of the ADAM (A Disintegrin and Metalloprotease) family, releases the Notch ectodomain. The resulting membrane-tethered intermediate is a substrate for the γ-secretase multiprotein enzyme complex. Subsequent proteolysis liberates the NICD from the cytoplasmic side of the plasma membrane. The liberated NICD is then able to translocate to the nucleus.

The NICD is unable to bind DNA and activate the transcription of Notch target genes unaided. Instead, NICD complexes with a transcription factor known as Core Binding Factor 1 (CBF-1). Formation of the NICD-CBF-1 complex displaces a number of co-repressors from CBF-1 and therefore acts as a transcriptional switch. Cooperative assembly of the Notch transcription complex additionally relies on recruitment of a coactivator; mastermind-like (MAML) protein. MAML binds to a groove formed at the interface of the NICD-CBF-1 complex and recruit other co-activator proteins, including p300 and components of the mediator complex, by virtue of a low complexity C-terminal domain.

Truncated MAML mutants consisting of only the N-terminal NICD-CBF-1 binding domain are potent inhibitors of Notch signalling. For example, dnMAML (13 to 74) is sufficient for the formation of a stable, transcriptionally inert NICD/CBF-1/MAML1 ternary complex, thereby inhibiting Notch signalling activation by all four mammalian Notch receptors. Dominant negative MAML (dnMAML) and variants thereof may therefore be used to target the Notch signalling pathway to treat cancer.

Therapeutic peptides which target intracellular proteins must first traverse the biological membrane. Hence, engineering peptides able to access intracellular targets is challenging. A potentially promising strategy for producing cell-penetrating therapeutic peptides involves fusing the therapeutic moiety to a peptide capable of a traversing cell membrane. A number of naturally occurring, cell penetrating peptides (CPPs) are known. The ANTP homeodomain, for example, has been used to internalise a number of functional and regulatory proteins. Due to its large size (60 amino acid residues), the ANTP homeodomain may be capable of internalising larger cargo or therapeutic moieties than other CPPs, and more efficiently than penetratin alone [Wu A and Gerhing W (2014) Biochem Biophys Res Commun 443, 1136-1149]. Therapeutic ANTP-conjugates may therefore be used in medical applications. However, such conjugates would need to retain the cell-penetrating ability of the CPP moiety and retain the therapeutic effect of the therapeutic moiety.

In practice, it has been found that recombinant production of ANTP-fusion proteins is technically challenging. The success of recombinant technology is known to be limited by poor growth of the host, inclusion body (IB) formation, protein inactivity, and low yields. In particular, the recombinant ANTP-fusion proteins described herein formed aggregates. Despite using a number of denaturation-folding strategies, portions of the ANTP-fusion proteins remained misfolded and, when in contact with a cell, were toxic. Furthermore, it can be very difficult to produce functional fusion proteins recombinantly at scalable yields that can be clinically or commercially exploited.

The present invention is directed to peptide conjugates of a CPP and a Notch signalling inhibitor, which conjugates surprisingly preserve the function and stability of the CPP and the Notch inhibitory functions. The peptides may be synthesised in vitro using, for example, solid-phase peptide synthesis.

BRIEF SUMMARY OF THE INVENTION

The present application is directed to novel therapeutic peptide conjugates, which comprise the Antennapedia (ANTP) homeodomain or a variant thereof and dominant-negative Mastermind-like (MAML) peptide. Such peptides can be synthesised using solid-phase peptide synthesis and a simple reconstitution method that does not involve refolding buffers or complex procedures. Yields of the peptide are high (i.e. greater than 90%), suggesting that the conjugate may be produced in quantities large enough to be of therapeutic benefit. Furthermore, compared to alternative therapeutic conjugates comprising dnMAML, a peptide conjugate of the invention, such as Syntana-4, may have improved solubility and/or in vivo potency.

Accordingly, the invention provides a peptide conjugate comprising: (a) a first region comprising a cell-penetrating peptide of SEQ ID NO:4 or a homolog having at least 80% sequence identity thereto; conjugated to (b) a second region comprising a peptide that is an inhibitor of the Notch signalling pathway and is of SEQ ID NO:9 or a homolog thereof having at least 80% sequence identity thereto; and (c) a connecting peptide between the first and the second region that is from 2 to 10 amino acids in length.

In some embodiments, the conjugate is capable of translocation across the cytoplasmic membrane of a mammalian cell and inhibiting the Notch signalling pathway.

In some embodiments, the first region comprises a cell-penetrating peptide of SEQ ID NO:2, or a homolog having at least 80% sequence identity thereto.

In some embodiments, the conjugate of the invention comprises a first region comprising a cell penetrating peptide of SEQ ID NO:2 or SEQ ID NO:3. In some embodiments, the conjugate of the invention comprises cell penetrating peptide of SEQ ID NO:2.

In some embodiments, the conjugate of the invention comprises an inhibitor of the Notch signalling pathway defined by SEQ ID NO:9 or a variant according to the sequence:

LPRHSAVMERLRRRIELCRRHHSTCEARYEAVSPERLELERQHTFALHQ

RCIQAKAKRAGKH and wherein the underlined residues are conserved and none, one, two, three, four, five or up to 15 of the other residues are replaced by conservative substitutions.

In some embodiments, the conjugate of the invention comprises an inhibitor of the Notch signalling pathway defined by SEQ ID NO:9.

In some embodiments of the invention, the connecting peptide is two to seven amino acids long. In some embodiments, the connecting peptide comprises an amino acid selected from the group G, E, F, M or A. In some embodiments, the connecting peptide is the amino acid sequence GEFMA (SEQ ID NO:28).

In a further embodiment, the conjugate comprises or is SEQ ID NO:12 (Syntana-4) In a further embodiment, the conjugate comprises or is SEQ ID NO:10.

The invention also provides a pharmaceutical composition comprising a conjugate of the invention and a pharmaceutically acceptable carrier. The invention also provides a conjugate of the invention for use in a method of treatment of the human or animal body by therapy. In some embodiments, the conjugate or pharmaceutical composition of the invention is for use in a method of treating cancer or inhibiting Notch signalling in cancer stem cells or progenitor cells. In some embodiments, the conjugate or pharmaceutical composition of the invention is for use in a method comprising co-administration or sequential administration of the conjugate or composition with a chemotherapeutic drug. In some embodiments, the conjugate or pharmaceutical composition of the invention is for use in the manufacture of a medicament for treating cancer or inhibiting Notch signalling in cancer stem cells or progenitor cells. Also provided is a method of treating cancer or inhibiting Notch signalling in cancer stem cells or progenitor cells, comprising administering a conjugate or pharmaceutical composition of the invention.

Also provided is a kit comprising a conjugate or pharmaceutical composition of the invention, and one or more additional therapeutic agents suitable for simultaneous administration, sequential administration or separate administration.

It is also to be understood that the terminology used herein is for purposes of describing particular embodiments only, and is not intended to be limiting. The scope of the present invention will be limited only in the appended claims.

BRIEF DESCRIPTION OF THE DRAWINGS

FIG. 6 Mammalian expression of recombinant ANTP-dnMAML conjugate is non-viable:
Anti-HIS Western blot of *E. coli* recombinant ANTP-dnMAML (prepared according to Example 1) and (Live) cell extract (no TR4 present) and (Debris) small amount of recombinant ANTP-dnMAML present after CHO transfected mammalian cell culture.

FIG. 7 In vivo efficacy studies showing that recombinant ANTP/DN-MAML is less potent than Syntana-4 in nude mouse xenograft models FIG. 8 Synthesis and characterisation of Syntana-4 'prefolded' peptide FIG. 9 CD Analyses of Syntana-4

FIG. 10 Concentration of Syntana-4

FIG. 11 3D structure of ANTP. Cysteine residue labelled with dashed arrow, lysines with bold arrow and arginine residues with arrows.

The structure was generated using data was from Qian et al. Proc Natl Acad Sci USA. 1994 Apr. 26; 91(9): 4091-5 and Swiss PDB viewer.

Figure 12:
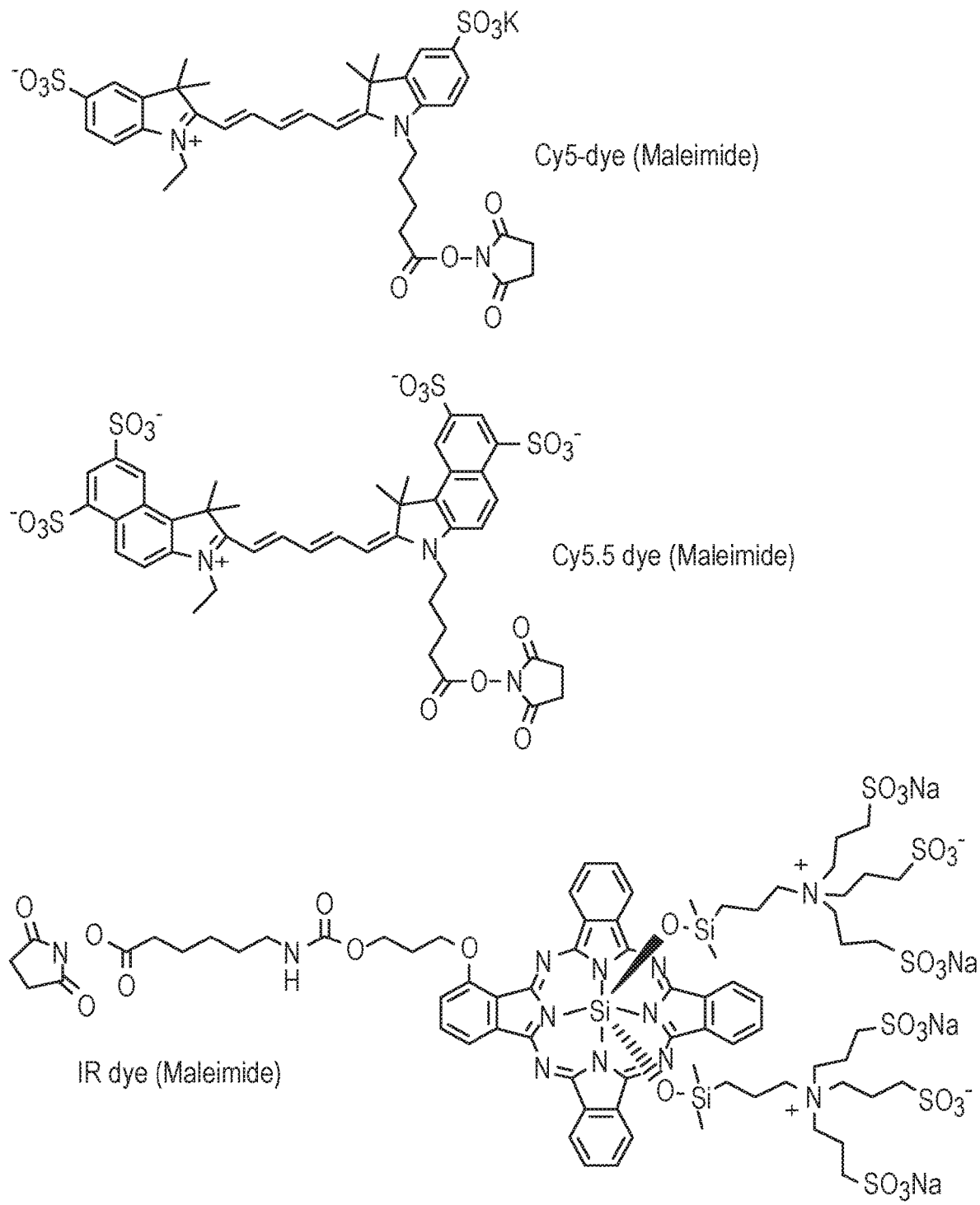
Figure 13A:
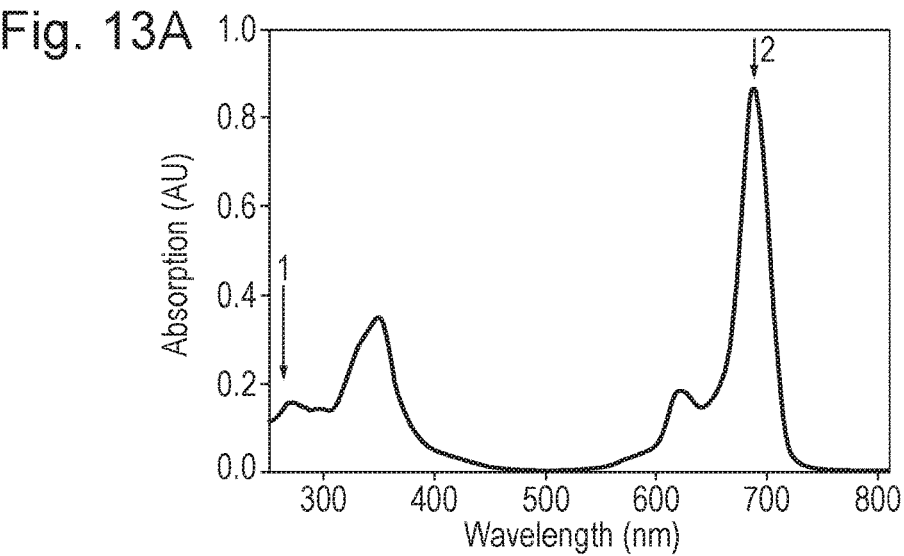
Figure 13B:
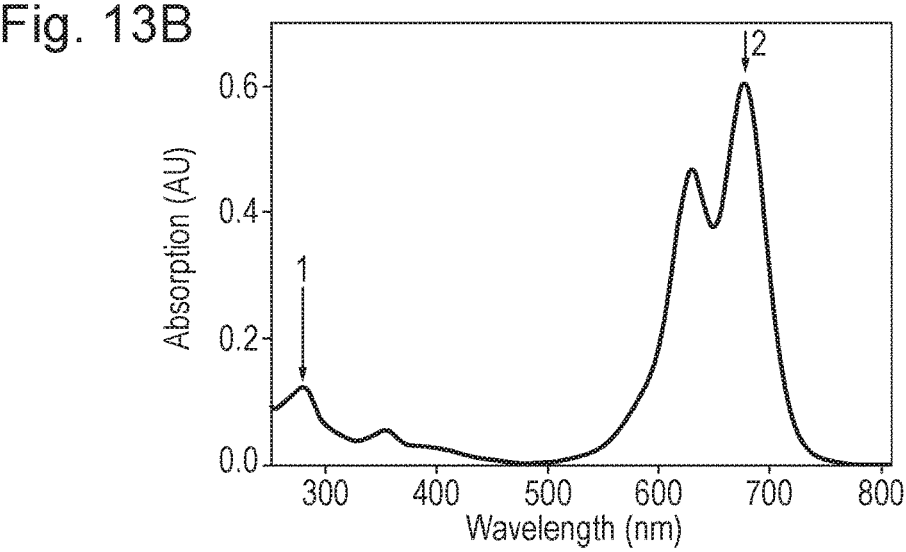
Figure 13C:
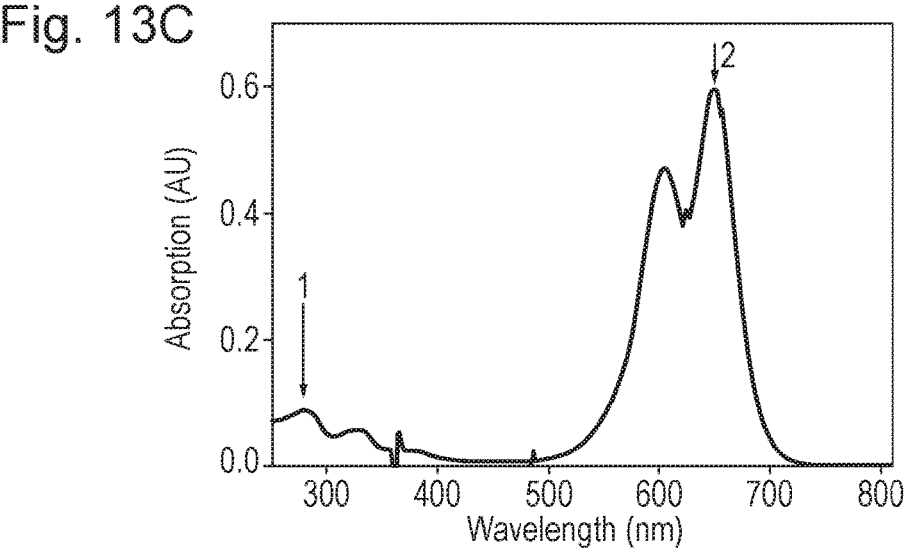
Figure 13D:
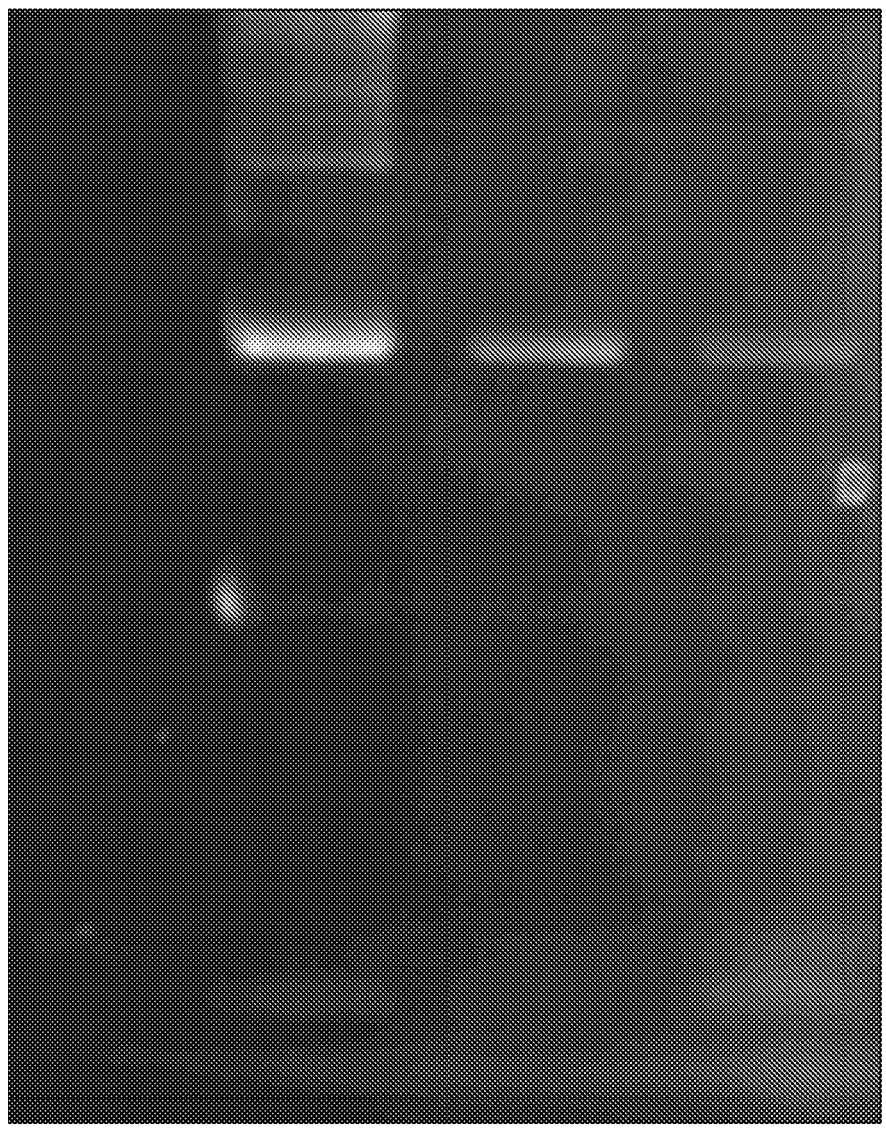

FIG. 12 Commercially-available dyes used to conjugate onto Syntana-4

Figure 14A:
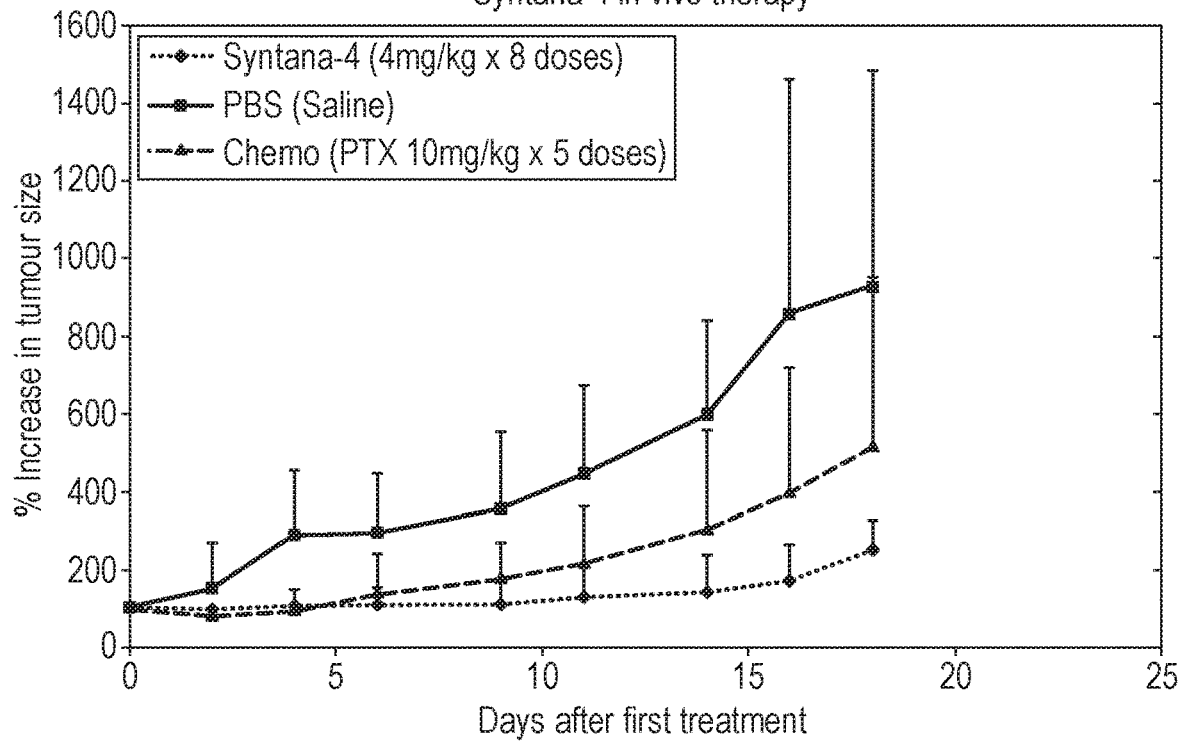
Figure 14B:
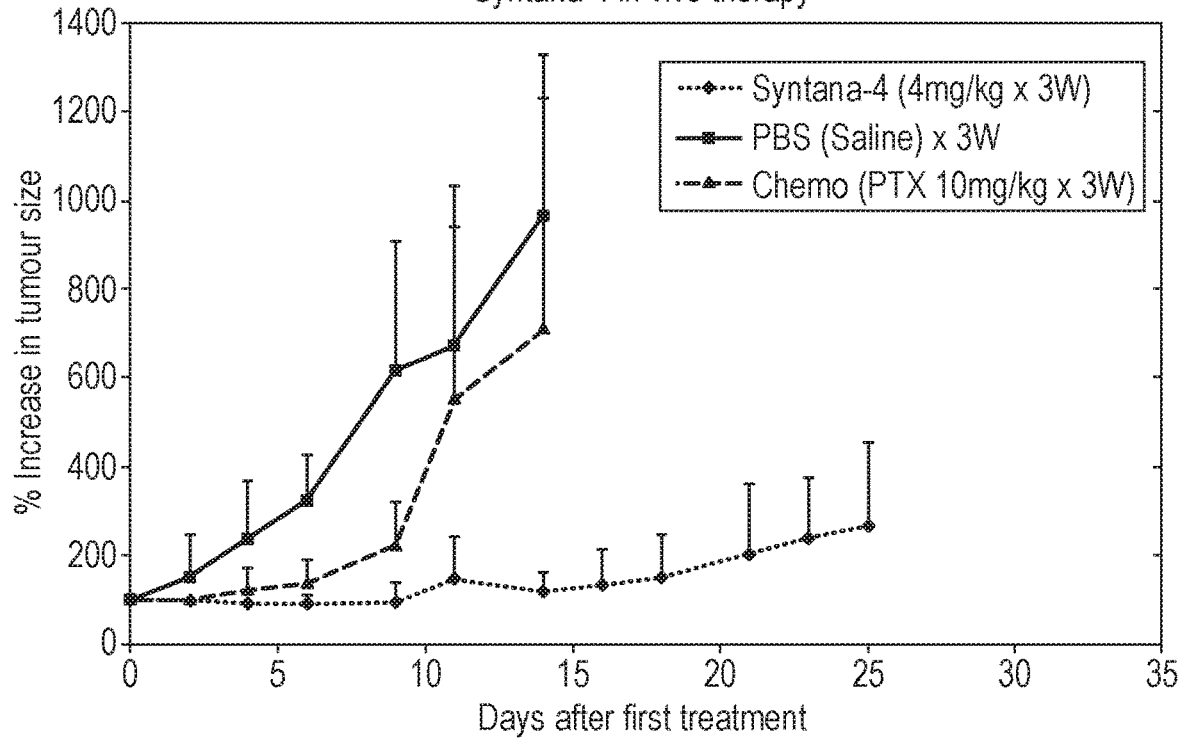
Figure 15:
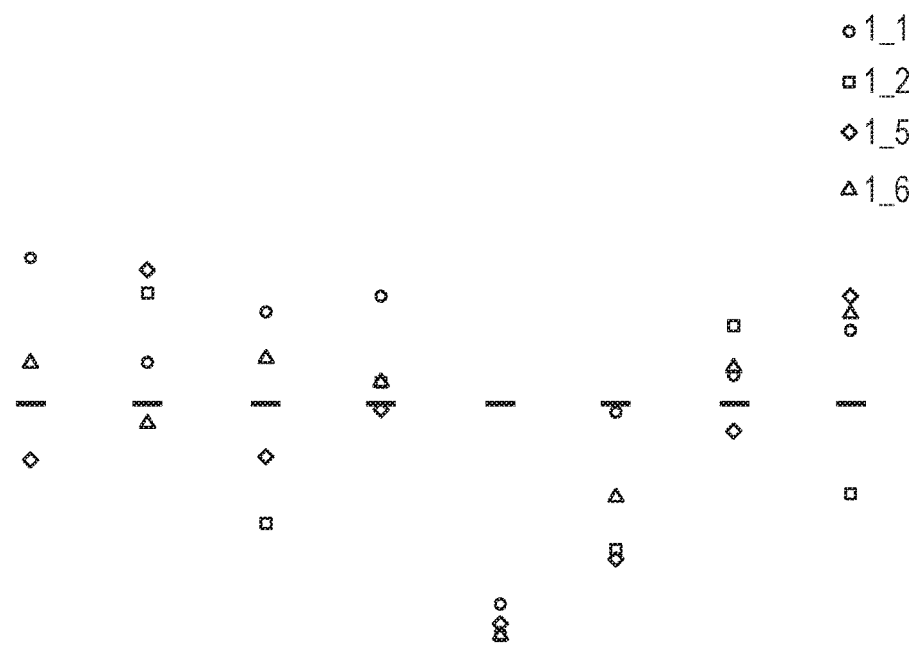

FIG. 13 Conjugated Syntana-4 fluorescence spectra
- (A) Syntana-4-IR dye spectra
- (B) Syntana-4-Cy5 dye spectra
- (C) Syntana-4-Cy5.5 dye spectra.
- (D) SDS PAGE gels FIG. 14 Two examples of in vivo efficacy studies showing that Syntana-4 causes significant tumour growth delays in nude mouse xenograft models of MDA-MB-231 tumours FIG. 15 RT-Quantitative-PCR
Upper panel shows the relative expression of mRNA for various NOTCH-related genes and the lower panel is a graphical representation.

Figure 16:
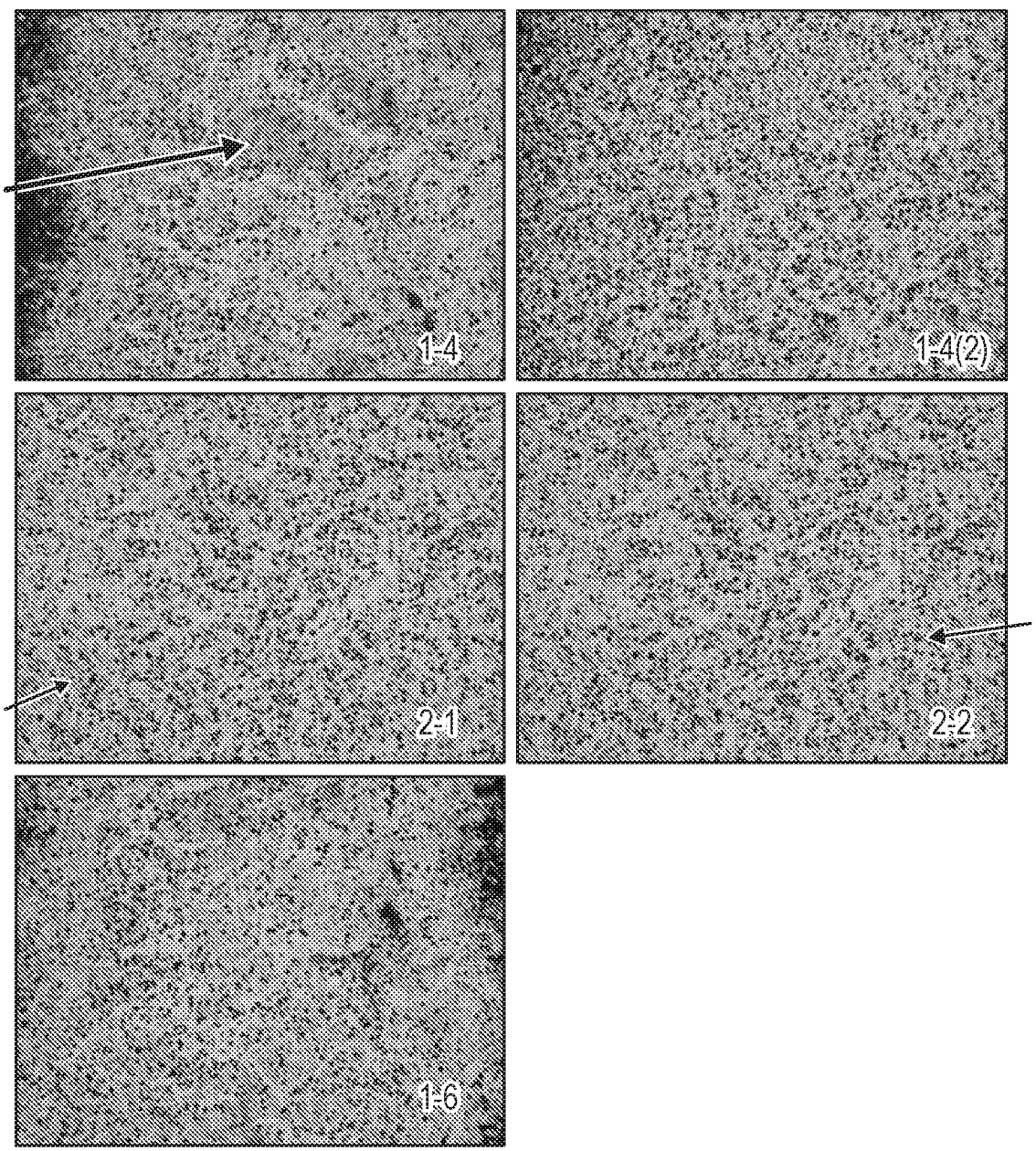
Figure 17B:
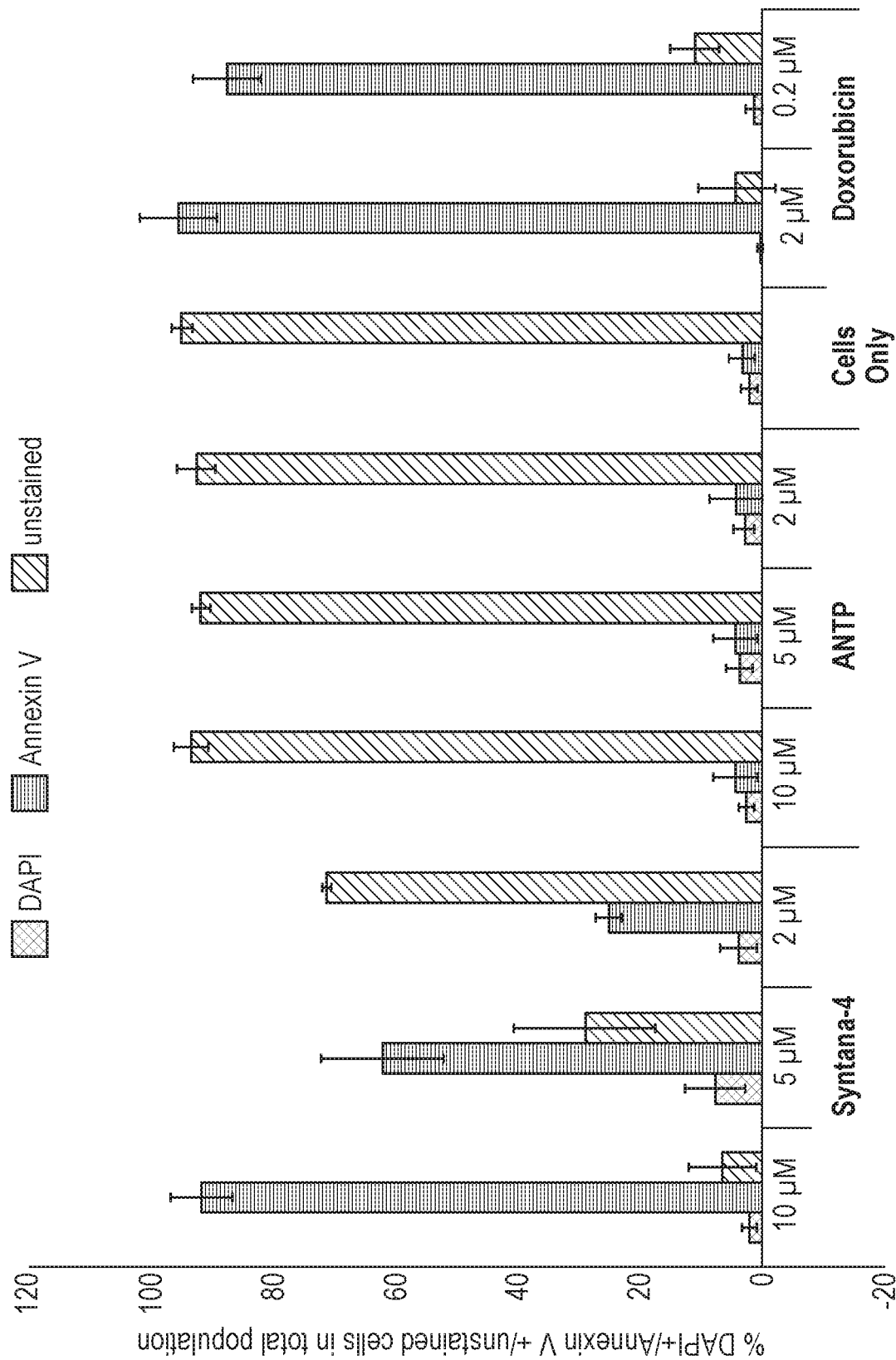

FIG. 16 Immuno-histochemistry images of Syntana-4 treated tumours, staining for Ki67 proliferative marker FIG. 17 Flow cytometry of MDA-MB-231 cells treated with Syntana-4 Apoptotic cells were identified and quantified by Annexin V-DAPI staining. Cells were plated at 15,000 cells/well and treated 48 h later in triplicate with Syntana-4, ANTP or doxorubicin. After 72 h, cells were analysed by Flow cytometry. Bottom left quadrant indicates live cells, bottom right indicates early apoptosis, top right indicates late apoptosis, top left indicates dead cells.

The proportion of apoptotic cells was calculated using the histograms.

Figure 18:
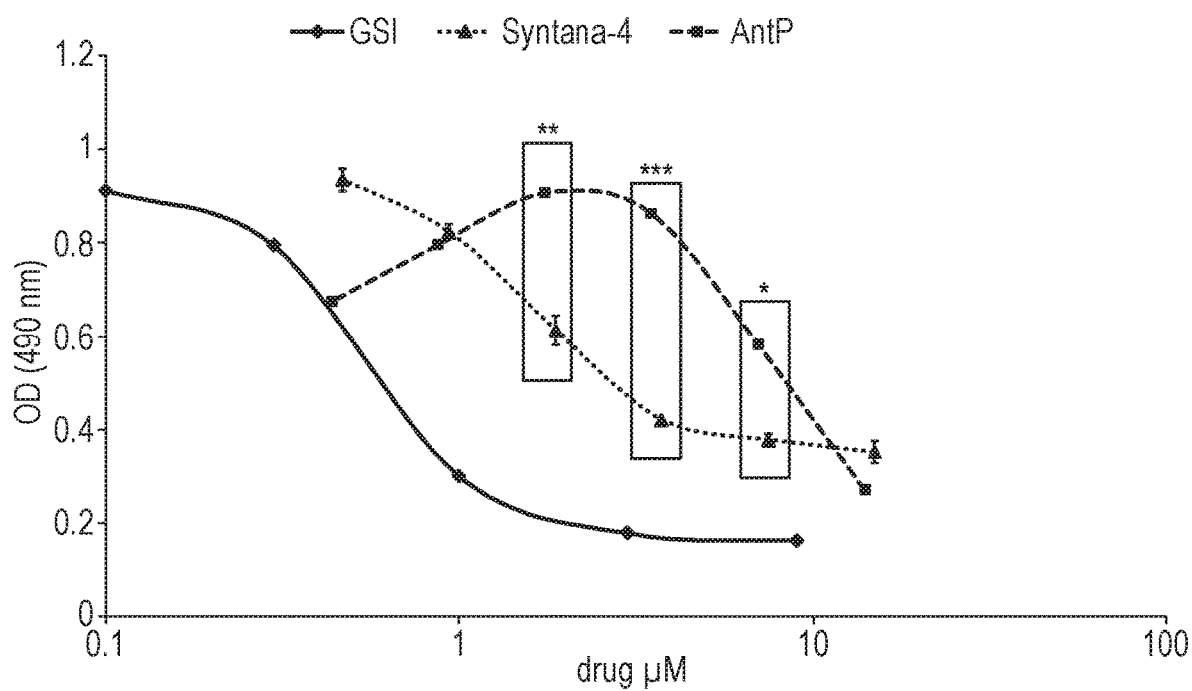

FIG. 18 Cell proliferation inhibition of MDA-MB-231 cells treated with Syntana-4 $*p<0.05$, $p<0.01$, $*p<0.001$

BRIEF SUMMARY OF THE SEQUENCE LISTING

SEQ ID NO:1 Homeodomain consensus sequence
SEQ ID NO:2 Amino acid sequence of the Antennapedia homeodomain
SEQ ID NO:3 Amino acid sequence of the Antennapedia homeodomain with conservative substitutions
SEQ ID NO:4 Amino acid sequence of penetratin
SEQ ID NO:5 Amino acid sequence of penetratin with conservative substitutions
SEQ ID NO:6 Amino acid sequence of human Mastermind-like 1
SEQ ID NO:7 Amino acid sequence of human Mastermind-like 2
SEQ ID NO:8 Amino acid sequence of human Mastermind-like 3
SEQ ID NO:9 Amino acid sequence of dnMAML (13-74)
SEQ ID NO:10 Amino acid sequence of full length conjugate (ANTP-dnMAML)
SEQ ID NO:11 Amino acid sequence of full length conjugate (penetratin-dnMAML)
SEQ ID NO:12 Amino acid sequence of full length conjugate plus a His-tag (Syntana-4)
SEQ ID NO:13 Amino acid sequence of HIV-TAT
SEQ ID NO:14 Amino acid sequence of MPG
SEQ ID NO:15 Amino acid sequence of PEP-1
SEQ ID NO:16 Amino acid sequence of FBI
SEQ ID NO:17 Amino acid sequence of Transportan
SEQ ID NO:18 Amino acid sequence of hCT(18-32)
SEQ ID NO:19 Amino acid sequence of KLA seq
SEQ ID NO:20 Amino acid sequence of AGR
SEQ ID NO:21 Amino acid sequence of LyP-2
SEQ ID NO:22 Amino acid sequence of REA
SEQ ID NO:23 Amino acid sequence of LSD
SEQ ID NO:24 Amino acid sequence of HN-1
SEQ ID NO:25 Amino acid sequence of CTP
SEQ ID NO:26 Amino acid sequence of HAP-1
SEQ ID NO:27 Amino acid sequence of 239P-1
SEQ ID NO:28 Amino acid sequence of an exemplary connecting peptide

DETAILED DESCRIPTION OF THE INVENTION

The term "Notch inhibitor" is intended to include any molecule that is able to reduce Notch signalling. Notch inhibitors can target any step in the Notch signalling pathway; including ligand-receptor binding, ADAM mediated cleavage, γ secretase mediated cleavage, Notch transcription complex assembly, or the expression of putative Notch target genes and proteins. Whether a molecule acts as a Notch inhibitor can be determined using standard molecular biology techniques. For example, the expression of putative Notch target genes (including Hes and Hey) in treated and control cells can be quantified by real time quantitative PCR (RT-qPCR), expression of a large number of Notch responsive genes can be quantified simultaneously using a Microarray, cleaved NICD can be visualised using labelled antibodies or in situ hybridisation, or transcriptional reporter assays utilising Notch-responsive promoters (based either on endogenous targets or on multimerised CSL-binding sites) can be used to control expression of fluorescent, bioluminescent, or other reporter proteins. NICD or NΔECD gain of function cells have constitutively high NOTCH activity and are therefore useful in these studies.

"Cell penetrating peptides" (CPPs) are typically 5 to 60 amino acid residues in length and facilitate cellular uptake of molecular cargo. CPPs may be naturally occurring peptides, fusion proteins, or entirely synthetic peptides (as classified in Guidotti G, Brambilla L, Rossi D. Cell-Penetrating Peptides: From Basic Research to Clinics. Trends Pharmacol Sci. 2017 April; 38(4):406-424). Routine experimental methods, including covalently coupling the candidate CPP to a fluorophore and quantifying the rate and/or extent of cellular uptake, can be used to determine whether a peptide should be classified as a CPP.

The term "conservative amino acid substitution" refers to substitutions that can be tolerated without compromising protein function. Conservative substitutions can be chosen based on a substitution matrix (e.g. PAM or BLOSUM) which represents the relative ease with which one amino acid may mutate into or substitute for another. Conservative substitutions typically involve replacing one amino acid with another that is similar in size and chemical properties. For example, substitutions between amino acids in the following groups are unlikely to disrupt protein function: amino acids with aliphatic side chains (i.e. alanine, isoleucine, leucine, proline and valine), amphipathic amino acids (i.e. arginine, lysine, glutamate and glutamine), amino acids with very hydrophobic aromatic side chains (i.e. phenylalanine and tryptophan), amino acids with slightly hydrophobic aromatic side chains (i.e. tyrosine and histidine), hydrophobic aromatic amino acids can sometimes substitute for aliphatic residues of a similar size (i.e. phenylalanine to leucine, but not tryptophan to valine), negatively charged polar amino acids (i.e. aspartate and glutamate), positively charges polar amino acids (lysine and arginine), neutral polar amino acids (i.e. histidine, asparagine, glutamine, serine, threonine and tyrosine), and small amino acids (i.e. alanine, cysteine, glycine, proline, serine and threonine).

The term "cancer stem cell" refers to tumour cells that have the principal properties of self-renewal, clonal tumour initiation capacity, and clonal long-term repopulation potential. The cell surface proteins CD133, CD24 and CD44 are putative markers for cancer stem cell (CSC) populations in some cancers and are associated with aggressive cancer types and poor prognosis. These markers also enable isolation of CSCs from bulk tumour for downstream analysis.

As used herein, the term "treating" means that the clinical signs and/or the symptoms associated with the cancer are lessened as a result of the actions performed. The signs or symptoms to be monitored will be characteristic of a particular cancer and will be well known to the skilled clinician, as will the methods for monitoring the signs and conditions. For example, the skilled clinician will know that the size or rate of growth of a tumor can monitored using a diagnostic imaging method typically used for the particular tumor (e.g., using ultrasound or magnetic resonance image (MRI) to monitor a tumor).

The phrase "pharmaceutically acceptable" is used to refer to those compounds, materials, compositions, or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "therapeutically effective amount" refers to an amount of a peptide conjugate of the invention alone to effectively act as an inhibitor of Notch signalling, or effectively treat or prevent proliferative diseases such as cancer. The term "therapeutically effective amount" also refers to an amount of a peptide conjugate of the invention in combination with other active ingredients, to effectively act as an inhibitor of Notch signalling, or effectively treat or prevent proliferative diseases such as cancer.

The terms "delivery" or "administration" are defined to include an act of providing a peptide conjugate or pharmaceutical composition of the invention to a subject in need of treatment. The terms include parenteral and topical administration. For example, the peptide conjugates and compositions can be administered by intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The Peptide Conjugate

The peptide conjugate of the invention comprises a first region that comprises or consists of a cell-penetrating peptide (CPP) moiety; a second region that comprises or consists of a therapeutic cargo moiety; and a connecting peptide between the first and the second region.

Low membrane permeability has historically been an obstacle to the intracellular delivery of polypeptides and is believed to limit the therapeutic benefit of many anticancer drugs. The invention relates to a therapeutic peptide conjugate comprising in its first region a cell-penetrating peptide (CPP) moiety. The CPP moiety facilitates internalisation of a second therapeutic moiety.

Described herein are peptides, compositions and methods that utilize the cell-penetrating ability of the *Drosophila* homeotic transcription factor Antennapedia (ANTP) or variants thereof. Specifically, peptides, compositions and methods of the invention generally makes use of the cell-penetrating ability of the 60 amino acid homeodomain found in ANTP (SEQ ID NO:2). Typically, homeodomains fold into a characteristic helix-loop-helix-turn-helix motif. In ANTP however, the "third" helix is generally considered to be two helices.

A number of cell-penetrating ANTP variants are known and are included within the scope of the invention. Variant CPPs for use in the conjugate, composition, or method of the invention may be produced by the removal of one or more amino acids from the N and/or C-terminal ends of SEQ ID NO:2. Truncations may also be generated by one or more internal deletions. The truncated derivatives may comprise or essentially consist of one or more alpha helices ($\alpha 1$, $\alpha 2$, or $\alpha 3$). In one embodiment, the CPP moiety is a 16 amino acid truncation of ANTP known as penetratin (SEQ ID NO:4). These residues correspond to residues 43 to 58 of ANTP (i.e. $\alpha 3$ helix of the helix-loop-helix-turn-helix motif). Accordingly, in some embodiments, the CPP moiety of the peptide, composition and method of the invention comprises or consists essentially of penetratin or suitable variants thereof.

The 60-amino acid homeodomain is highly conserved (SEQ ID NO:1). In animals, there are 16 major classes of homeobox genes; ANTP, PRD, PRD-LIKE, POU, HNF, CUT (with four subclasses: ONECUT, CUX, SATB, and CMP), LIM, ZF, CERS, PROS, SIX/SO, plus the TALE superclass with the classes IRO, MKX, TGIF, PBC, and MEIS. In plants, there are 11 major classes of homeobox genes; HD-ZIP (with four subclasses: I to IV), WOX, NDX, PHD, PLINC, LD, DDT, SAWADEE, PINTOX, and the two TALE classes KNOX and BEL. Additionally, the homeodomain has significant structural similarity with repressor proteins expressed in bacteriophage, particularly phage lambda.

Structural motifs that share amino acid sequence similarity with the ANTP homeobox domain are also anticipated to act as CPPs. In some instances, the conjugate, composition, or methods of the invention may use CPPs derived from alternative eukaryotic homeodomain proteins. In other instances, the conjugate, composition, or methods of the invention may use CPPs derived from bacteriophage repressor proteins.

In preferred embodiments, the conjugate comprises a CPP moiety with sequence similarity to SEQ ID NO:2. For example, a suitable variant CPP may have an amino acid sequence which has at least 60%, at least 70%, at least 80%, at least 85%, at least 90%, at least 95%, or at least 98% sequence identity to the 60 amino acid ANTP CPP (SEQ ID NO:2). Alternatively, the conjugate of the invention may comprise a CPP moiety with sequence similarity to the amino acid sequence of penetratin (SEQ ID NO:4). For example, a suitable variant CPP may have an amino acid sequence which has at least 60%, at least 70%, at least 75%, at least 80%, at least 85%, or at least 90% sequence identity to the 16 amino acid penetratin CPP.

Suitable CPP variants for use in the conjugate of the invention are derived from ANTP (SEQ ID NO:2). These variant may include one or more amino acid substitutions or internal deletions from the amino acid sequence of SEQ ID NO:2 or a fragment thereof (i.e. penetratin (SEQ ID NO:4).

In some instances, the CPP moiety shares at least 80% sequence identity to SEQ ID NO:2. In other instances, the CPP moiety shares at least 85% sequence identity to SEQ ID NO:2. In further instances, the CPP moiety shares at least 90% sequence identity to SEQ ID NO:2. In some instances, the CPP moiety shares at least 80% sequence identity to SEQ ID NO:4. In other instances, the CPP moiety shares at least 85% sequence identity to SEQ ID NO:4. In further instances, the CPP moiety shares at least 90% sequence identity to SEQ ID NO:4.

Sequence identity may be determined using one of a number of online programmes; including but not limited to ToPLign (BioSolveIT GmbH, Germany), BLAST2 (NCBI), SUPERMATCHER (L'Institut Pasteur, France), MATCHER (EMBOSS), or ClustalW (Thompson et al., 1994, supra). For example, sequence identity can be assessed using ClustalW and the following parameters:

Pairwise Alignment Parameters
Method: accurate, Matrix: PAM, Gap open penalty: 10.00, Gap extension penalty: 0.10;
Multiple Alignment Parameters
Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: GPSNDQEKR. Sequence identity at a particular residue is intended to include identical residues which have simply been derivatized.

A variant CPP for use in the conjugate, composition or method of the invention may comprise 1, 2, 3, 4, 5, 6, 7, 8, 9, 10, or up to 20 amino acid substitutions or deletions from full length *Drosophila* ANTP (SEQ ID NO:2). Alternatively, a variant CPP for use in the conjugate, composition or methods of the invention may comprise 1, 2, 3, or 4 amino acid substitutions or deletions from penetratin (SEQ ID NO:4). Preferably, amino acid substitutions are conservative in nature. For example, an amino acid may be substituted with an alternative amino acid having similar properties, (i.e. another basic amino acid, another acidic amino acid, another neutral amino acid, another charged amino acid, another hydrophilic amino acid, another hydrophobic amino acid, another polar amino acid, another aromatic amino acid or another aliphatic amino acid). Properties of the 20 naturally occurring amino acids are summarised below. This table can be used by the skilled person to establish which amino acids and be substituted. For example, lysine (K) residues are polar, hydrophilic, and positively charged, and can therefore be replaced by Arg (R) residues.

TABLE 1

Exemplary conservative substitutions

| Original Residue | Exemplary Conservative Substitution |
|---|---|
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala, Phe |
| Leu | Ile, Val, Met, Ala, Phe |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe. Thr, Ser |
| Val | He, Met, Leu, Phr, Ala |

The skilled person will understand that alternative CPPs may be used in the present invention. Examples of cell penetrating peptides are listed in the table below:

TABLE 2

Exemplary cell penetrating peptides (CPPs)

| CPP | Amino acid sequence |
|---|---|
| HIV-TAT | GRKKRRQRRRPQ (SEQ ID NO: 13) |
| MPG | Ac-GALFLGELGAAGSTMGAWSQPKKKRKV-cya (SEQ ID NO: 14) |
| PEP-1 | Ac-KETWWETWWTEWSQPKKKRKC-cya (SEQ ID NO: 15) |
| EB1 | LIKLWSHLIHIWFQNRREKWKKK (SEQ ID NO: 16) |
| Transportan | GWTLNSAGYLLGKINLKALAALAKKIL (SEQ ID NO: 17) |
| hCT(18-32) | KFHTFPQTAIGVGAP-NH2 (SEQ ID NO: 18) |
| KLA seq | KLALKLALKALKAALKLA (SEQ ID NO: 19) |

More recently, CPPs have been discovered that provide some degree of cell and tissue specificity. These so called "cell-penetrating homing peptides" recognise specific cell types in addition to being capable of translocating across the plasma membrane. Specific examples of cell-penetrating homing peptides include AGR (SEQ ID NO:20) which targets prostate carcinoma, LyP-2 (SEQ ID NO:21) which targets skin and cervical cancer, REA (SEQ ID NO:22)

which targets prostate, cervix, and breast carcinoma, LSD (SEQ ID NO:23) which targets melanoma and osteocarcinoma, (SEQ ID NO:24) which targets head and neck squamous cell carcinoma, CTP (SEQ ID NO:25) which targets cardiac myocytes, HAP-1 (SEQ ID NO:26) which targets synovial tissue, 293P-1 (SEQ ID NO:27) which targets keratocyte growth factor.

Further variants include unusual or un-natural amino acids, peptide branches or other modifications. Any modification should preferably avoid low synthesis yields, and should avoid aggregation or poor solubility. Modified amino acids may by incorporated to enhance affinity or stability of secondary structures. Modified amino acids can routinely be incorporated into peptides synthesised by SPPS. Examples include D-amino acids, homo amino acids, beta-homo amino acids, N-methyl amino acids, alpha-methyl amino acids, non-natural side chain variant amino acids and other unusual amino acids (e.g. (Cit), hydroxyproline (Hyp), norleucine (Nle), 3-nitrotyrosine, nitroarginine, ornithine (Orn), naphthylalanine (Nal), Abu, DAB, methionine sulfoxide or methionine sulfone). For example, D-amino acids may be incorporated to increase resistance against degradation enzymes, homo-amino acids have an additional $CH_2$ attached to the alpha-carbon of the amino acid and may have improved biological activity or stability.

In some instances, the CPP moiety will be positioned closer to the N-terminus of the peptide conjugate than the therapeutic moiety. In other instances, the CPP moiety will be positioned closer to the C-terminus than the therapeutic moiety. Preferably, the CPP moiety will be positioned closer to the N-terminus of the peptide conjugate than the therapeutic moiety.

The ability of a naturally occurring or synthetic sequence to translocate the membrane may be tested by routine methods known in the art and illustrated in the accompanying examples.

The peptide conjugate of the invention further comprises in its second region a therapeutic cargo moiety. A cargo moiety is a therapeutic peptide that is not naturally associated with the CPP moiety. In preferred embodiments, the cargo is an inhibitor of Notch signalling. The cargo moiety may be derived from a naturally occurring peptide. Alternatively, the cargo moiety may be engineered.

In preferred embodiments, the cargo moiety is derived from the co-activator Mastermind-like (MAML) protein (SEQ ID NO:6, SEQ ID NO:7, and SEQ ID NO:8). MAML is highly conserved. Therefore, any MAML homolog may be used in the conjugate, composition or method of the invention. The MAML derivative used in the invention should be able to bind to at least one of NICD or CBF-1. The MAML derivative used in the invention should also inhibit assembly of a functional Notch transcriptional complex.

Described herein are MAML (dnMAML) variants that may be used in the peptide conjugate of the invention. For example, one preferred embodiment utilises a 62-amino-acid MAML truncation known as dnMAML(13-74) (SEQ ID NO:9). The kinked alpha-helix of MAML(13-74) forms a stable ternary complex with CBF-1 and NICD. Since SEQ ID NO:9 lacks the C-terminal portion necessary for functional Notch transcriptional complex assembly, MAML(13-74) is a dominant-negative truncation. As reported in the Examples below, this peptide has been shown to be effective in inhibiting Notch signalling and the growth of tumors. Thus, in some embodiments the peptide conjugate comprises a cargo moiety comprising SEQ ID NO:9 or suitable variants thereof.

The solved crystal structure of the CBF-1-NICD-MAML ternary complex identified the residues that participate in transcriptional complex formation. These residues are underlined in the below sequence (SEQ ID NO:9) and should be retained in dnMAML variants of the invention:

LPRHSAVMERLRRRIELCRRHHSTCEARYEAVSPERLELERQHTFALHQ

RCIQAKAKRAGKH

The remaining amino acid residues may be replaced. Preferably, amino acid substitutions will be conservative in nature. The skilled person will be able to determine whether a given amino acid substitution will be conservative using common general knowledge and the information in Table 1. In some embodiments, the cargo moiety comprises an amino acid sequence that is at least 60%, at least 70%, at least 80%, at least 85%, at least 90%, at least 95%, at least 98% identical to SEQ ID NO:9. For example, in some instances, the cargo moiety comprises an amino acid sequence that is at least 80% identical to SEQ ID NO:9. In other instances, the cargo moiety comprises an amino acid sequence that is at least 90% identical to SEQ ID NO:9. In other instances, the cargo moiety comprises an amino acid sequence that is at least 95% identical to SEQ ID NO:9. In other instances, the cargo moiety comprises an amino acid sequence that is at least 98% identical to SEQ ID NO:9. In preferred instances, the cargo moiety comprises an amino acid sequence that is SEQ ID NO:9.

In preferred embodiments, the cargo moiety is derived from human MAML. In other instances, the cargo moiety may be derived from any MAML homolog. A variant cargo moiety may comprise an equivalent sequence derived from a different organism. For example, a dnMAML variant may comprise any peptide that is equivalent to amino acids 13 to 74 of the human MAML sequence but derived from the MAML gene of a different organism. Such a species variant may derive from any organism that expresses a MAML protein. For example, the species variant may derive from a mammal such as a primate, rodent or a domestic or farm animal. A variant peptide may also comprise a variant of such a species variant sequence such as a deletion, addition or substitution variant as described herein.

Further variants include modified, unusual or unnatural amino acids. Amino acids suitable for use in the present invention are described above and include D-amino acids, homo amino acids, beta-homo amino acids, N-methyl amino acids, alpha-methyl amino acids, non-natural side chain variant amino acids and other unusual amino acids (e.g. (Cit), hydroxyproline (Hyp), norleucine (Nle), 3-nitrotyrosine, nitroarginine, ornithine (Orn), naphthylalanine (Nal), Abu, DAB, methionine sulfoxide or methionine sulfone).

The ability of a peptide to inhibit Notch signalling can be easily tested by a person skilled in this field. For example, the ability of a peptide to inhibit Notch signalling can be measured in vitro. A suitable method is described in the Examples in relation to MDA-MB-231 cells.

The peptide conjugate of the invention comprises a connecting peptide between the first and the second regions of the conjugate. Preferably this connecting peptide or "linker" is directly attached to the first region and directly attached to the second region.

The first and second region of the peptide conjugate may be covalently or non-covalently linked. An appropriate linker should be chosen to preserve the biological activity of the CPP and cargo moiety. Preferably, the first and second regions of the peptide conjugate are covalently linked by a peptide linker. For example, the first and second regions of the peptide conjugate may be covalently linked by a short, flexible peptide linker.

The peptide conjugate of the invention may comprise a flexible linker, a rigid linker, or an in vivo cleavable linker. Besides the basic role in linking the functional domains together (as in flexible and rigid linkers) or releasing the free functional domain in vivo (as in in vivo cleavable linkers), linkers may offer other advantages, such as improving biological activity and achieving desirable pharmacokinetic profiles.

In some instances, the first and second regions may be linked by a flexible linker. Flexible linkers generally comprise small, non-polar (e.g. Gly) or polar (e.g. Ser or Thr) amino acids. The small size of these amino acids provides flexibility, and allows for mobility of the connecting functional domains. For example, Gly-rich linkers are flexible, connecting various domains in a single protein without interfering with the function of each domain. The incorporation of Ser or Thr can maintain the stability of the linker in aqueous solutions by forming hydrogen bonds with the water molecules, and therefore reduces the unfavorable interaction between the linker and the protein moieties.

In some instances, the first and second regions are connected by a short flexible linker. Naturally occurring peptide linkers include those that comprise the dipeptides Gly-Gly, Gly-Ala, Ala-Ser. These dipeptides may also be used in a linker of the peptide conjugate of the invention. Any number of these dipeptides may be combined to form a suitable peptide linker. For example, suitable peptide linkers include, but are not limited to: $G_n$ (where n is any number, but preferably 1 to 10); $(GA)_n$ (where n is any number, but preferably 1 to 5); $(AS)_n$ (where n is any number, but preferably 1 to 5); and any combination thereof. The peptide linker may additionally comprise small, hydrophobic residues, including Val, Ile, Leu, and Met. Additionally, or alternatively, the linker may comprise Glu and Phe. For example, in some embodiments, the connecting peptide comprises an amino acid selected from the group G, E, F, M or A. In a preferred embodiment, the amino acids in the connecting peptide are selected from the group consisting of G, E, F, M and A. In a further preferred embodiment, the peptide linker comprises or consists of the amino acid sequence GEFMA (SEQ ID NO:28).

In other instances, the first and second regions may be linked by a rigid linker. Typically, rigid linkers are used to prohibit unwanted interactions between discrete domains. Many natural, rigid linkers exhibited α-helical structures stabilised by intra-segment hydrogen bonds. Alternatively, in some instances, the rigid linker may be proline-rich. For example, the linker may have the sequence $(XP)_n$, wherein X designates any amino acid, and preferably Ala, Lys, or Glu. The presence of Pro in non-helical linkers can increase the stiffness, and allows for effective separation of the protein domains. The length of the linker can be easily adjusted by changing the copy number to achieve an optimal distance between domains.

The chosen linker should be of a suitable length and composition to reduce steric hindrance and permit any necessary inter-domain (i.e. cooperative) interactions. Although longer inter-peptide linkers are generally better at preserving the independent domain folding and biological activity, they are more susceptible to cleavage by proteases of the host cell, are known to enhance antigenicity and may cause peptides to aggregate. The skilled person will understand that the length of the linker can be adjusted as necessary to allow for proper folding or to achieve optimal biological activity of the peptide conjugate.

In some instances, the linker may be from 2 to 10 amino acids long, particularly between 2 and 10 amino acids long. For example, the linker may be 2, 3, 4, 5, 6, 7, 8, 9, or 10 amino acids long. In preferred embodiments, the linker is from 3 to 8 amino acids long, particularly between 3 and 8 amino acid residues long. In further preferred embodiments, the linker is 5 amino acid residues long.

It is also anticipated that the first and second regions may be joined by non-peptide linkers including beta-alanine, 4-aminobutyric acid (GABA), (2-aminoethoxy) acetic acid (AEA), 5-aminovaleric acid (AVA), 6-aminocaproic acid (Ahx), 8-Amino-3,6-dioxaoctanoic acid (AEEA, mini-PEG1), 15-amino-4,7,10,13-tetraoxapenta-decanoic acid (mini-PEG3), Trioxatridecan-succinamic acid (Ttds).

Exemplary conjugates are described herein. In a first embodiment, the peptide conjugate comprises: (a) first region comprising a cell-penetrating peptide of SEQ ID NO:2 (i.e. ANTP); (b) a second region comprising an inhibitor of Notch signalling, wherein the inhibitor is dnMAML(13 to 74) as defined in SEQ ID NO:9 and (c) a connecting peptide between the first and the second region that is from 2 to 10 amino acids long.

In a second embodiment, the peptide conjugate comprises: (a) a first region comprising a cell-penetrating peptide of SEQ ID NO:3 (i.e. ANTP variants with conservative substitutions); (b) a second region comprising an inhibitor of Notch signalling, wherein the inhibitor is dnMAML(13 to 74) as defined in SEQ ID NO:9; and (c) a connecting peptide between the first and the second region that is from 2 to 10 amino acids long.

In a third embodiment, the peptide conjugate comprises: (a) a first region comprising a cell-penetrating peptide of SEQ ID NO:4 (i.e. penetratin); (b) a second region comprising an inhibitor of Notch signalling, wherein the inhibitor is dnMAML(13 to 74) as defined in SEQ ID NO:9; and (c) a connecting peptide between the first and the second region that is from 2 to 10 amino acids long.

In a forth embodiment, the peptide conjugate comprises: (a) a first region comprising a cell-penetrating peptide of SEQ ID NO:5 (i.e. penetratin variants with conservative substitutions); (b) a second region comprising an inhibitor of Notch signalling, wherein the inhibitor is dnMAML(13 to 74) as defined in SEQ ID NO:9; and (c) a connecting peptide between the first and the second region that is from 2 to 10 amino acids long.

In a fifth embodiment, the peptide conjugate comprises: (a) a first region comprising a cell-penetrating peptide of SEQ ID NO:2 (i.e. ANTP); (b) a second region comprising an inhibitor of Notch signalling, wherein the inhibitor is a dnMAML(13 to 74) variant according to the sequence:

LPRHSAVMERLRRRIELC<u>RR</u>H<u>S</u>TCEAR<u>Y</u>EAVSPERLELERQ<u>H</u>TF<u>A</u>LHQ

RCIQAKAKRAGKH and wherein the underlined residues are conserved and none, one, two, three, four, five or more of the other residues are replaced by conservative substitutions; and (c) a connecting peptide between the first and the second region that is from 2 to 10 amino acids long.

In a sixth embodiment, the peptide conjugate comprises: (a) a first region comprising a cell-penetrating peptide of SEQ ID NO:3 (i.e. ANTP variants with conservative substitutions); (b) a second region comprising an inhibitor of Notch signalling, wherein the inhibitor is a dnMAML(13 to 74) variant according to the sequence:

LPRHSAVMERLRRRIELC<u>R</u>RHH<u>S</u>TCEAR<u>Y</u>EAVSPERLELERQH<u>TFAL</u>HQ
RCIQAKAKRAGKH and wherein the underlined residues are conserved and none, one, two, three, four, five or more of the other residues are replaced by conservative substitutions; and (c) a connecting peptide between the first and the second region that is from 2 to 10 amino acids long.

In a seventh embodiment, the peptide conjugate comprises: (a) a first region comprising a cell-penetrating peptide of SEQ ID NO:4 (i.e. penetratin); (b) a second region comprising an inhibitor of Notch signalling, wherein the inhibitor is a dnMAML(13 to 74) variant according to the sequence:

LPRHSAVMERLRRRIELC<u>R</u>RHH<u>S</u>TCEAR<u>Y</u>EAVSPERLELERQH<u>TFAL</u>HQ
RCIQAKAKRAGKH and wherein the underlined residues are conserved and none, one, two, three, four, five or more of the other residues are replaced by conservative substitutions; and (c) a connecting peptide between the first and the second region that is from 2 to 10 amino acids long.

In an eighth embodiment, the peptide conjugate comprises: (a) a first region comprising a cell-penetrating peptide of SEQ ID NO:5 (i.e. penetratin variants with conservative substitutions); (b) a second region comprising an inhibitor of Notch signalling, wherein the inhibitor is a dnMAML(13 to 74) variant according to the sequence:

LPRHSAVMERLRRRIELC<u>R</u>RHH<u>S</u>TCEAR<u>Y</u>EAVSPERLELERQH<u>TFAL</u>HQ
RCIQAKAKRAGKH and wherein the underlined residues are conserved and none, one, two, three, four, five or more of the other residues are replaced by conservative substitutions; and (c) a connecting peptide between the first and the second region that is from 2 to 10 amino acids long.

The linker in the conjugates of the invention, particularly the conjugate of any of exemplary embodiments (1) to (8), may be of any length that allows the cell penetrating peptide and the NOTCH inhibitor to fold correctly. In preferred embodiments, the peptide linker is a short amino acid sequence, for example, from 5 to 10 amino acids, particularly a sequence comprising or consisting of the residues GEFMA (SEQ ID NO:28). Preferably, the peptide conjugate of the invention is as defined in SEQ ID NO:10 or SEQ ID NO:11 or a variant thereof having at least 80% sequence identity thereto, more preferably at least 90% sequence identity thereto. Thus, in a preferred embodiment, the peptide conjugate of the invention is defined as in SEQ ID NO:10. In a further preferred embodiment, the peptide conjugate of the invention is defined as in SEQ ID NO:11.

The peptide conjugates may be further modified by, for example, the addition of one or more of an affinity tag, a solubilisation tag, a chromatography tag, an epitope tag, fluorescent tag, or a tag that allow enzymatic modification. Suitable tags which are well known in the art include: AviTag, Calmodulin-tag, polyglutamate tag, E-tag, FLAG-tag, HA-tag, His-tag, Myc-tag, NE-tag, S-tag, SBP-tag, Softag 1, Softag 3, Strep-tag, TC tag, V5 tag, VSV-tag, Xpress tag, Isopeptag, SpyTag, SnoopTag, BCCP, Glutathione-S-transferase-tag, GFP, HaloTag, Maltose binding protein-tag, Nus-tag, Thioredoxin-tag or Fc-tag. For example, the conjugate of the invention may comprise SEQ ID NO:12 (Syntana-4). Preferably, the peptide conjugate of the invention is as defined in SEQ ID NO:12 (Syntana-4) or a variant thereof having at least 80% sequence identity thereto, more preferably 90% sequence identity thereto. In a preferred embodiment, the peptide conjugate of the invention is as defined in SEQ ID NO:12 (Syntana-4).

In some embodiments, the full length of the peptide conjugate is no more than 190 amino acids. For example, the peptide conjugate may consist of fewer than 190 amino acids, fewer than 180 amino acids, fewer than 170 amino acids, fewer than 160 amino acids, fewer than 150 amino acids, fewer than 140 amino acids, or fewer than 130 amino acids. In preferred embodiments, the peptide conjugate consists of from 120 to 150 amino acids. For example, the conjugate may consist of between 120 and 150 amino acids, preferably from 125 to 138 amino acids, for example about 125 amino acids, about 130 amino acids, about 135 amino acids, about 140 amino acids, or about 145 amino acids. The conjugates defined in SEQ ID NO:10 and SEQ ID NO:12 (Syntana-4) consist of 127 and 136 amino acids residues respectively.

In some embodiments, wherein the first region consists essentially of SEQ ID NO:4 or a variant thereof, the peptide conjugate may consist of fewer than 110 amino acids, fewer than 100 amino acids, or fewer than 90 amino acids. In preferred embodiments, the peptide conjugate consists of from 80 to 100 amino acids. For example, the conjugate may consist of between 80 and 100 amino acids, and preferably from 80 to 90 amino acids, 82 to 88 amino acids, or 84 to 86 amino acids. For example, the conjugate may consist of about 85 amino acids, about 90 amino acids, or about 95 amino acids. The exemplary conjugate defined in SEQ ID NO:11 consists of 85 amino acids residues.

Method of Preparing the Conjugate

The peptide conjugate of the invention may be prepared by synthetic or recombinant technologies. Provided herein are synthetic peptide conjugates of the invention, particularly conjugates prepared by solid phase peptide synthesis (SPPS). Provided herein are methods of preparing the conjugate of the invention using SPPS. Detailed protocols for SPPS can also be found in Example 2. These described methods can be applied directly or modified to suit manual, quasi continuous flow, or fully automated SPPS systems.

The peptide conjugates may be prepared by stepwise solid-phase synthesis or convergent approaches involving solid-phase fragment condensation (SPFC).

SPPS relies on the iterative coupling of protected amino acids on a solid support. Due to extensive optimisation, including the design of powerful activating reagents for efficient backbone or side chain protecting groups, the design of unnatural amino acids, such as pseudo-prolines or isoacyldipeptides, which minimise side chain reactions or aggregation of the growing peptide, and powerful linker strategies and solid supports that facilitate elongation and cleavage, SPPS protocols now are routinely used to produce peptides of up to 40 amino acid residues. Therefore, according to one embodiment, the peptide conjugate is produced by stepwise solid phase peptide synthesis.

Alternatively, convergent approaches are often preferred when synthesising longer sequences. Convergent approaches exploit efficient step-wise SPPS to create short sequences, which are then purified and join together to form the target peptide. Convergent techniques can be divided into protected segment couplings and chemical ligations. In the former, segments that are fully protected aside from the termini that are to be coupled, are condensed via traditional methods involving carboxyl activation. In the latter, highly specific reactive groups are added to unprotected peptide fragments. For example, peptide segments may ligated using chemoselective amide bond forming reactions, including native chemical ligation (NCL). Preferably, the peptide conjugate is produced using convergent solid-phase peptide synthesis.

The skilled person will appreciate that the nature of the solid support, coupling chemistries, protection schemes, and the linkage for anchoring the peptide to the support are important variables and may affect the success of any SPPS protocol. Appropriate strategies for the synthesis of the conjugate are disclosed in the Example 2.

In one embodiment, the conjugate is synthesised by a method comprising or essentially consisting of the following steps:
1. functionalisation of a solid support;
2. coupling a first amino acid to the functionalised support;
3. washing the resin;
4. iterative deprotection and coupling reactions;
5. monitoring the progress of amino acid couplings (e.g. using ninhydrin or chloranil);
6. acetylating the N-terminus;
7. cleavage;
8. condensation or ligation of peptide fragments;
9. HPLC purification; and
10. analysis of the target peptide by mass spectrometry The ability of the peptide conjugate to traverse biological membrane is dependent the α-helical secondary structure. Earlier peptide conjugates produced by recombinant technology were unable to traverse biological membrane. Specifically, peptide conjugates extracted from bacterial cells and optionally exposed to small amounts of detergent (ionic and non-ionic) or denaturating agents (urea or guanidinium) were unable to enter cultured cells.

Described herein are additional steps that can be incorporated into the above protocol to prevent peptide aggregation and misfolding of the conjugate: modification of the mobile phase to disrupt hydrogen bonding (i.e. by addition DMSO, chaotropic salts, non-ionic detergents or of ethylene carbonate "Magic Mixture"), performing coupling reactions at elevated temperatures, sonication, or reducing the amount of peptide loaded on the resin is also known to reduce aggregation. It has been demonstrated that a peptide conjugate produced by SPPS, for example, using the protocols described herein, does not aggregate. Furthermore, it has been demonstrated that a peptide conjugate produced by SPPS folds into a functional peptide without additional denaturation-renaturation steps or chaperones.

Method of Treatment

Provided herein is a conjugate of the invention for use in a method of treating the human or animal body by therapy. In particular, the invention provides a conjugate for use in a method of treating cancer; the method comprising contacting a cancer cell with the conjugate. The conjugate comprises two moieties (or regions). In some instances, the first region comprising a cell penetrating peptide of SEQ ID NO: 4 or a homolog having at least 80% sequence identity. In other instances, the first region comprising a cell penetrating peptide of SEQ ID NO: 2 or a homolog having at least 80% sequence identity. The second region comprises a peptide that is an inhibitor of Notch signalling and is of SEQ ID No: 9 or a homolog thereof having at least 80% sequence identity thereto. In preferred embodiments, the first and second regions are connected by a peptide linker of from 2 to 10 amino acids, particularly between 2 and 10 amino acids.

Preferred conjugates for use in the methods are those referred to in the sections above that discuss the peptide conjugates of the invention and exemplary embodiments.

The invention also provides a conjugate for use in a method of treating or inhibiting cancer. In some instances, the conjugate may be used in methods to target tumour initiating cells (CSCs) and progenitor cells. In preferred embodiments, the conjugate is used in methods to target CSCs. By inhibiting Notch signalling in CSCs, the conjugate may be useful for reducing invasiveness or dissemination (metastasis) of CSCs. Invasiveness is associated with the epithelial-mesenchymal transition (EMT). The conjugate may additionally, or alternatively, be used in a method to prevent or reverse EMT trans-differentiation. Dysfunctional Notch signalling has also been linked to tumour-associated angiogenesis. The conjugate of the invention may therefore also be used to target stromal cells (i.e. vascular endothelial or perivascular cells) which form the tumour-associated microvasculature. Thus, according to some embodiments, invention provides a conjugate for use in a method of preventing or inhibiting tumour-associated angiogenesis. The conjugate may, for example, be used in a method of inhibiting, or preventing, sprouting angiogenesis, vascular remodeling, and pathological endothelial-mural cell interactions.

CSCs appear to be a common constituent of most, if not all, cancers. Therefore, the conjugate may be useful in methods of treating many different cancers, including hematopoietic malignancies, cervical, head and neck, endometrial, renal, lung, pancreatic, ovarian, breast, esophageal, oral, hepatocellular, and gastric carcinomas, osteosarcoma, mesothelioma, melanoma, gliomas, medulloblastomas, and rhabdomyosarcoma. In a preferred embodiment, the cancer to be treated is triple negative breast cancer. In another preferred embodiment, the cancer to be treated is T-cell acute lymphoblastic leukemia (T-ALL).

Typical conjugates for use in a method of treating cancer may comprise: (a) a first region comprising SEQ ID NO:2, SEQ ID NO:3, SEQ ID NO:4, or SEQ ID NO:5; (b) a second region comprising SEQ ID NO:9 or variants thereto; and (c) a connecting peptide between the first and the second region that is from 2 to 10 amino acids in length. Preferred conjugates suitable for use in a method of treating cancer are represented by SEQ ID NO:10, SEQ ID NO:11, and SEQ ID NO:12 (Syntana-4). In a specific embodiment, the conjugate of the invention for use in a method of inhibiting cancer has the amino acid sequence of SEQ ID NO:10.

These same conjugates may be used in the manufacture of a medicament for the treatment of cancer. In particular, the conjugates may be used in the manufacture of a medicament that targets cancer cells with dysfunctional Notch signalling. In a preferred embodiment, the conjugates may be used for the manufacture of a medicament that inhibits Notch signalling in CSCs. These CSC may reside in a number of different cancers, including but not limited to, hematopoietic malignancies, cervical, head and neck, endometrial, renal, lung, pancreatic, ovarian, breast, esophageal, oral, hepatocellular, and gastric carcinomas, osteosarcoma, mesothelioma, melanoma, gliomas, medulloblastomas, and rhabdomyosarcoma.

Also provided is a method of treating cancer using the conjugate of the invention, wherein the method comprises at least one of the following steps:

(a) identifying a subject susceptible to treatment, comprising determining the expression of one or more genes or protein involved in the Notch signalling pathway, wherein a change in activity or expression of one or more genes involved in the Notch signalling pathway as compared with the level in a normal cell is diagnostic of subject having or at risk of having cancer; and/or
(b) administering an effective amount of the conjugate to a subject in need thereof; and/or
(c) bringing the conjugate into contact with a cancer cell with dysfunctional Notch signalling.

In some embodiments, the invention provides a method of treating cancer comprising contacting a cancer cell (such as a CSC) with the conjugate of the invention. Non-limiting examples of cancer that may be treated by the described method include hematopoietic malignancies, cervical, head and neck, endometrial, renal, lung, pancreatic, ovarian, breast, esophageal, oral, hepatocellular, and gastric carcinomas, osteosarcoma, mesothelioma, melanoma, gliomas, medulloblastomas, and rhabdomyosarcoma.

For example, in a preferred embodiment, the method comprises treating a subject diagnosed as having T-ALL or triple negative breast cancer with a conjugate of the invention, wherein the conjugate comprises a first region that is a cell penetrating peptide of SEQ ID NO:2, SEQ ID NO:4 or a homolog having at least 80% sequence identity and in a second region a peptide that is an inhibitor of Notch signalling and is of SEQ ID NO:9 or a homolog thereof having at least 80% sequence identity.

Methods for identifying whether a subject is susceptible to treatment involve determining the expression of at least one gene involved in the Notch signalling pathway. In particular, a change in expression of at least one involved in the Notch signalling pathway, as compared to the expression level in a normal, non-pathological cell, is indicative of subject being susceptible to treatment using the conjugate. A similar change in expression or activity proteins involved in Notch signalling would also be indicative of susceptibility to treatment. In some instance, the gene or proteins involved in the Notch pathway are selected from the group consisting of Jagged1, Jagged2 Delta-like4, E-Cadherin, Numb, NICD Notch 3, Hey1, Hes5, or a combination thereof.

Also described are methods of monitoring a therapeutic regimen for treating a subject having or at risk of having cancer, comprising determining the activity or expression of one or more genes involved in the Notch signalling pathway. In one aspect, the gene involved in the Notch signalling pathway is selected from the group consisting of Jagged1, Jagged2 Delta-like4, E-Cadherin, Numb, NICD Notch 3, Hey1, Hes5, or a combination thereof.

The methods of the invention can also be performed by contacting samples of cells ex vivo, for example, in a culture medium or on a solid support. Alternatively, or in addition, the methods can be performed in vivo, for example, by transplanting a cancer cell sample into a test animal (e.g., a nude mouse), and administering the test agent or composition to the test animal. An advantage of the in vivo assay is that the effectiveness of a test agent can be evaluated in a living animal, thus more closely mimicking the clinical situation. Since in vivo assays generally are more expensive, they can be particularly useful as a secondary screen, following the identification of "lead" agents using an in vitro method.

Pharmaceutical Compositions

The conjugate of the invention may be formulated as a pharmaceutical composition. The pharmaceutical composition may be used in a method of therapy, and in particular, in a method or treating or preventing a disease, disorder or symptom linked to aberrant Notch signalling. For example, the pharmaceutical composition may be used in a method of treating cancer. The pharmaceutical composition of the invention may additionally or alternatively be used in the manufacture of a medicament for treating cancer. The invention further provides a method of treating or preventing cancer, wherein the method comprises administering to a subject in need thereof a pharmaceutical composition comprising a peptide conjugate of the invention.

Disclosed herein, the conjugate in the composition may have a concentration of from 1 to 50 mg/mL. For example, the conjugate may be from 2 to 40 mg/mL, 3 to 30 mg/mL, 4 to 20 mg/mL or 5 to 10 mg/mL. Preferably, the conjugate may be from 4 to 20 mg/mL. More preferably, the conjugate may be from 5 to 10 mg/mL. For example, the conjugate may have a concentration of about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, or about 10 mg/mL.

Formulation of a composition comprising a peptide conjugate of the invention can be carried out using standard pharmaceutical formulation chemistries and methodologies all of which are readily available to the reasonably skilled artisan. The composition of the invention comprises, in addition to the peptide conjugate of the invention, a pharmaceutically acceptable carrier, particularly at least one of: a pharmaceutically acceptable solvent, excipient or auxiliary compound. The solvents, excipients, and auxiliary substances are generally pharmaceutical agents that do not induce an immune response in the individual receiving the composition, and which may be administered without undue toxicity. The choice of pharmaceutically acceptable solvent, excipient or auxiliary compound will depend on the intended route of administration, standard pharmaceutical practice, and the known art. A thorough discussion of pharmaceutically acceptable excipients, vehicles and auxiliary substances is available in Remington's Pharmaceutical Sciences (Mack Pub. Co., N.J. 1991).

Pharmaceutically acceptable solvents useful for formulating an agent for administration to a subject are well known in the art. Preferred compositions for parenteral administration (i.e. intravenous bolus, intravenous infusion, intramuscular, intraperitoneal or subcutaneous injection) are in the form of a sterile aqueous solution such as water, physiologically buffered saline, or Ringer's solution. Other solvents that may be used include glycols, glycerol, oils such as olive oil or injectable organic esters. Compositions for parenteral administration may optionally contain other substances, for example, salts or monosaccharides to ensure the composition is isotonic with blood.

Alternatively, the peptide conjugate of the invention may be encapsulated, adsorbed to, or associated with, particulate carriers. Suitable particulate carriers include those derived from polymethyl methacrylate polymers, as well as PLG microparticles derived from poly(lactides) and poly(lactide-co-glycolides). See, e.g., Jeffery et al. (1993) Pharm. Res. 10:362-368. Other particulate systems and polymers can also be used, for example, polymers such as polylysine, polyarginine, polyornithine, spermine, spermidine, as well as conjugates of these molecules.

Compositions for sustained release or implantation may comprise pharmaceutically acceptable polymeric or hydrophobic materials such as an emulsion, an ion exchange resin, a sparingly soluble polymer, or a sparingly soluble salt.

In addition to the active ingredient, the pharmaceutical composition can contain physiologically acceptable excipients that act, for example, as dispersing agents, wetting agents, stabilising agents, suspending agents, emulsifying agents, chelating agents, pH buffering substances or compounds that increase absorption. Physiologically acceptable excipients include, for example, carbohydrates, such as glucose, sucrose or dextrans, and antioxidants, such as ascorbic acid or glutathione.

The pharmaceutical composition also can contain one or more additional auxiliary compound, such as a diagnostic reagent, nutritional substance, toxin, or therapeutic agent, for example, a cancer chemotherapeutic agent and/or vitamin(s).

The pharmaceutical compositions may be prepared, packaged, or sold in the form of a sterile injectable aqueous or oily suspension or solution. Injectable compositions may be prepared, packaged, or sold in unit dosage form, such as in ampoules or in multi-dose containers containing a preservative. In another embodiment, the active ingredient is provided in dry or lyophilised (e.g., a powder or granules) form for reconstitution with a suitable vehicle (e.g., physiologically buffered saline) prior to parenteral administration of the reconstituted composition.

Once formulated the compositions can be delivered to a subject in vivo using a variety of known routes and techniques. For example, a composition can be provided as an injectable solution, suspension or emulsion in oily or aqueous vehicles and administered via parenteral, subcutaneous, epidermal, intradermal, intramuscular, intra-arterial, intraperitoneal, intravenous injection using a conventional needle and syringe, or using a liquid jet injection system. Solutions, suspensions or emulsions may also be administered by a finely divided spray suitable for respiratory or pulmonary administration. If the peptide conjugate of the invention is formulated as a paste or implantable sustained-release or biodegradable formulation, the compositions may be administered topically to skin or mucosal tissue, such as nasally, intratracheally, intestinal, rectally or vaginally. Other modes of administration include oral administration, suppositories, and active or passive transdermal delivery techniques. A suitable route of administration may be determined by the skilled practitioner depending upon the particular symptom, disease or condition to be treated. Administration may be local to the site or tissue of interest, or may be systemic.

An appropriate effective amount can be readily determined by one of skill in the art. Such an amount will fall in a relatively broad range that can be determined through routine trials. The compositions may contain from about 0.1% to about 99.9% of the peptide conjugate and can be administered directly to the subject or, alternatively, delivered ex vivo, to a sample derived from the subject, using methods known to those skilled in the art.

The peptide conjugates or compositions are administered to a subject in an amount that is compatible with the dosage formulation and that will be therapeutically effective. An appropriate effective amount will fall in a relatively broad range but can be readily determined by one of skill in the art by routine trials. The "Physicians Desk Reference" and "Goodman and Gilman's The Pharmacological Basis of Therapeutics" are useful for the purpose of determining the amount needed. As used herein, the term "therapeutically effective dose" of a peptide of the invention means a dose in an amount sufficient to reduce Notch signalling and/or reduce or at least partially suppress the growth of tumours.

For example, when formulated for parenteral administration, the composition may be administered at a concentration of conjugate of from 1 to 50 mg/mL, 2 to 40 mg/mL, 3 to 30 mg/mL, 4 to 20 mg/mL or 5 to 10 mg/mL. Preferably, the conjugate may be administered at a concentration from 4 to 20 mg/mL. More preferably, the conjugate may be administered at a concentration from 5 to 10 mg/mL. For example, the conjugate may have a concentration of about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, or about 10 mg/mL.

The amount of conjugate (mg) administered to a subject may be calculated based on the mass (kg) or surface area ($m^2$) of the subject. For example, a therapeutically effective amount of conjugate may be administered as a dose of from 1 to 80 mg/kg. For example, the conjugate may be administered as a dose of from 2 to 80 mg/kg, for example from 10 to 70 mg/kg, 20 to 60 mg/kg, 30 to 50 mg/kg, or 40 mg/kg. Preferably, a therapeutically effective amount of conjugate is administered as a dose of from 20 to 60 mg/kg. More preferably a therapeutically effective amount of conjugate is administered as a dose of from 30 to 50 mg/kg.

For example, the conjugate or composition for parenteral administration (e.g., subcutaneous administration) may be administered as a dose of from 1 to 80 mg/kg. For example, the conjugate may be administered as a dose of from 2 to 80 mg/kg, for example from 10 to 70 mg/kg, 20 to 60 mg/kg, 30 to 50 mg/kg, or 40 mg/kg. Preferably, the conjugate or composition for parenteral administration may be administered as a dose of from 20 to 60 mg/kg. More preferably the conjugate or composition for parenteral administration may be administered as a dose of from 30 to 50 mg/mL.

Alternatively, the dose of the peptide conjugate may be between 0.1 to 40 mg/kg, for example from 1 to 40 mg/kg, 10 to 35 mg/kg, 15 to 30 mg/kg, for example about 20 mg/kg. For some peptide conjugates of the invention, the dose used may be higher, for example, 80 mg/kg or higher. For some peptide conjugates of the invention, the dose used may be higher than 40 mg/kg.

Such doses may be provided in a liquid formulation, at a concentration suitable to allow an appropriate volume for administration by the selected route.

Dosages for administration will depend upon a number of factors including the nature of the composition, the route of administration and the schedule and timing of the administration regime. The peptide conjugate or composition of the invention can be administered to a subject as a single dose by infusion over a relatively short period of time, or can be administered using a fractionated treatment protocol, in which multiple doses are administered over a prolonged period of time. For example, in one embodiment, a single dose is administered on a single occasion. In an alternative embodiment, a number of doses are administered to a subject on the same occasion but, for example, at different sites. In a further embodiment, multiple doses are administered on multiple occasions. For example, in a preferred embodiment, the peptide conjugate of the invention is administered at a dose of about 20 mg/kg every 3 days. Such multiple doses may be administered in batches, i.e. with multiple administrations at different sites on the same occasion, or may be administered individually, with one administration on each of multiple occasions (optionally at multiple sites). Any combination of such administration regimes may be used.

The composition may be formulated in a unit-dose or multi-dose sealed container. The unit dose may comprise from 1 mg to 200 mg, for example, from 2 mg to 180 mg, from 3 mg to 160 mg, from 4 mg to 140 mg, from 5 mg to 120 mg, or from 6 mg to 100 mg, from 7 to 80 mg, from 8 to 60 mg, from 9 to 40 mg, or from 10 to 20 mg of the conjugate. Preferably the unit dose may comprise from 8 to 60 mg of the conjugate. More preferably, the unit dose may comprise from 10 to 20 mg of the conjugate. The dose may be provided in a liquid formulation, at a concentration suitable to allow an appropriate volume for administration by the selected route. For example, wherein the conjugate is to be administered subcutaneously, the dose may be formulated in a volume of from 0.5 to 5 mL, for example, from 1 mL to 2 mL. Alternatively, where the conjugate is to be administered intravenously, the dose may be formulated in a volume of from 5 to 200 mL, for example, from 10 to 150 mL, from 15 to 100 mL, or from 20 to 50 mL. Preferably the conjugate may be formulated in a volume from 10 to 150 mL. More preferably, the conjugate may be formulated in a volume from 20 to 50 mL.

One skilled in the art would know that the amount of the peptide conjugate or therapeutic agent needed modulates the activity or expression of one or more genes in the Notch signalling pathway to treat cancer in a subject depends on many factors including the age and general health of the subject as well as the route of administration and the number of treatments to be administered. In view of these factors, the skilled artisan would adjust the particular dose as necessary. In general, the formulation of the pharmaceutical composition and the routes and frequency of administration are determined, initially, using Phase I and Phase II clinical trials.

The delivery of the peptide conjugate or composition of the invention may be used alone or in combination with other treatments or components of the treatment. Examples of chemotherapeutic agents that can be used in combination with agents described herein include, but are not limited to, small-molecule anticancer drugs (e.g. taxanes, platin analogues (cisplatin carboplatin, oxaliplatin) daunorubicin and other anthracyclines and polymers thereof, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, irinotecan, PARP inhibitors, diethylstilbestrol and other hormones and analogues), large-molecule anticancer drugs such as monoclonal antibodies (e.g. trastuzumab, bevacizumab, rituximab), or antibody-drug conjugates (e.g. trastuzumab emtansine, brentuximab vedotin). In some embodiments, the large molecule anticancer drugs are tyrosine kinase inhibitors (e.g. ado-trastuzumab, afatinib, axitinib, bosutinib, cabozantinib, crizotinib, dasatinib, emtansine, erlotinib, lapatinib, ibrutinib, imatinib, mastinib, midostaurin, nilotinib, pazopanib, pertuzumab ponatinib, ruxolitinib, sorafenib, sunitinib, trastuzumab, or vandetinib), In other embodiments, the peptides and compositions of the invention are administered with all new immuno-oncology therapies (e.g. chimeric antigen receptor (CAR) T-cell therapy). In some embodiments, the check point inhibitors are PD-1 and PD-L1 inhibitors. In some embodiments, the checkpoint inhibitors are nivolumab, pembrolizumab, ipilimumab, atezolizumab. The peptides and compositions of the invention can also be administered with anti-inflammatory agents (e.g. nonsteroidal anti-inflammatory drugs and corticosteroids) or antiviral drugs (e.g. ribivirin, vidarabine, acyclovir and ganciclovir). Two or more combined compounds may be administered separately, simultaneously, or sequentially.

The present invention relates in particular to the treatment of diseases or other conditions which are associated with aberrant activation of the Notch signalling pathway. These treatments may be used on any animal which is susceptible to aberrant activation of the Notch signalling pathway. For example, the subject to be treated may be any member of the subphylum cordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. In preferred embodiments, the subject will be a human. In alternative embodiments, the subject will be a domestic livestock, laboratory subject or pet animal. The molecules or compositions of the present invention may thus be used in the treatment of any such species. The above terms do not denote a particular age. Thus, both adult and newborn individuals are intended to be covered.

Also provided are peptide conjugates or pharmaceutical compositions, which are suitable for use in treating cancer, packaged in the form of a kit, preferably, in a container. The kits may comprise a series of components to enable treatment. For example, the kit may comprise the peptide conjugate of the invention in a lyophilised form, a suitable sterile, non-pyrogenic solvent (such as phosphate-buffered saline), and one or more additional therapeutic agents. Alternatively, the kit may comprise a pharmaceutical composition of the invention in a formulation suitable for parenteral administration, and one or more additional therapeutic agents. The kit may optionally include other suitable reagent(s), control(s) or instructions.

EXAMPLES

The following examples are provided to further illustrate the advantages and features of the present invention, but are not intended to limit the scope of the invention. While they are typical of those that might be used, other procedures, methodologies, or techniques known to those skilled in the art may alternatively be used.

Example 1: (Reference Example) Recombinant Production of ANTP-MAML (TR4)

Figure 1:
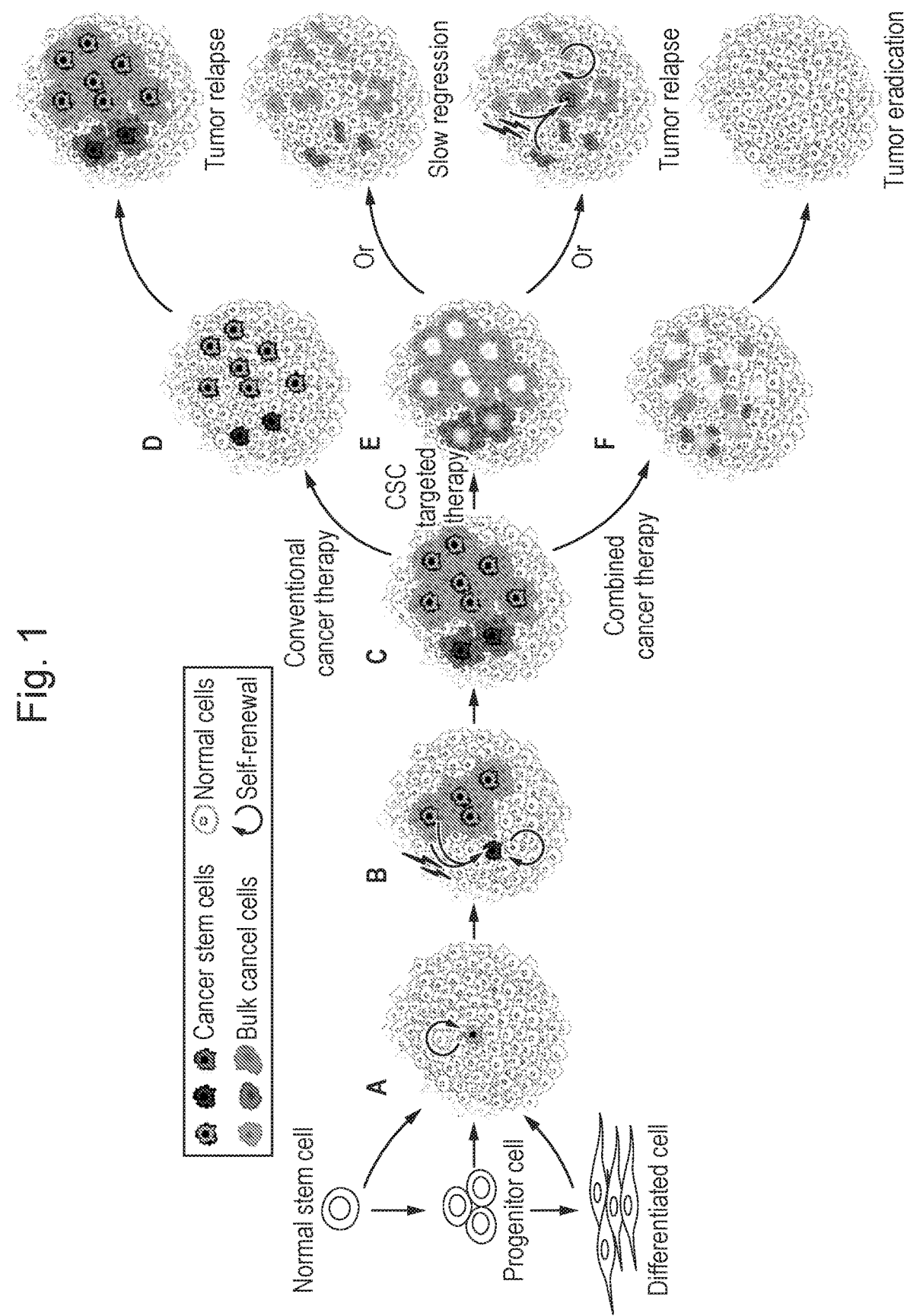
FIG. 1 Overview of the treating cancer by eradicating Cancer Stem Cells
Figure 2:
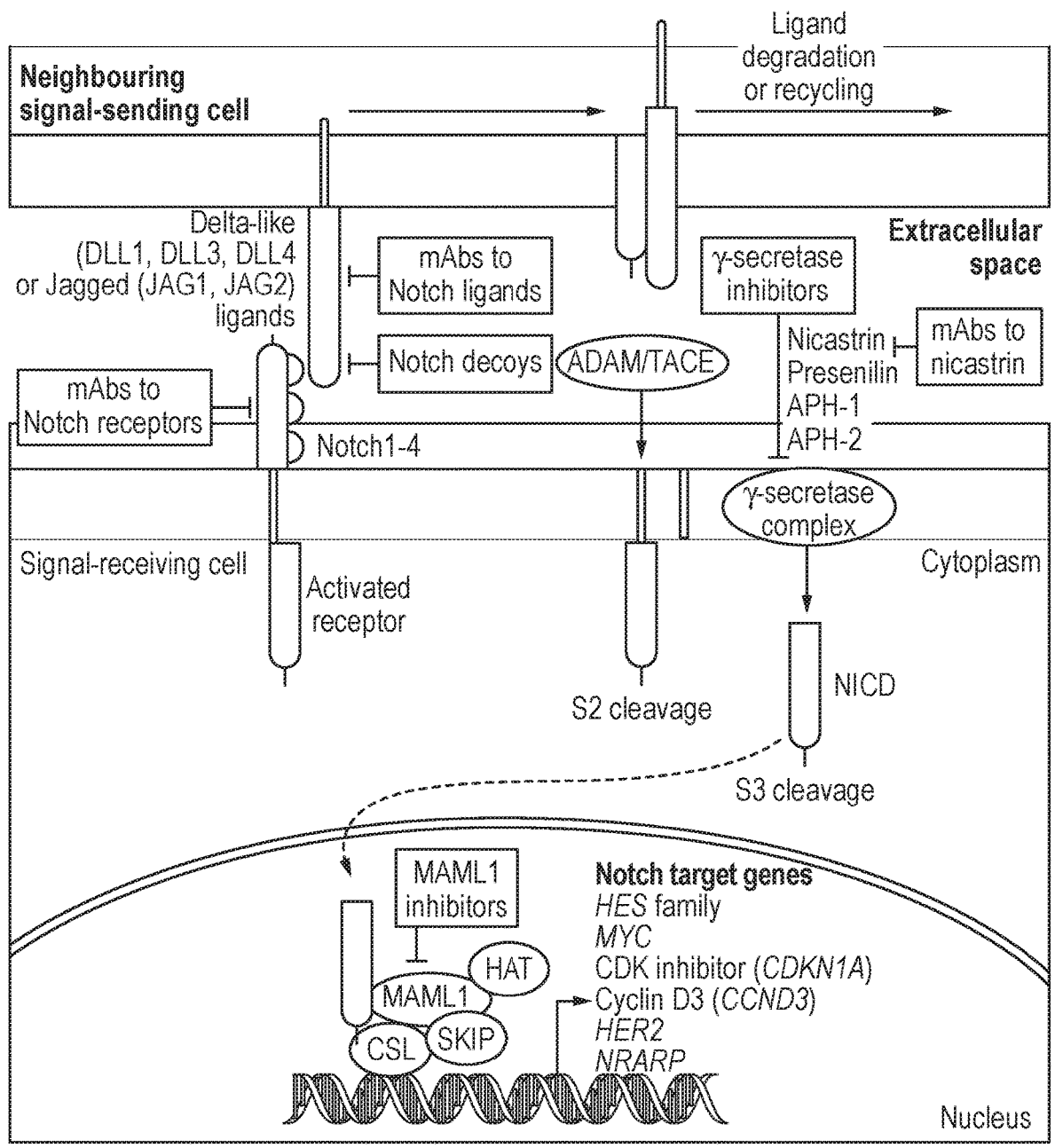
FIG. 2 Overview of the canonical Notch signalling pathway and various experimental pharmacological inhibitors under development FIG. 3 Expression and purification of ANTP FIG. 4 CD spectra that shows that the purified ANTP is expressed as a folded, helical-rich protein.
Figure 4:
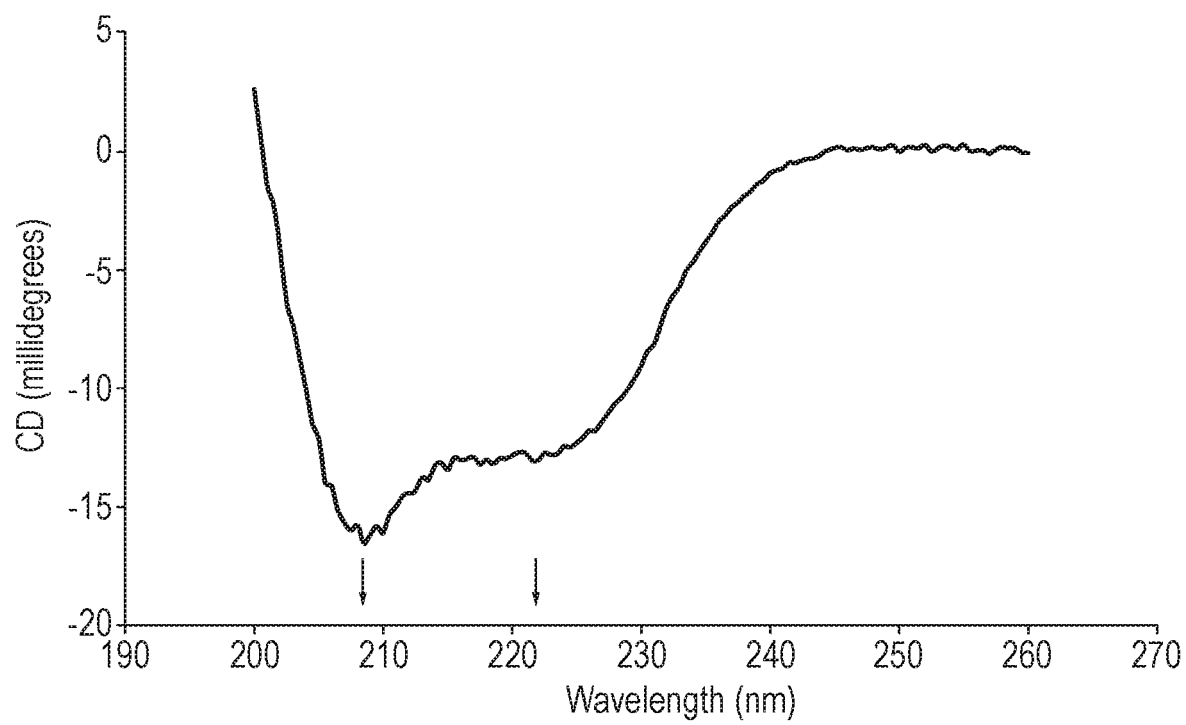

*E. coli* cells expressing an ANTP construct (U.S. Pat. No. 8,748,112) was lysed and the ANTP peptide was purified by either cation ion exchange (FIG. 3*a*) or size exclusion chromatography (FIG. 3*c*). According to the first method, the cell extract was applied to a cation ion exchange column in 10 mM phosphate buffer (pH 7). The ANTP peptide was gradient eluted with 1M NaCl in 10 mM phosphate buffer (pH 7). Purity was calculated as being at least 80% and yields were in excess of 10 mg/L bacterial culture. When purified using Superdex-75 size exclusion chromatography of the ion exchange, the peptide was at least 95% pure. The identity of the peptides was confirmed using anti-HIS blotting (FIG. 3*b* and FIG. 3*d* respectively). The circular dichroism spectrum of purified ANTP was measured between 190 and 270 nm. When dissolved in 10 mM sodium phosphate buffer (pH 7) at a concentration of 1 mg/ml isolated ANTP folds correctly as shown by its secondary structure (FIG. 4).

Figure 5A:
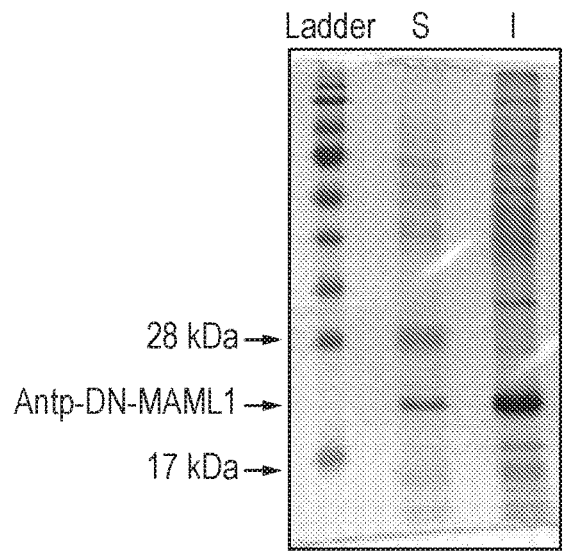
FIG. 5 Production of low yields of recombinant ANTP-dnMAML:
- a. Soluble (S) and Insoluble (I) fractions of recombinant ANTP-dnMAML expressed in *E. coli* BL21(DE3) using a T7-based expression vector.
- b. Anti-HIS blotting to confirm TR4 identity
- c. Refolding by stepwise dialysis, wherein S is the starting sample, 11 (Lane-1) is 6M urea dialysis, 12 is 4M urea dialysis, 13 is 2M urea dialysis, and 14 is the remaining soluble and folded TR4.
Figure 5B:
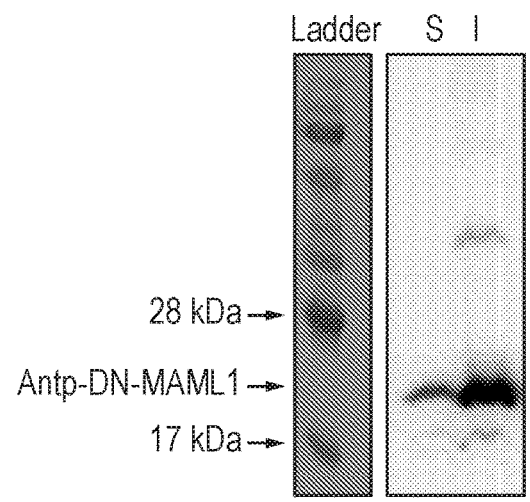
Figure 5C:
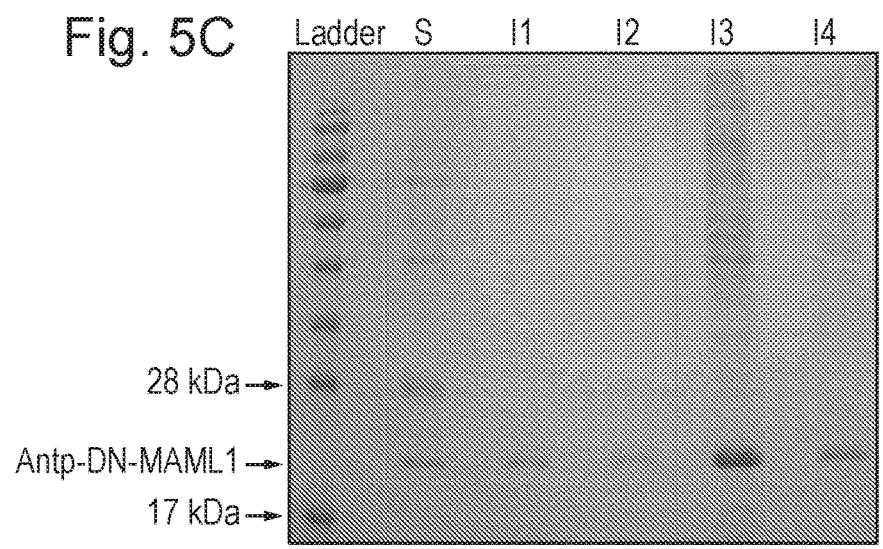

Recombinant ANTP-dnMAML(13-74) fusion proteins (WO 2009/044173) were produced using pET-based T7 expression vectors in either BL21(DE3), JM109(DE3) or Rosetta competent cells. Small amounts of recombinant ANTP-dnMAML peptides were expressed and formed insoluble intracellular aggregates (inclusion bodies). The inclusion bodies were extracted from bacteria using standard protocols (e.g. Triton-X100 extraction). Extracted recombinant peptides were then solubilised (e.g. using 6M GuHCl). Recombinant ANTP-dnMAML was then purified by IMAC under denaturing conditions in 8M Urea and refolded by stepwise dialysis into PBS buffer using well-known refolding methods (FIG. 5). On average, peptide yield was at least 0.1 mg/L bacterial culture.

Attempts to produce recombinant ANTP-dnMAML peptides in other host organisms or on a larger scale were unsuccessful. It was discovered that recombinant ANTP-dnMAML was unable to correctly fold and thus associated with the membrane component of the cells leading to insolubility and cell toxicity. Recombinant expression using *Pichia pastoris* was also tried, but the yields were low and most of the material was insoluble. The use of mammalian expression systems was also unsuccessful. For example, CHO cells transfected with a ANTP-dnMAML construct expressed under the control of a pCMV-based promoter, failed to express ANTP-dnMAML (FIG. 6). This result may be a result of recombinant protein induced toxicity.

For the following in vivo studies, the purity of the recombinant ANTP-dnMAML (i.e. TR4) was estimated to be approximately 20% by SDS-PAGE.

Breast cancer xenografts (MDA-MB-231) established in mice were used to assess the in vivo potency of TR4. The mice were divided into two groups, and injected every two days with 18 injections of either PBS as a control, or with recombinant ANTP/DN-MAML fusion protein (n=6 per group). Control mice treated with PBS developed rapidly growing tumors (FIG. 7).

The immunogenicity of recombinant ANTP/DN-MAML was investigated in immune-competent mice. Animals were immunized intravenously with recombinant ANTP/DN-MAML (0.2 ml, 2.5 mg/ml) without adjuvant, once per day for 5 days. Mice were bled once per week over a 4-month period, and the immune response monitored by ELISA. Blood samples were diluted 1:10, 1:100 and 1:1000 in PBS, and the immune response was monitored by ELISA on native recombinant ANTP/DN-MAML (coated at 50 pg/ml) and detected using anti-mouse antibodies. The results indicated that recombinant ANTP/DN-MAML does not raise an immune response in immunocompetent mice at a dose of 2.5 mg per week.

To determine the maximum tolerated dose, recombinant ANTP/DN-MAML tail vein administration was started when the mice reached an age of 12 weeks. Mice were continuously monitored for signs of hypoglycemic shock or drug side effects and were sacrificed if body weight loss exceeded 15%. Various dosages were tested starting at 4 mg/kg/day. It was found that 57 mg/kg/day of ANTP/DN-MAML is the maximum tolerated dose. At this dose, mice suffered from loss of appetite, weight loss and hypoglycemia. This experiment was terminated by sacrificing the animals three days after injection.

Example 2: Method for Synthesising a Peptide Conjugate Using Solid-Phase Peptide Synthesis Cesium Salt Method The first residue can be attached to a resin using a number of techniques. The methods described below are compatible with the use of a Merrifield resin. Dissolve the carboxylic acid in methanol (5 mL/mmol) and add water (0.5 mL/mmol). Titrate the solution to pH 7.0 with a 20% aqueous solution of cesium carbonate. Evaporate the mixture to dryness. Add DMF (2.5 mL/mmol) and evaporate to dryness (45° C.). Add a second portion of DMF (2.5 mL/mmol) and evaporate to dryness (45° C.). Set up a flask with a heating mantle and thermometer on an orbital shaker. Swell the resin in DMF (6-8 mL per gram of resin). Add the dry carboxylic acid cesium salt (1.0 equivalent based on the chlorine substitution of the resin). The cesium salt must be completely dry to obtain satisfactory results. Shake the mixture at 50° C. for 24 hrs. Filter the resin. Wash the resin thoroughly with DMF, then 50% (v/v) aqueous DMF, then 50% (v/v) aqueous methanol, and finally methanol. Dry the resin in vacuo to a constant weight.

Attachment of Fmoc-Amino Acids to Rink, PAL, or Sieber Resins

In a round bottom flask suspend the resin in 20% v/v piperidine/DMF (approximately 15 mL per gram of resin). In a separate flask dissolve 1.5 to 2.5 equivalents (relative to the resin) of the Fmoc-amino acid in a minimum amount of DMF. Add the same equivalency of HOBt. Stir the mixture until the HOBt dissolves. If the HOBt doesn't dissolve completely, add DMF to bring it into solution. Add 1.0 equivalent (relative to the amino acid) of DIC to the Fmoc-amino acid/HOBt mixture. Equip the flask with a drying tube. Let the mixture stand at room temperature for 10 minutes. Add the activated amino acid solution to the resin and equip the flask with a drying tube. Agitate the mixture with a mechanical shaker for 2 to 3 hours at room temperature. Remove a small sample of the resin and wash it with DCM. Test for free amino groups using the Kaiser test. If there are free amino groups, add 1 equivalent of acetic anhydride and pyridine to the reaction flask and mix for 30 minutes. Filter the resin in a fine porosity sintered glass funnel and wash it 3 times with DMF, then 3 times with DCM, and finally 3 times with methanol. In each wash use enough solvent to slurry the resin. After the final methanol wash, dry the resin in vacuo to a constant weight. The substitution of the resin can be estimated from the weight gain of the resin.

Standard Coupling Procedures

Described herein is a method to remove a Boc protecting group, the method comprising the following steps: Suspend the resin in 50% (v/v) TFA/dichloromethane (DCM), using 1 mL of TFA/DCM per gram of resin. Shake the resin at room temperature for 30 minutes. Filter the resin. Wash the resin three times with DCM (1 mL/gm resin). Wash the resin three times with 5% (v/v) diisopropylethylamine (DIPEA)/DCM) (1 mL/gm resin) to remove TFA.

Described herein is a method to remove a Fmoc protecting group, the method comprising the following steps: Place the resin in a round bottom flask and add 20% (v/v) piperidine in DMF (approximately 10 mL/gm resin). Shake the mixture at room temperature for 30 minutes. Filter the resin and wash it with several portions of DMF.

Also described is a standard capping procedure comprising the following steps: Filter and wash the resin several times with DMF. Suspend the resin in a DMF solution containing acetic anhydride (50 equivalent based on resin substitution) and pyridine (50 equivalents based on resin substitution). DIPEA may be substituted for the pyridine. Gently shake at room temperature for 30 minutes. Filter and wash the resin with DMF. Perform a Kaiser test. If the Kaiser test is not negative, repeat the capping procedure.

Monitoring the Solid Phase Reaction

The Kaiser Test is a very sensitive test for primary amines. It is commonly utilized in SPPS to determine if coupling reactions are complete. Ninhydrin reacts with the deprotected N-terminal amine group of the peptide-resin to produce an intense blue color. The Kaiser test is not reliable for detecting secondary amines. Thus, if the N-terminal amino acid is proline, pipecolic acid, or tetrahydroisoquinoline-3-carboxylic acid, another test such as the Isatin Test or the Chloranil Test is used.

| Reagent A | Reagent B | Reagent C |
|---|---|---|
| Dissolve 16.5 mg of KCN in 25 mL of distilled water. | Dissolve 1.0 g of ninhydrin in 20 mL of n-butanol. | Dissolve 40 g of phenol in 20 mL of n-butanol. |

Dilute 1.0 mL of above solution with 49 mL of pyridine (freshly distilled from ninhydrin).

pyridine (freshly distilled from ninhydrin).

Kaiser Test Procedure:

Take 10-15 beads of resin in a test tube and label it S. Take tube S and another empty tube designated R (reference) To each tube add: 2 to 3 drops of Reagent A; 2 to 3 drops of Reagent B; and 2 to 3 drops of Reagent C. Heat both the tubes at 110° C. for 5 minutes and compare the colour with the reference sample.

Standard HF Cleavage Method

Place a Teflon-coated stirring bar and the peptide-resin into the reaction vessel of the HF apparatus. Add the appropriate mixture of scavengers. Secure the cap onto the reaction vessel and cool it in a dry ice/methanol bath for at least 5 minutes. For every 0.2 mmol of substrate-resin, distill 10 mL of HF into the reaction vessel. Maintain the temperature between −5° C. and 0° C. while collecting the HF. Maintain the temperature between 0° C. and 5° C. for 30 to 60 minutes as the cleavage mixture is stirred. If the substrate contains Arg(Tos), the cleavage may take up to 2 hours. After the end of the reaction time, evaporate the HF under a stream of nitrogen. Filter the resin and wash it with a small amount of TFA. Combine the filtrates. Evaporate under reduced pressure to obtain the crude product.

EHPLC Purification and MS Verification of Peptides

Depending on how the synthesized peptide will be used, the crude peptide cleaved from the resin and isolated may be sufficiently pure. If the synthesized peptide requires HPLC purification, then a 30-minute gradient from 0% to 70% acetonitrile on a C-18 Peptide Column will usually provide peptide with satisfactory purity. Long peptides or relatively hydrophobic peptides could alternatively be purified on a C-4 or C-8 column. The HPLC solvents should contain 0.1% trifluoroacetic acid (TFA) which acts as an ion-pairing reagent and improves the shape of the peptide peaks. A suitable aqueous buffer reverse phase HPLC is 0.15% TFA in water. A suitable organic buffer reverse phase HPLC is 0.10% TFA in acetonitrile.

If the crude peptide has impurities that elute close to the product, a shallower gradient, such as 0%-30% acetonitrile or 10%-40% acetonitrile can provide better separation.

The crude peptide should be dissolved in a minimal volume of 0.1% aqueous TFA. If the peptide is not soluble in dilute TFA, it may dissolve in 6M guanidine hydrochloride containing 0.1% TFA. (6M guanidine hydrochloride solution can be prepared by dissolving 1 gram of guanidine in 1 ml of water). The guanidine salts elute in the void volume of the column while the peptide elutes later.

Inject the peptide solution onto the HPLC column and monitor the eluant from the column at 220 nm. Collect fractions as the peptide elutes. Test the fractions and combine all fractions that contain only the pure peptide. The combined fractions can be lyophilized to isolate the purified peptide.

The molecular weight of the peptide should be verified by mass spectroscopy (e.g. by ESI-QQQ, HPLC coupled to ESI-QQQ) using known methods.

Percent yield is calculated by comparing the dry mass of the peptide above to the theoretical yield calculated from the following equation:

Theoretical Yield (mg)=($s$resin)($m$resin)(MWproduct)

wherein sresin is the resin substituent in mmol/g, mresin is the resin dry mass in g, and MWproduct is the molecular weight of the product in mg/mmol.

Example 3: Synthetic Production of ANTP-MAML (Syntana-4)

Syntana-4 (SEQ ID NO:12) was synthesized by SPPS. Unexpectedly the process was high yielding and the peptide conjugate was functional. The full length peptide conjugate was purified by reverse-phase HPLC using an aqueous mobile phase consisting of 0.1% TFA in water, an organic mobile phase consisting of 0.1% TFA in acetonitrile, wherein the proportion of organic buffer was increased from 22-55% over 20 minutes. The eluted conjugate was at least 97% pure. The peptide was subsequently lyophilised and stored at −20° C.

Figure 8A:
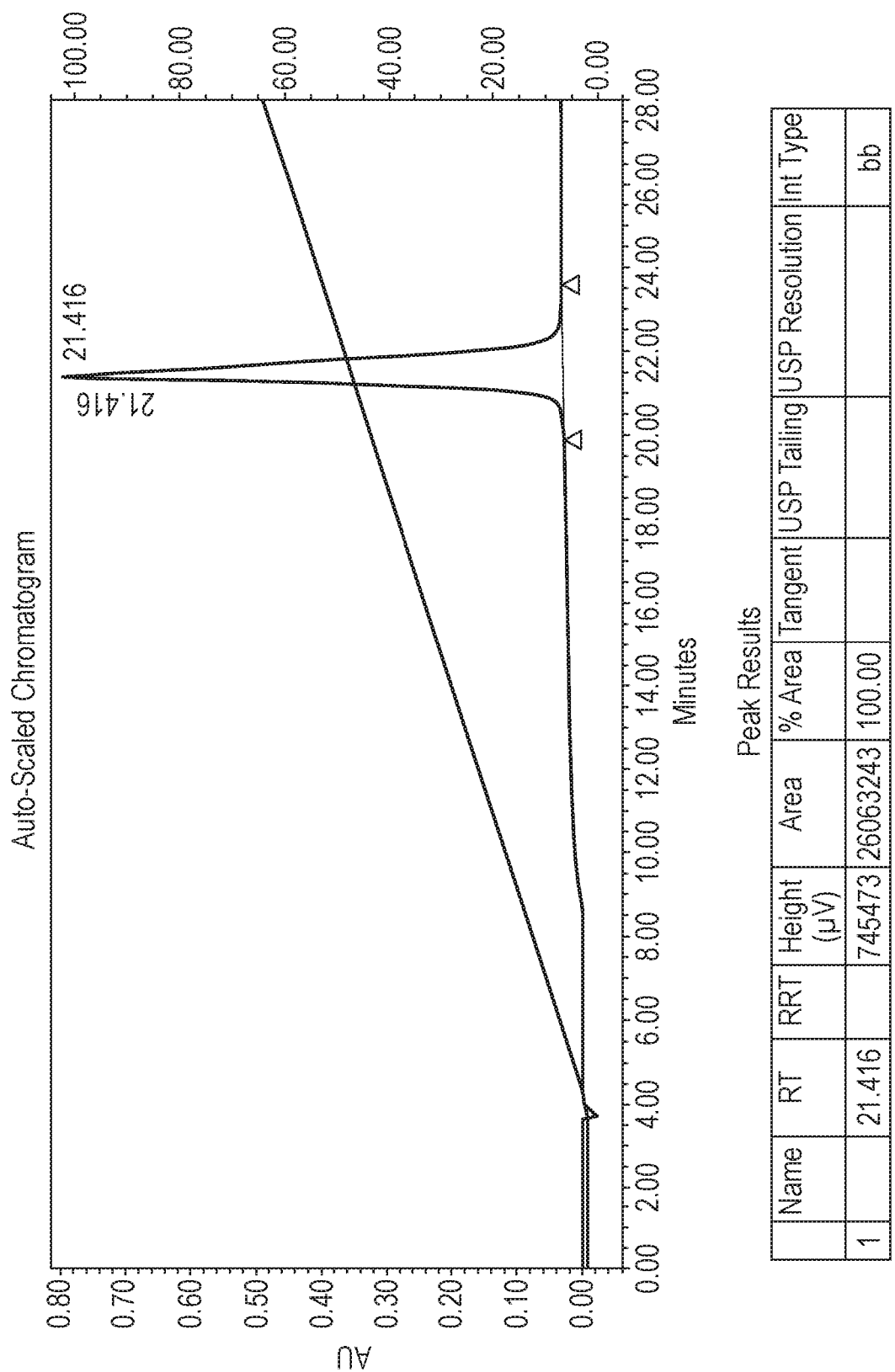
Figure 8B:
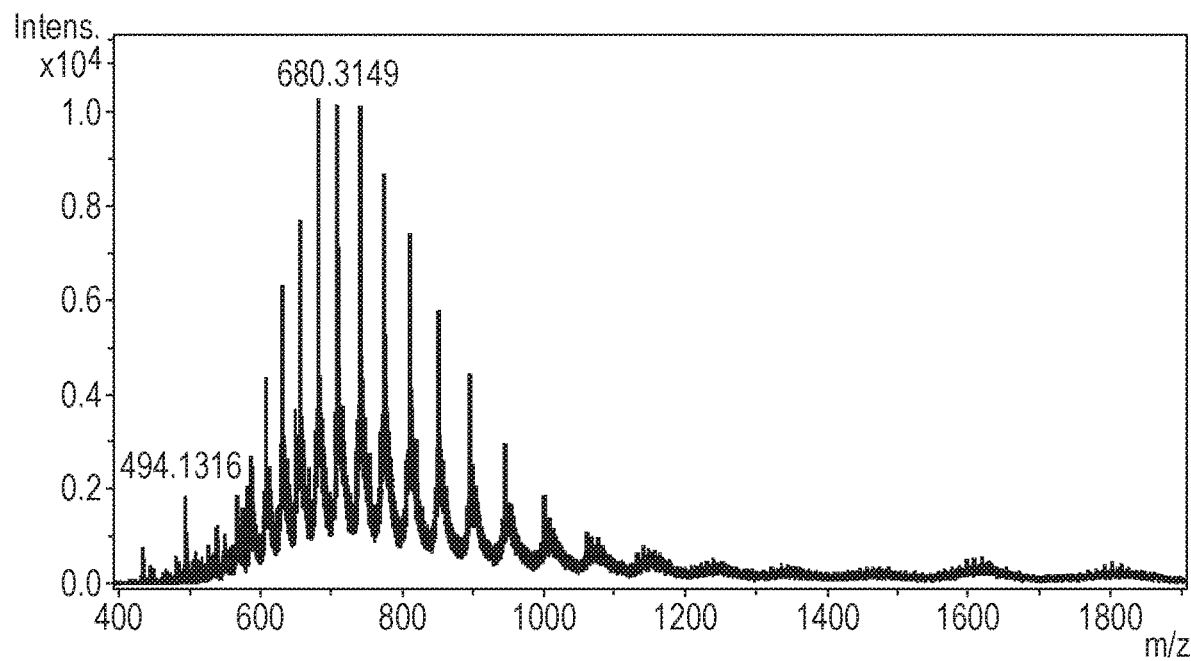
Figure 8C:
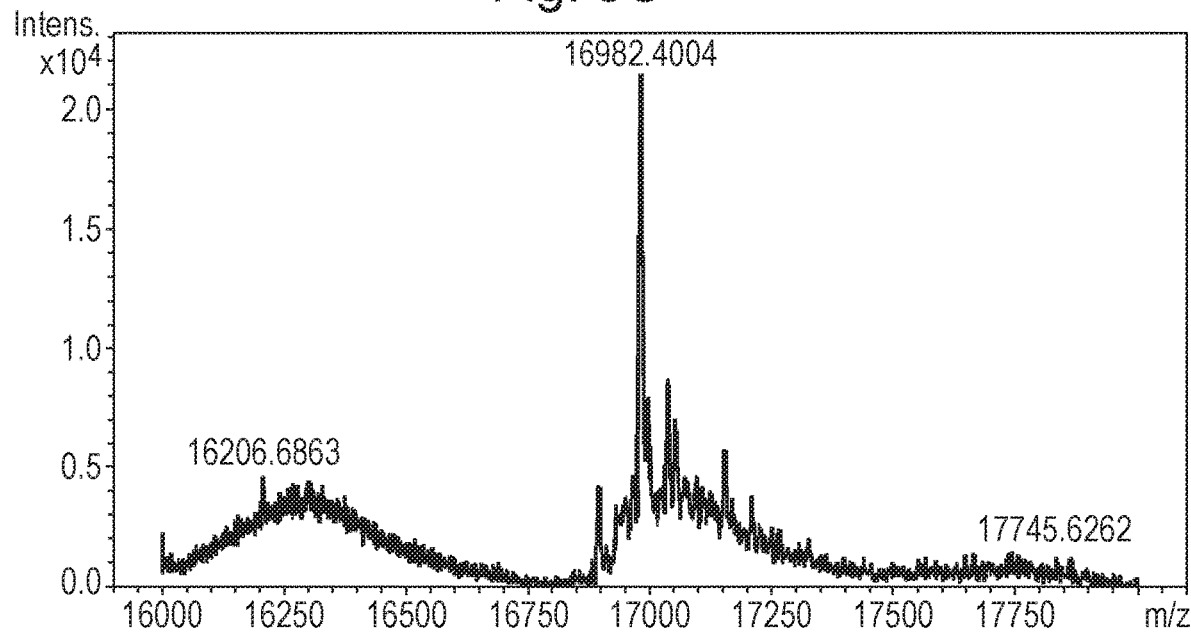

The conjugate was analysed by mass spectrometry. The expected MW is 16896 and observed was 16982 (FIG. 8) indicating that the correct peptide sequence had been made.

10 mg of Syntana-4 peptide was dissolved in 7 ml tissue culture grade PBS, gently vortexed and left at 4° C. for 48 hours. This equalled 1 mg/ml of net peptide (70% peptide content). The yield of soluble peptide was greater than 95%. Samples were aliquoted and stored frozen and were kept refrigerated throughout the various experiments.

Figure 9A:
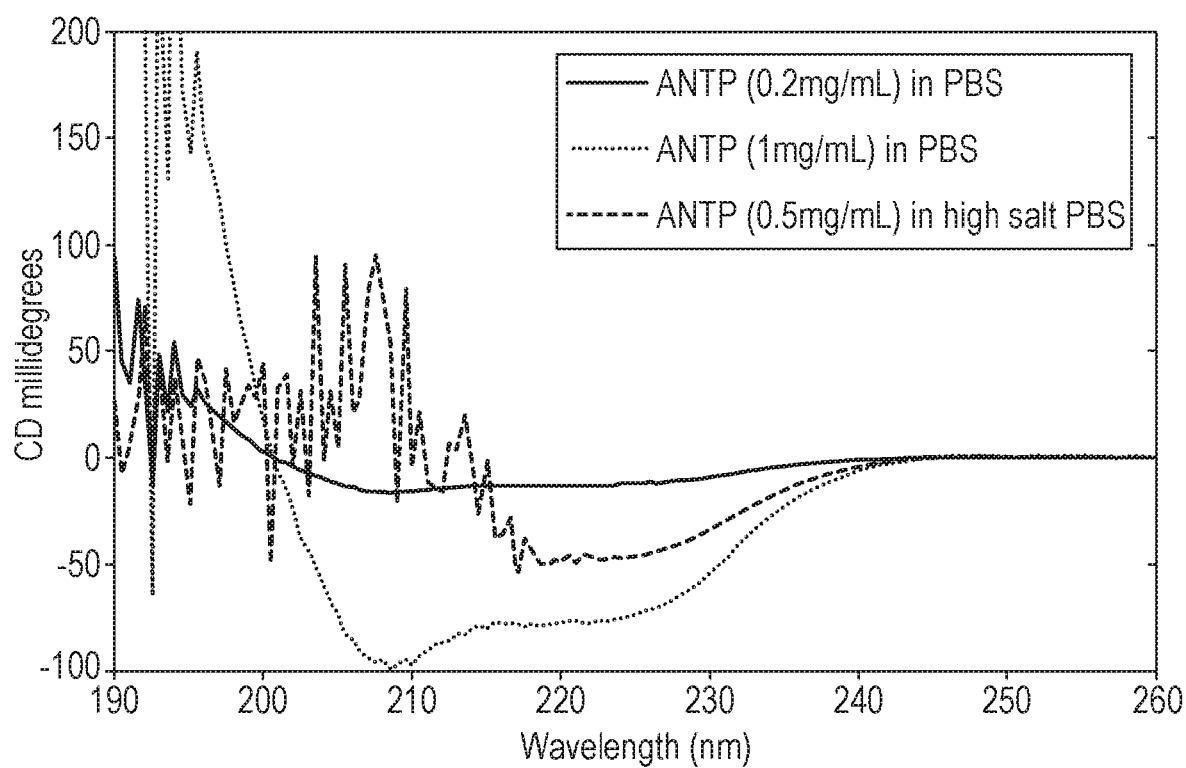
Figure 9B:
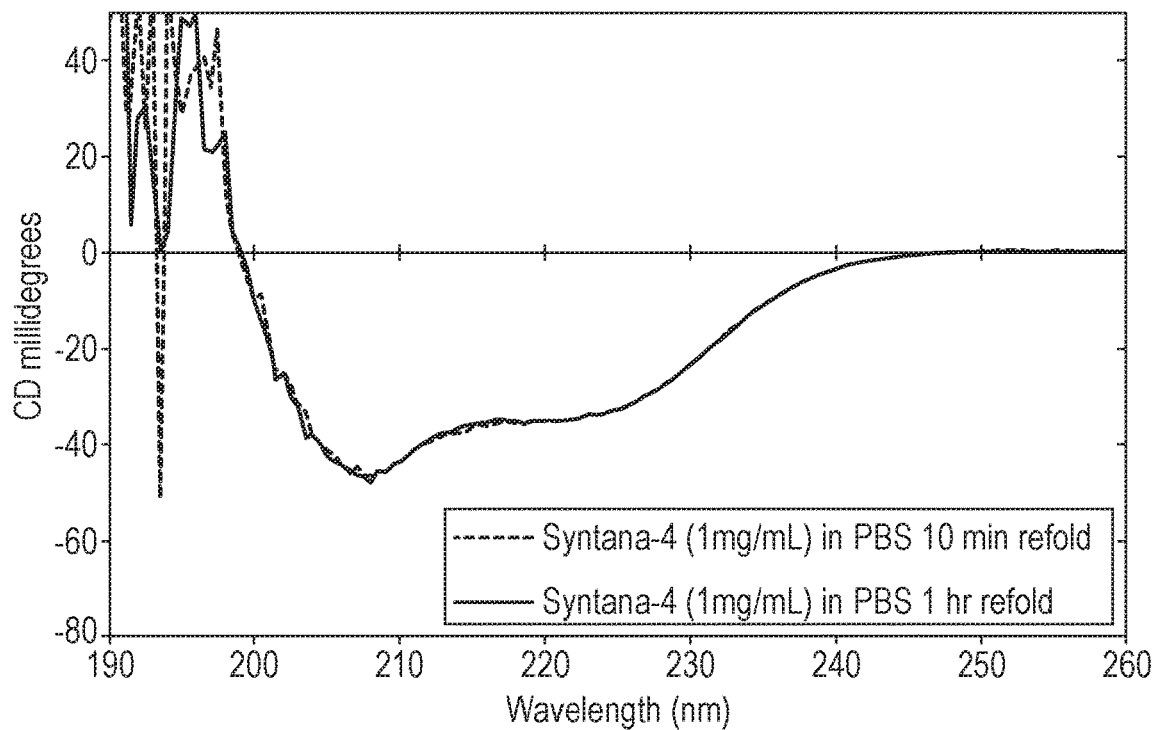
Figure 9C:
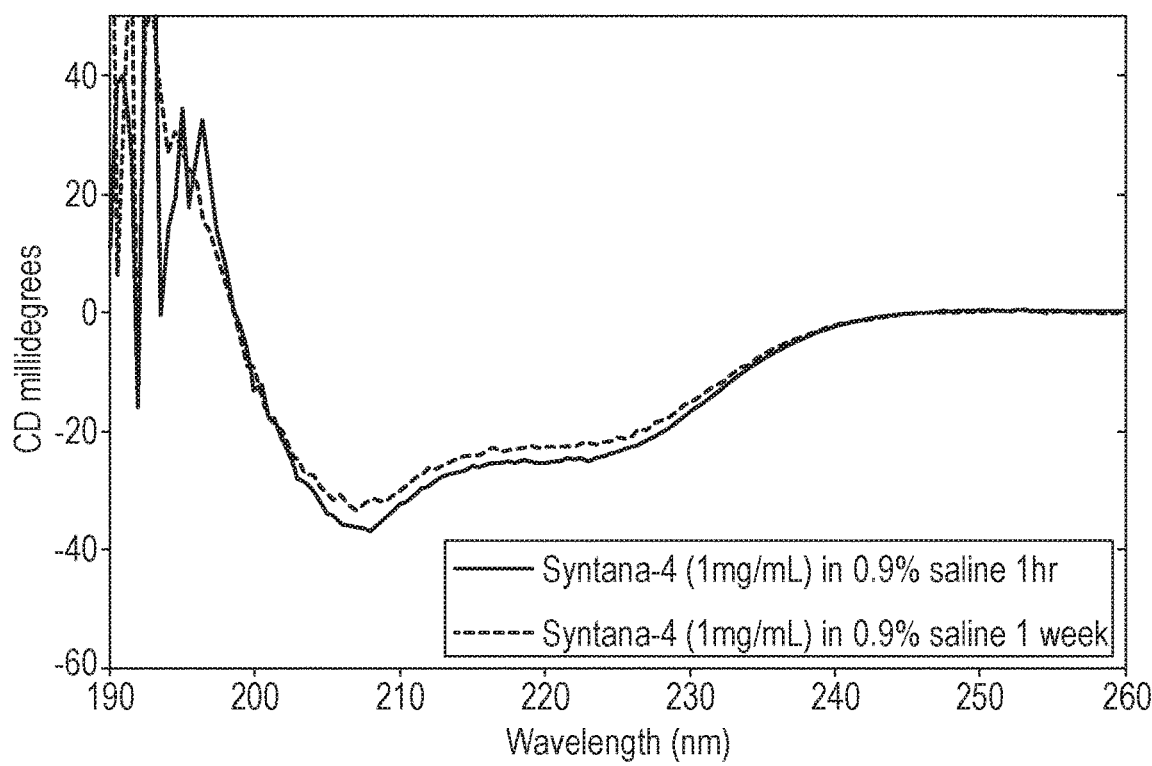
Figure 9D:
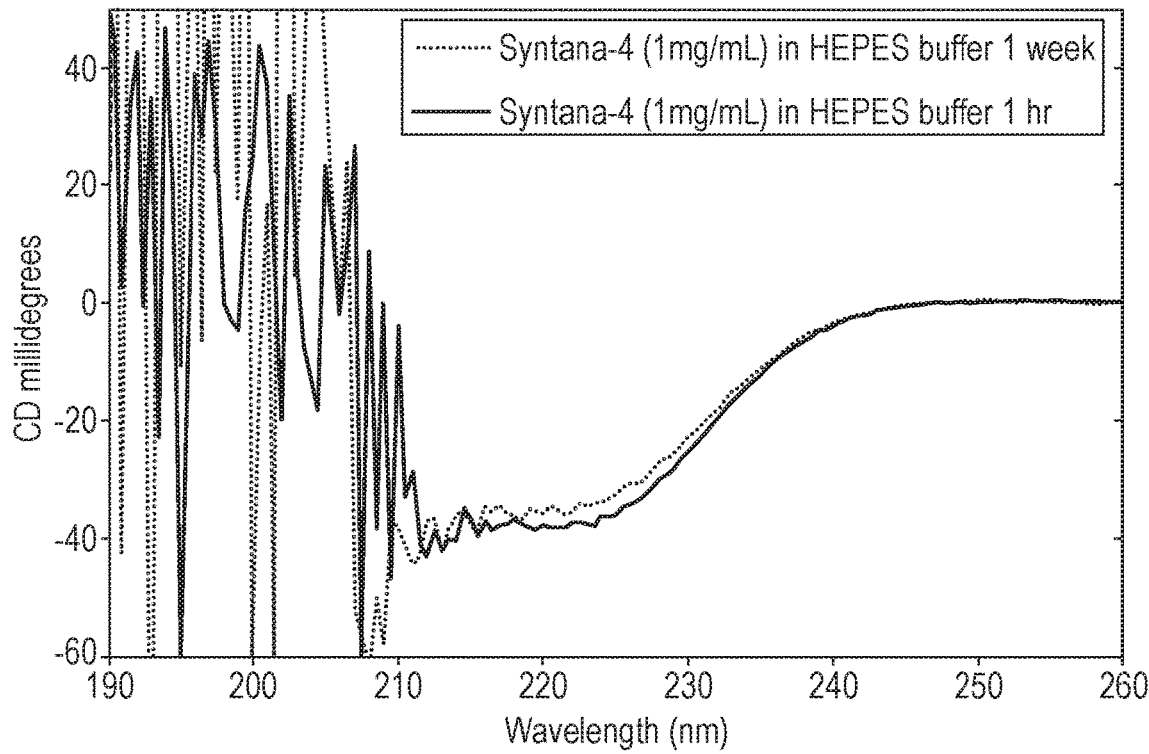
Figure 9E:
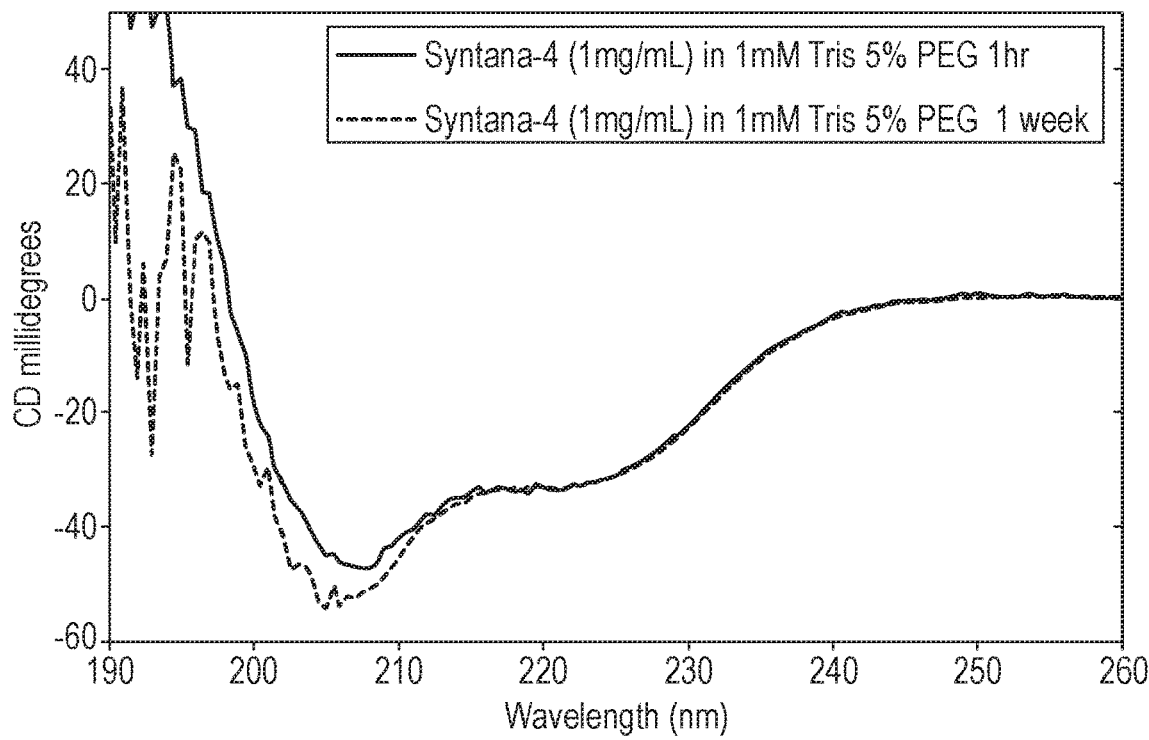

Recombinant ANTP and Syntana-4 was analysed by circular dichroism (CD) to assess the helical content. All samples gave a characteristic alpha-helix pattern. Some distortion of the CD spectra was seen at the lower wavelengths due to the high salt content, known to interfere with CD. ANTP showed the double minima typical of highly alpha-helical peptide structures in PBS buffer (FIG. 9*a*). When dissolved in one of 4 buffers, namely PBS (FIG. 9*b*), Non-buffered saline 0.9% (FIG. 9*c*), HEPES buffer (FIG. 9*d*), and 1 mM Tris-HCL pH 7.5, 5% PEG (FIG. 9*e*), Syntana-4 peptide regained a similarly high alpha-helical structures of 50-60%, consistent with the predicted 65% structure.

Example 4: Syntana-4 can be Concentrated to at Least 5 mg/mL

In Example 1, recombinant ANTP/DNMAML (TR4) was administered to mice as an impure formulation. Using SDS-PAGE the purity of TR4 administered to mice in Example 1 was estimated to be approximately 20%. Therefore, the concentration of TR4 used in these experiments is an overestimation. Instead, the inventors have demonstrated that TR4, prepared as described in Example 1, could not be concentrated beyond 0.5 mg/mL in PBS buffer without displaying signs of aggregation (visible precipitation).

In contrast, the purity of Syntana-4 is very high (99%). Pure Syntana-4 was also stable and soluble at 1 mg/mL and 5 mg/mL in PBS buffer as observed by its secondary structure (FIG. 10), with a characteristic alpha-helical plot which was linearly concentration dependent. Control samples, AntP and dnMAML also displayed alpha-helical structural properties. Other methods for determining relative protein concentrations and aggregation are known in the art, including liquid chromatography, multi-angled light-scattering, analytical ultracentrifugation and spectroscopic techniques.

Example 5: Dye Conjugations with Syntana-4

Figure 11:
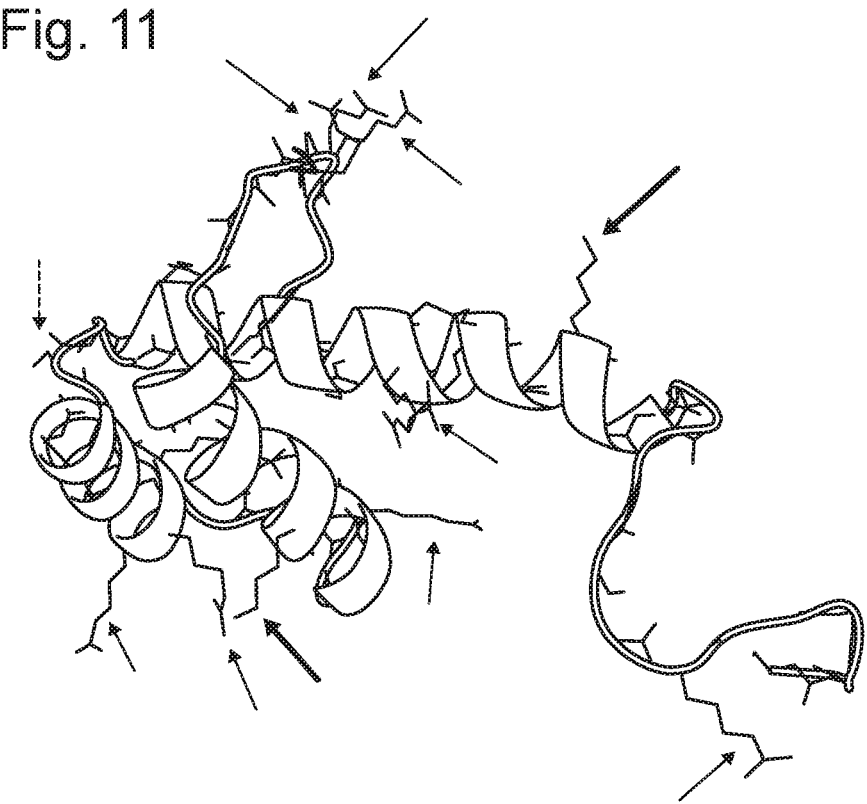

The molecular structure of ANTP (generated using Swiss PDB viewer using the solved NMR structure and the data files available from the RCSB Protein Data Bank https://www.rcsb.org/pdb/explore/explore.do?structureId=1SAN) shows exposed lysine residues and one exposed cysteine residue suitable for fluorescent labelling (FIG. 11).

Commercially available fluorescent dyes (FIG. 12) were conjugated to Syntana-4. Pilot conjugations were carried out on 1 mg/ml Syntana-4 peptide samples. 100 µg of Syntana-4 peptide was dissolved in PBS and treated with 10 mM TCEP to reduce the thiols for 1 hr. The samples were desalted in Zeba columns and reacted with a 20-fold molar excess of each dye. The unreacted dye was quenched with 40-fold free cysteine and purified by Zeba desalting columns. The UV-vis spectra was used to determine quality of conjugation and peak absorbance shifts (FIG. 13).

Syntana-4-IR, Syntana-4-Cy5 and Syntana-4-Cy5.5 all fluoresced as expected. The Syntana-4 peptide-IR dye peak (arrow, 2) is at 690 nm with a smaller peak in the required region of 620 nm. The peaks were sharp indicating a soluble conjugate, but the peptide peak (280 nm) was less sharp. The Cy5 conjugate peaks were at 600 nm and 650 nm (arrow, 2). The peaks were sharp indicating a soluble conjugate but the peptide peak (arrow, 1, 280 nm) was less sharp. The Cy5.5 conjugate peaks were at 630 nm and 680 nm (arrow, 2). The peaks were sharp indicating a soluble conjugate and the peptide peak (arrow, 1, 280 nm) was more sharp than the other two dye conjugates.

SDS PAGE gels viewed under fluorescence showed that the Syntana-4 peptide-IR dye conjugate was the brightest but had side-reaction products. The Cy5.5 and Cy5 conjugates were cleaner and showed fluorescent properties.

Syntana-4 can be successful conjugated to maleimide-based dyes (FIG. 13) showing that the Syntana-4 free thiol was accessible. Syntana-4-IR, Syntana-4-Cy5 and Syntana-4-Cy5.5 fluoresce as expected.

Example 6: Tumour Growth Inhibition

16 BALB/c nude mice (6-8 weeks old) were inoculated with 2 million MDA-MB231 tumour cells in ice-cold 50% DMEM media/FCS+50% matrigel, subcutaneously. These tumours were monitored and used when they had grown to around 24-100 mm³ (around 4-5 mm diameter). The mice were randomised and grouped (6 in Syntana-4 therapy, 5 in chemotherapy and 5 saline treated). The 16 mice were treated as follows:

| Group | Sample size | Therapy | Dosage regime |
| --- | --- | --- | --- |
| 1 | 6 | Syntana-4 therapy | 4 mg/kg, 3 times per week, 8 doses (approx 0.1 mg/mouse) |
| 2 | 5 | Control - chemotherapy Paclitaxel (PTX) | 10 mg/kg, 2 times per week, 5 doses |
| 3 | 5 | Control - saline treated | 3 times per week, 8 doses |

At the end of the treatment regime, the animals were culled and dissected. The GI tract was removed and washed through with sterile saline solution. The tumours were dissected and divided in two. Half of the tumour was snap frozen in liquid nitrogen and used to make mRNA for Q-PCR of Notch genes. The other half of the tumour was paraffin-embedded and sectioned (5-10 µm) onto slides. 4 Syntana-4 treated tumours produced satisfactory tissue pieces for evaluation.

Tumour sizes were calculated as (L×W×W)/2 and plotted as a percentage change from the day treatment started (FIG. 14). In two independent experiments, Syntana-4 was able to delay tumour growth compared to standard chemotherapy (Paclitaxel). Using ANOVA, which takes into account the growth progress (repeated measures), the reduced tumour growth compared to the controls (Paclitaxel and Saline) is statistically significant.

The Syntana-4 data points for days 14, 16 and 18 are (Students T-test)

| Comparison | Day 14 P-value | Day 16 P-value | Day 18 P-value |
| --- | --- | --- | --- |
| Saline vs Syntana-4 | 0.01, significant | 0.04, significant | 0.03, significant |
| Chemotherapy vs Syntana-4 | 0.14. not significant | 0.12, not significant | 0.04, Significant |

The P-values for the significance of responses (2-way ANOVA) are

| Comparison | P-value | Significant difference? |
| --- | --- | --- |
| Saline vs Syntana-4 | 0.006 | YES |
| Chemotherapy vs Syntana-4 | 0.11 | NO |

Example 7: Pharmacodynamic Studies

RT-Quantitative-PCR was performed to assess the effect of Syntana-4 on the expression on Notch target genes and Notch-1 and Notch-4 genes. mRNA was extracted from snap frozen excised tumour tissue using the RNAEasy QIAGEN kit. cDNA was produces from 0.5 µg of total RNA, using the Roche First Strand DNA synthesis kit. The table below summarises fold changes in gene expression from four Syntana-4 treated tumours compared to control (saline treated) animals. The gene expression levels were also normalised using the internal GAPDH standard (FIG. 15).

Assessment of HES5 and HEY2 can be used to provide a robust pharmacodynamic readout of Syntana-4 activity in tumour tissue. This provides evidence for target gene transcriptional inhibition. Gene expression analysis showed that HES5 and HEY2 genes are consistently down-regulated in MDA-MB231 xenograft tumours treated with Syntana-4. There is a variable effect on other tested genes. Hes-5 seems to be more affected (6-fold to 20-fold reduction in mRNA expression) than Hes-2 (up to 3-fold).

Example 8: Immuno-Histochemistry of Syntana-Treated Tumours

Immuno-histochemistry staining was performed using a Ki67 antibody assay to evaluate the effect of Syntana-4 on the proliferative capacity of tumour cells (FIG. 16). Tumours were exposed to either Syntana-4 or saline according to the table below.

| | | | |
|---|---|---|---|
| 1-1 | Syntana-4 treated | Mouse 2 | no reduction |
| 1-2 | Syntana-4 treated | Mouse 2 | significant reduction |
| 1-2(2) | Syntana-4 treated | Mouse 2 (area 2) | no significant reduction |
| 1-3 | Syntana-4 treated | Mouse 3 | no significant reduction |
| 1-4 | Syntana-4 treated | Mouse 4 | significant reduction |
| 1-4 | Syntana-4 treated | Mouse 4 (area 2) | no significant reduction |
| 1-6 | Syntana-4 treated | Mouse 6 | no significant reduction |
| 2-1 | Saline treated | Mouse 1 | no reduction |
| 2-2 | Saline treated | Mouse 1 | no reduction |

Ki67 staining is positive in greater than 80% of cells in control tumours (arrows). This is expected for an MDA-MB-231 xenograft model. There is a moderate but significant reduction in tumours 1-2, and 1-4, where between 40-60% of cells show positive Ki67 staining (bold arrows). Therefore, there is significant reduction in cellular proliferation in areas of tumours treated with Syntana-4 compared to no reduction in any areas treated with a saline control.

Example 9: Syntana-4 Causes Apoptosis of MDA-MB-231 Cells

Apoptotic cells were identified and quantified by Annexin V-DAPI staining. Cells were plated at 15,000 cells/well and treated 48 h later in triplicate with Syntana-4, ANTP or doxorubicin. After 72 h, cells were analysed by flow cytometry. Syntana-4, as expected from the mechanism of action, causes increased apoptosis (FIG. 17a, top right quadrant). Apoptotic cells as a percentage of the total number of collected cells was calculated from the histograms.

Example 10: Syntana-4 Causes Growth Inhibition MDA-MB-231 Cells

Following treatment of MDA-MB-231 cells with either Syntana-4, GSI-1 inhibitor or ANTP, cell proliferation was quantified. Cells were plated at 5000 cells/well and treated 48 h later. Test agents were exposed for 72 h and cell proliferation measured by Cell Titre-96 assay (Promega). Each point is a mean±SD. The carrier solution of 1% DMSO (for GSI-1) had no effect on the cells (Abs=0.85). Untreated control Abs=0.89. One-way ANOVA was used for statistical comparison. Proliferation, was shown to be significantly inhibited in Syntana-4 treated cells using a one-way ANOVA test (FIG. 18).

---

The invention claimed is:

1. A peptide conjugate comprising:
   a. a first region comprising a cell-penetrating peptide comprising SEQ ID NO:4 or a peptide having at least 80% sequence identity thereto; conjugated to
   b. a second region comprising a peptide that is an inhibitor of the Notch signalling pathway comprising SEQ ID NO:9 or a variant of SEQ ID NO: 9 according to the sequence:

(SEQ ID NO: 9)
   LPRHSAVMERLRRRIELCRRHHSTCEARYEAVSPERLELERQHTFALHQRC
   IQAKAKRAGKH wherein the underlined residues are conserved and up to 15 of the other residues are replaced by conservative substitutions; and
   c. a connecting peptide between the first and the second region that is from 5 to 10 amino acids in length and that comprises the amino acid sequence GEFMA (SEQ ID NO: 28);
   wherein the total length of the peptide conjugate is no more than 190 amino acids.

2. The conjugate of claim 1, wherein the first region comprises a cell-penetrating peptide comprising SEQ ID NO:2, or a peptide having at least 80% sequence identity thereto.

3. The conjugate of claim 1, wherein the first region is SEQ ID NO:2 or SEQ ID NO:3.

4. The conjugate of claim 3, wherein the first region is SEQ ID NO:2.

5. The conjugate of claim 1, wherein the second region is SEQ ID NO:9.

6. The conjugate of claim 1, in which the connecting peptide is from five to seven amino acids in length.

7. The conjugate of claim 1, in which the connecting peptide is GEFMA (SEQ ID NO: 28).

8. The conjugate of claim 1, comprising SEQ ID NO:10.

9. The conjugate of claim 1, comprising SEQ ID NO:12.

10. The conjugate of claim 1, wherein the total length of the peptide conjugate is no more than 150 amino acids.

11. A pharmaceutical composition comprising the conjugate of claim 1 and a pharmaceutically acceptable carrier.

12. The composition of claim 11, wherein the concentration of the conjugate is from 1 to 50 mg/mL.

13. A kit comprising the conjugate of claim 1 and one or more additional therapeutic agents suitable for simultaneous administration, sequential administration or separate administration.

14. A method of treating cancer or inhibiting the Notch signalling pathway in cancer stem cells or precursor cells, comprising administering the conjugate of claim 1 to a subject in need thereof.

15. The method of claim 14, wherein the concentration of the conjugate administered to the subject being treated is from 1 to 50 mg/mL.

16. The method of claim 14, wherein the conjugate is administered subcutaneously.

17. The method of claim 14, wherein the conjugate is formulated as a unit dose comprising from 1 mg to 200 mg of the conjugate.

18. The method of claim 14, wherein the method comprises co-administration or sequential administration of the conjugate or composition with a chemotherapeutic drug.

19. A method of preparing a peptide conjugate as defined in claim 1 using solid phase peptide synthesis, the method comprising coupling a first amino acid to a support and performing at least one coupling reaction to prepare the peptide conjugate.

* * * * *